(12) United States Patent
Parker et al.

(10) Patent No.: US 12,193,183 B2
(45) Date of Patent: Jan. 7, 2025

(54) ELECTRONIC DEVICE DISPLAY AND HOUSING ASSEMBLY

(71) Applicant: Apple Inc., Cupertino, CA (US)

(72) Inventors: Michael R. Parker, Loomis, CA (US); Daniel T. McDonald, San Jose, CA (US); Devon K. Copeland, San Francisco, CA (US); Tyler S. Atura Bushnell, San Francisco, CA (US); Christopher M. Werner, San Jose, CA (US); Michael A. Fisher, San Jose, CA (US); Natalie Y. Homsi, San Francisco, CA (US); Alexandros J. Petrakis, San Francisco, CA (US); Trent J. Canales, Roseville, CA (US)

(73) Assignee: APPLE INC., Cupertino, CA (US)

( * ) Notice: Subject to any disclaimer, the term of this patent is extended or adjusted under 35 U.S.C. 154(b) by 149 days.

(21) Appl. No.: 17/934,275

(22) Filed: Sep. 22, 2022

(65) Prior Publication Data
US 2023/0232560 A1   Jul. 20, 2023

Related U.S. Application Data

(60) Provisional application No. 63/374,738, filed on Sep. 6, 2022, provisional application No. 63/364,012, filed
(Continued)

(51) Int. Cl.
*H05K 5/06* (2006.01)
*G04G 17/04* (2006.01)

(52) U.S. Cl.
CPC ............... *H05K 5/06* (2013.01); *G04G 17/04* (2013.01)

(58) Field of Classification Search
CPC ...... G06F 1/163; G06F 1/1656; G06F 1/1633; G06F 1/1684; G06F 1/203
See application file for complete search history.

(56) References Cited

U.S. PATENT DOCUMENTS 8,630,441 B2   1/2014  Shi et al.
8,818,006 B2   8/2014  Yamauchi et al.
(Continued)

FOREIGN PATENT DOCUMENTS

CN   112788480 A    5/2021
EP     3617814 A1   3/2020
(Continued)

OTHER PUBLICATIONS

Extended European Search Report for EP Application No. 23151557.8, mailed Oct. 11, 2023 (15 pp.).
(Continued)

*Primary Examiner* — James Wu
*Assistant Examiner* — Dakota M Talbert
(74) *Attorney, Agent, or Firm* — Dorsey & Whitney LLP

(57) ABSTRACT

An electronic device includes a housing sidewall defining an opening and a display component, such as a display cover, disposed in the opening to form a gap between the housing sidewall and the display component. In at least one example, the cavity is defined by the sidewall and the display cover with the cavity in fluid communication with an external environment through the gap. In at least one example, an epoxy component at least partially defines the cavity and can be in direct contact with the housing sidewall.

18 Claims, 45 Drawing Sheets

Related U.S. Application Data on May 2, 2022, provisional application No. 63/266,829, filed on Jan. 14, 2022.

(56) References Cited

U.S. PATENT DOCUMENTS

| | | | |
|---|---|---|---|
| 10,484,958 B2 * | 11/2019 | Sayem | H05K 7/1427 |
| 10,599,101 B2 | 3/2020 | Rothkopf et al. | |
| 10,782,742 B1 | 9/2020 | Spencer et al. | |
| 11,553,608 B2 * | 1/2023 | Ko | G04B 37/084 |
| 2006/0146650 A1 | 7/2006 | Dinger | |
| 2009/0120715 A1 | 5/2009 | Saiki | |
| 2012/0045081 A1 | 2/2012 | Mittleman et al. | |
| 2013/0129135 A1 | 5/2013 | Gregg et al. | |
| 2015/0110335 A1 | 4/2015 | Telemaque et al. | |
| 2016/0058375 A1 | 3/2016 | Rothkopf | |
| 2017/0311812 A1 | 11/2017 | Husheer | |
| 2018/0020283 A1 | 1/2018 | Zhang et al. | |
| 2018/0077813 A1 | 3/2018 | Lancaster-Larocque et al. | |
| 2018/0173166 A1 * | 6/2018 | Kayano | G04G 17/08 |
| 2019/0045642 A1 | 2/2019 | Prest et al. | |
| 2019/0373360 A1 | 12/2019 | Yu et al. | |
| 2021/0275030 A1 | 9/2021 | Ghoreyshi | |
| 2023/0225619 A1 | 7/2023 | Tang et al. | |
| 2023/0229117 A1 | 7/2023 | Anderson et al. | |
| 2023/0229197 A1 | 7/2023 | Deschamps et al. | |
| 2023/0229205 A1 | 7/2023 | Deschamps et al. | |
| 2023/0232151 A1 | 7/2023 | Chiang et al. | |
| 2023/0232547 A1 | 7/2023 | Canales et al. | |

FOREIGN PATENT DOCUMENTS

| | | |
|---|---|---|
| EP | 3929668 A1 | 12/2021 |
| EP | 4027124 A1 | 7/2022 |
| KR | 20170001187 U | 3/2017 |
| WO | 2012127812 A1 | 9/2012 |
| WO | 2018016906 A1 | 1/2018 |
| WO | 2020198088 A1 | 10/2020 |
| WO | 2021057873 A1 | 4/2021 |
| WO | 2021231221 A1 | 11/2021 |

OTHER PUBLICATIONS

European Search Report for EP Application No. 23150549.6, mailed Jun. 9, 2023 (9 pp.).

European Search Report for EP Application No. 23150553.8, filed Jun. 15, 2023 (11 pp.).

European Search Report for EP Application No. 23150554.6, mailed Jun. 16, 2023 (11 pp.).

* cited by examiner

ELECTRONIC DEVICE DISPLAY AND HOUSING ASSEMBLY

CROSS-REFERENCE TO RELATED APPLICATION(S)

This claims priority to U.S. Provisional Patent Application No. 63/374,738, filed 6 Sep. 2022, and entitled "ELECTRONIC DEVICE," to U.S. Provisional Patent Application No. 63/364,012, filed 2 May 2022, and entitled "ELECTRONIC DEVICE," and to U.S. Provisional Patent Application No. 63/266,829, filed 14 Jan. 2022, and entitled "ELECTRONIC DEVICE," the disclosures of which are hereby incorporated by reference in their entireties.

FIELD

The present disclosure relates generally to electronic devices. More particularly, the present disclosure relates to wearable electronic devices.

BACKGROUND

Electronic devices are increasingly being designed with device portability in mind, for example, to allow users to use these devices in a wide variety of situations and environments. In the context of wearable devices, these devices can be designed to include many different functionalities and to be operated in many different locations and environments. The components of an electronic device, for example, the processors, memory, antennas, display, and other components can partially determine a level of performance of the electronic device. Further, the arrangement of these components with respect to one another in the device can also determine the level of overall performance of the electronic device.

Continued advances in electronic devices and their components have enabled considerable increases in performance. Existing components and structures for electronic devices can, however, limit the levels of performance of such devices. For example, while some components can achieve high levels of performance in some situations, the inclusion of multiple components in devices sized to enhance portability can limit the performance of the components, and thus, the performance of the device. Consequently, further tailoring and arrangement of components for electronic devices to provide additional or enhanced functionality, without introducing or increasing undesirable device properties, can be desirable.

SUMMARY

In at least one example of the present disclosure, a housing sidewall can define an opening and a display component, such as a display cover, can be disposed in the opening to form a gap between the housing sidewall and the display component. In at least one example, the cavity is defined by the sidewall and the display cover, with the cavity in fluid communication with an external environment through the gap. In at least one example, an epoxy component at least partially defines the cavity and can be in direct contact with the housing sidewall.

In at least one example of an electronic device, a housing sidewall includes an upper sidewall portion and a lower sidewall portion bonded to a middle sidewall portion disposed between the upper and lower sidewall portions. The housing can define an opening and the display assembly can be disposed in the opening to form the gap between the housing and the display assembly. Also, in at least one example, an epoxy component can serve as a seal disposed between the display assembly and the sidewall, the epoxy extending laterally across the gap with the epoxy component seal bonded directly to the middle portion of the sidewall.

In at least one embodiment, an electronic device can include a sidewall defining an internal volume and an opening. The sidewall can include an upper portion, a lower portion, and a middle portion disposed between and bonded to the upper portion and the lower portion. The device can also include a display cover disposed in the opening and defining the internal volume, a side cavity defined by the display assembly and the sidewall, the cavity in fluid communication with an external environment through a gap formed between the display assembly and the sidewall, and an epoxy layer contacting the lower portion and the middle portion and at least partially defining the cavity.

In at least one example embodiment, an electronic device can include an outer housing defining an internal volume, a first speaker and a second speaker disposed in the internal volume. The first speaker can include a frame disposed around a periphery of a diaphragm of the first speaker. A front volume can be defined by the outer housing, the first speaker, and the second speaker. Similarly, a first back volume can be defined by the first speaker and the frame, and a second back volume can be defined by the second speaker and the frame.

In at least one embodiment, an electronic device can include an outer housing, an inner housing spaced apart from the outer housing, and a speaker assembly disposed between the inner and outer housings. The speaker assembly can include a first speaker, a second speaker, and a speaker frame supporting the first speaker. The device can further include a first back volume defined by the inner housing and the first speaker, and a second back volume defined by the inner housing and the second speaker, the second back volume separated from the first back volume by the speaker frame.

In at least one example, an electronic device can include an outer housing, an inner housing, and a speaker assembly disposed between the inner housing and the outer housing. The speaker assembly can include a first speaker and a second speaker. The electronic device can further include a front volume defined by the outer housing and the speaker assembly, a back volume defined by the inner housing and the speaker assembly, a first vent through which a first end of the front volume is in fluid communication with an external environment, and a second vent through which a second end of the front volume is in fluid communication with the external environment. The back volume can be separated into first and second isolated portions.

In at least one embodiment, an electronic device can include a housing defining an internal volume and an aperture, a button disposed in the aperture, the button including a plunger extending into the internal volume, and a speaker frame disposed in the internal volume and defining an opening. The plunger can extend through the opening.

In at least one embodiment, an electronic device can include a housing defining an internal volume, a plunger extending into the internal volume, and a frame structurally supporting a first speaker and a second speaker. The frame can be disposed in the internal volume and define an opening between the first and second speakers. The plunger can be aligned with the opening.

In at least one embodiment, an electronic device can include an outer housing defining an aperture, an inner housing spaced apart from the outer housing and defining an internal volume, the inner housing and the outer housing defining a speaker volume, a button having a plunger, the button disposed in the aperture, and a speaker assembly including a speaker frame defining a hole. The plunger can be aligned with the hole and can extend into the speaker volume toward the inner housing.

In at least one embodiment, an electronic device can include a sidewall including an antenna and defining an internal volume, a printed circuit board (PCB) disposed in the internal volume, an insulating material disposed in the internal volume, and an electrical connector contacting the PCB, the electrical connector extending through the insulating material and forming an electrical contact between the antenna and the PCB.

In at least one exemplary embodiment, an electronic device can include a conductive housing sidewall defining an internal volume, a printed circuit board (PCB) disposed in the internal volume, an electrical connector contacting the PCB and extending through an insulating material, and an elongate conductive member disposed between the housing sidewall and the electrical connector, the elongate conductive member contacting the electrical connector and the housing sidewall.

In at least one embodiment, an electronic device includes a housing sidewall including a lower portion and an electrically conductive upper portion separated from the lower portion by a non-conductive material, the housing sidewall defining an internal volume and an opening, a display component disposed in the opening, a printed circuit board (PCB) disposed in internal volume below the display component, an insulating material disposed in the internal volume between the housing sidewall and the PCB, and a connector forming an electrical pathway between the upper conductive portion of the sidewall and the PCB. The upper portion can form a ring surrounding a periphery of the display component.

In at least one embodiment, a wearable electronic device can include a housing having a sidewall. The sidewall can define an internal volume, the sidewall extending 360-degrees circumferentially around the internal volume. The sidewall can also define a first aperture, a second aperture between about 155 and 205 degrees relative to the first aperture, and a third aperture closer to the second aperture than the first aperture. The wearable electronic device can further include a first microphone disposed in the internal volume and configured to receive sound through the first aperture, a second microphone disposed in the internal volume and configured to receive sound through the second aperture, and a third microphone disposed in the internal volume and configured to receive sound through the third aperture.

In at least one embodiment, a wearable electronic device can include a housing sidewall defining an internal volume, a first band receiving feature, a second band receiving feature opposite the first band receiving feature, a first sidewall portion extending between the first band receiving feature and the second band receiving feature, the first sidewall portion defining a first aperture closer to the first band receiving feature than the second band receiving feature, a second sidewall portion disposed opposite the first sidewall portion and extending between the first band receiving feature and the second band receiving feature, the second sidewall portion defining a second aperture and a third aperture, the second aperture defined closer to the second band receiving feature than the first band receiving feature. The wearable electronic device can further include a first microphone disposed in the internal volume adjacent the first aperture, a second microphone disposed in the internal volume adjacent the second aperture, and a third microphone disposed in the internal volume adjacent the third aperture.

In at least one example of the present disclosure, an electronic device can include a sidewall defining an internal volume, a first aperture, a second aperture, a third aperture, and a fourth aperture, a first microphone disposed in the internal volume adjacent the first aperture, a second microphone disposed in the internal volume adjacent the second aperture, a third microphone disposed in the internal volume adjacent the third aperture, and a speaker disposed in the internal volume adjacent the fourth aperture. A distance along the sidewall between the first and second apertures can be larger than a distance along the sidewall between the second and third apertures and the fourth aperture can be adjacent the first aperture.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative examples illustrated in the accompanying drawings. It should be understood that the following descriptions are not intended to limit the embodiments to one preferred example or embodiment. To the contrary, it is intended to cover alternatives, modifications, and equivalents as can be included within the spirit and scope of the described embodiments as defined by the appended claims.

The following disclosure generally relates to electronic devices. More particularly, the present disclosure relates to wearable electronic devices. The wearable electronic devices of the present disclosure include tailored arrangements of components to provide additional or enhanced functionality, without introducing or increasing undesirable device properties or performance. In this way, more functionality and componentry can be included in wearable devices for user's to wear and operate in any condition or activity without limiting the functionality and durability of the devices.

Specific examples and embodiments of electronic devices, including wearable electronic devices, are discussed below with reference to FIGS. 1-28. However, those skilled in the art will readily appreciate that the detailed description given herein with respect to these Figures is for explanatory purposes only and should not be construed as limiting. Furthermore, as used herein, a system, a method, an article, a component, a feature, or a sub-feature comprising at least one of a first option, a second option, or a third option should be understood as referring to a system, a method, an article, a component, a feature, or a sub-feature that can include one of each listed option (e.g., only one of the first option, only one of the second option, or only one of the third option), multiple of a single listed option (e.g., two or more of the first option), two options simultaneously (e.g., one of the first option and one of the second option), or combination thereof (e.g., two of the first option and one of the second option).

Figure 1A:
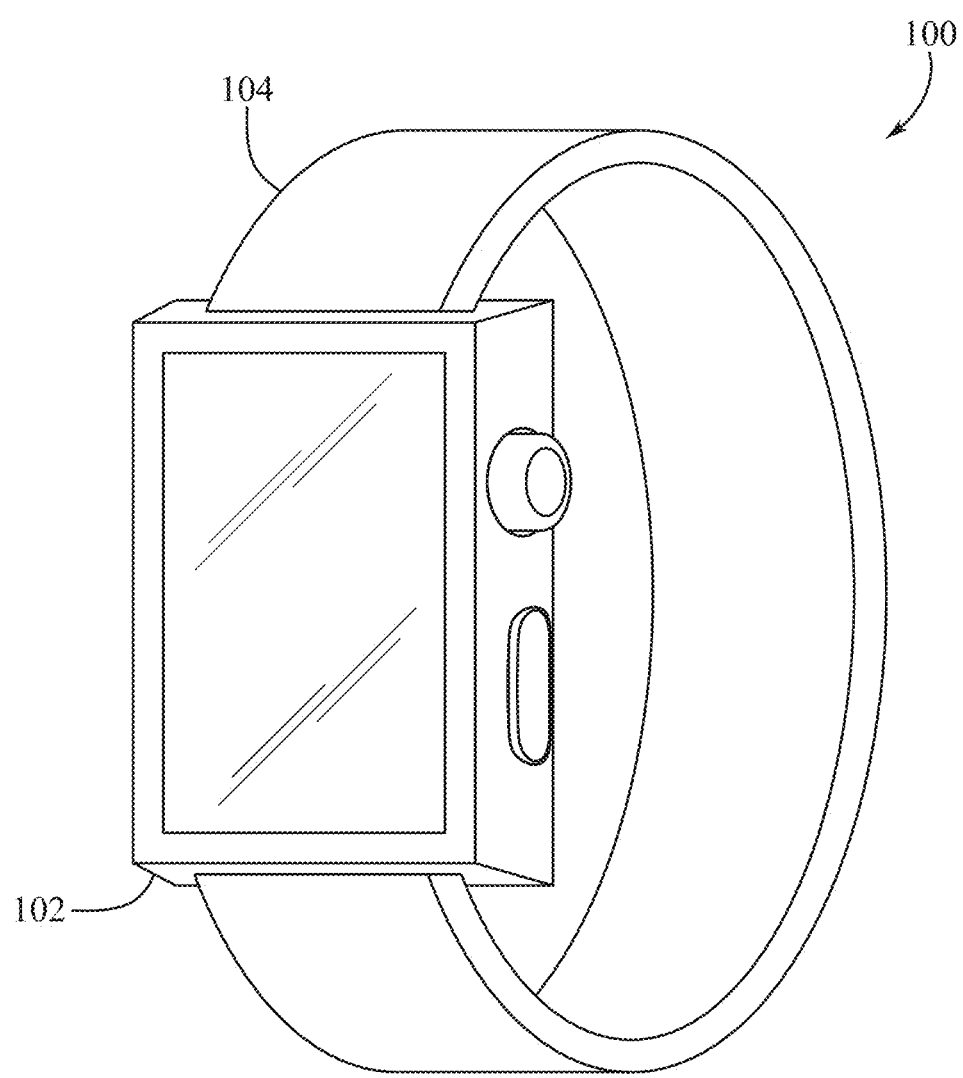
FIG. 1A shows an example of a wearable electronic device.

FIG. 1A shows an example of an electronic device 100. The electronic device shown in FIG. 1A is a watch, such as a smartwatch. The smartwatch of FIG. 1A is merely one representative example of a device that can be used in conjunction with the systems and methods disclosed herein. Electronic device 100 can correspond to any form of wearable electronic device, a portable media player, a media storage device, a portable digital assistant ("PDA"), a tablet computer, a computer, a mobile communication device, a GPS unit, a remote control device, or other electronic device. The electronic device 100 can be referred to as an electronic device, or a consumer device. In some examples, the electronic device 100 can include a housing 102 that can carry operational components, for example, in an internal volume at least partially defined by the housing. The electronic device 100 can also include a strap 104, or other retaining component that can secured the device 100 to a body of a user as desired. Further details of the electronic device are provided below with reference to FIG. 1B.

Figure 1B:
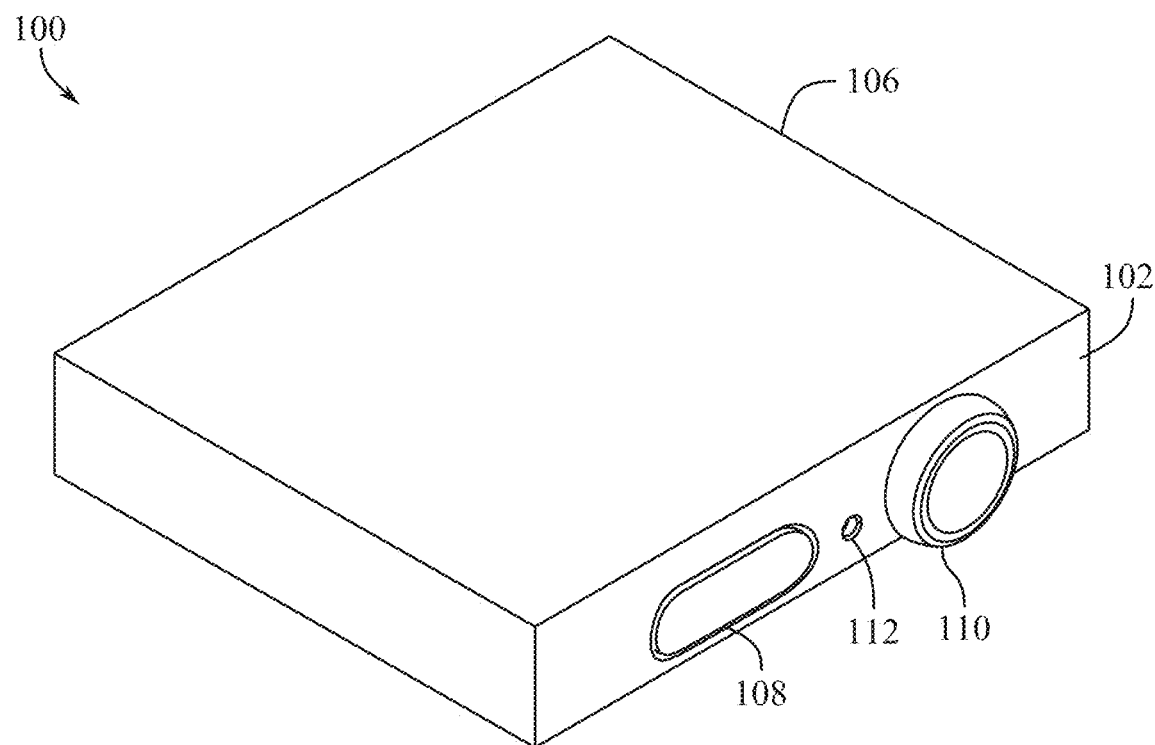
FIG. 1B shows a top view of a portion of the wearable electronic device.

FIG. 1B illustrates the electronic device 100, for example a smartwatch, that can be substantially similar to and can include some or all of the features of the devices described herein, including the electronic device 100 shown in FIG. 1A but without the strap 104. The device 100 can include a housing 102, and a display assembly 106 attached to the housing 102. The housing 102 can substantially define at least a portion of an exterior surface of the device 100.

The display assembly 106 can include a glass, a plastic, or any other substantially transparent exterior layer, material, component, or assembly. The display assembly 106 can include multiple layers, with each layer providing a unique function, as described herein. Accordingly, the display assembly 106 can be, or can be a part of, an interface component. The display assembly 106 can define a front exterior surface of the device 100 and, as described herein, this exterior surface can be considered an interface surface. In some examples, the interface surface defined by display assembly 106 can receive inputs, such as touch inputs, from a user.

In some examples, the housing 102 can be a substantially continuous or unitary component and can define one or more openings to receive components of the electronic device 100. In some examples, the device 100 can include input components such as one or more buttons 108 and/or a crown 110 that can be disposed in the openings. In some examples, a material can be disposed between the buttons 108 and/or crown 110 and the housing 102 to provide an airtight and/or watertight seal at the locations of the openings. The housing 102 can also define one or more openings or apertures, such as aperture 112 that can allow for sound to pass into or out of the internal volume defined by the housing 102. For example, the aperture 112 can be in communication with a microphone component disposed in the internal volume. In some examples, the housing 102 can define or include a feature, such as an indentation to removably couple the housing 102 and a strap or retaining component.

Figure 1C:
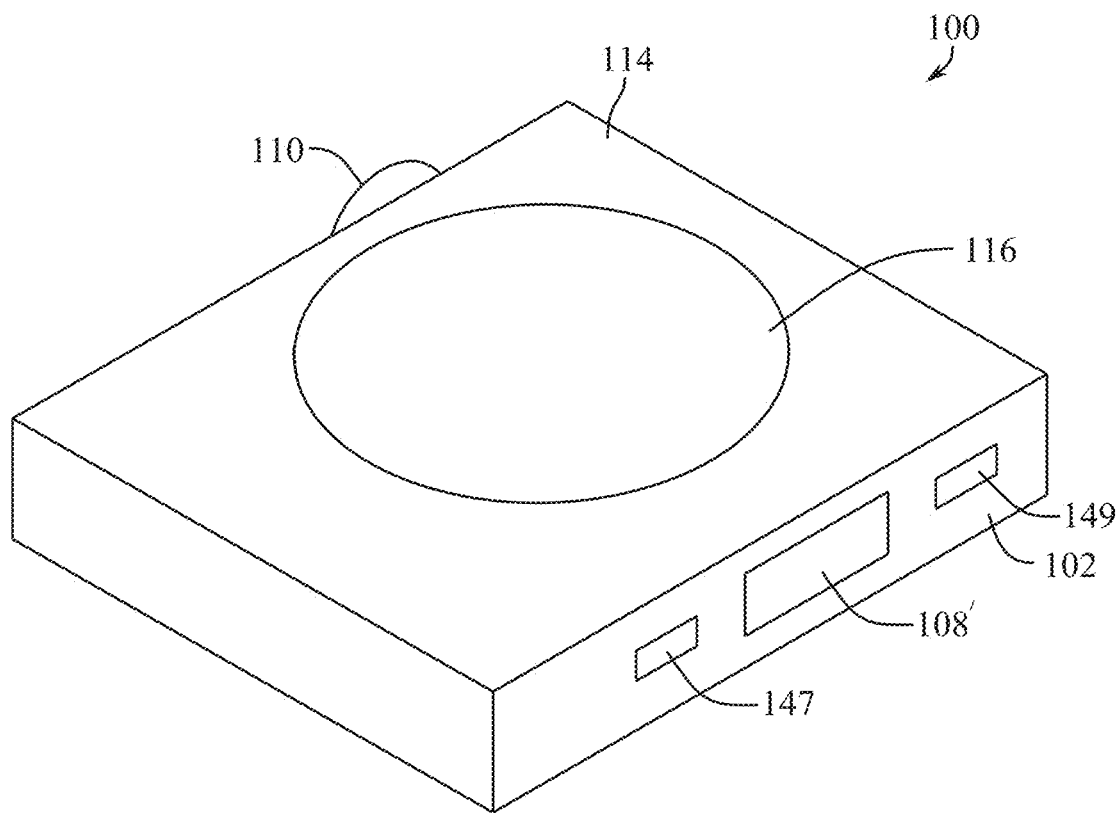
FIG. 1C shows a bottom view of a portion of the wearable electronic device.

FIG. 1C shows a bottom perspective view of the electronic device 100. The device 100 can include a back cover 114 that can be attached to the housing 102, for example, opposite the display assembly 106. The back cover 114 can include ceramic, plastic, metal, or combinations thereof. In some examples, the back cover 114 can include an at least partially electromagnetically transparent component 116. The electromagnetically transparent component 116 can be transparent to any desired wavelengths of electromagnetic radiation, such as visible light, infrared light, radio waves, or combinations thereof. In some examples, the electromagnetically transparent component 116 can allow sensors and/or emitters disposed in the housing 102 to communicate with the external environment. Together, the housing 102, display assembly 106 and back cover 114 can substantially define an internal volume and an external surface of the device 100.

Any of the features, components, and/or parts, including the arrangements and configurations thereof shown in FIGS. 1A-1C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 1A-1C.

As noted above, portable and wearable electronic devices can be designed to be used in many different environments and during any kind of activity throughout a user's day. For example, wearable electronic watches, headphones, and phones can be carried by a user during exercise, sleep, driving, biking, hiking, swimming, diving, outside in the rain, outside in the sun, and so forth. Wearable electronic devices described herein are configured to withstand the varied and often harsh conditions of various environments, including changing environments and wet environments. Wet environments can include wearing devices in the rain or when submerged during bathing or swimming, for example.

Examples of electronic devices disclosed herein include components, features, arrangements, and configurations that resists damage and corrosion due to exposure to moisture. Some aspects of devices described herein can include gaps between components through which moisture, water, or other fluids could enter. The gaps may be present for aesthetic purposes or for functional purposes. However, one or more components, including epoxy seals, insulating materials and frames, and other components of devices described herein can be configured to prevent such moisture from entering into the internal volume of the device where sensitive electronic component could be damaged thereby.

Figure 2A:
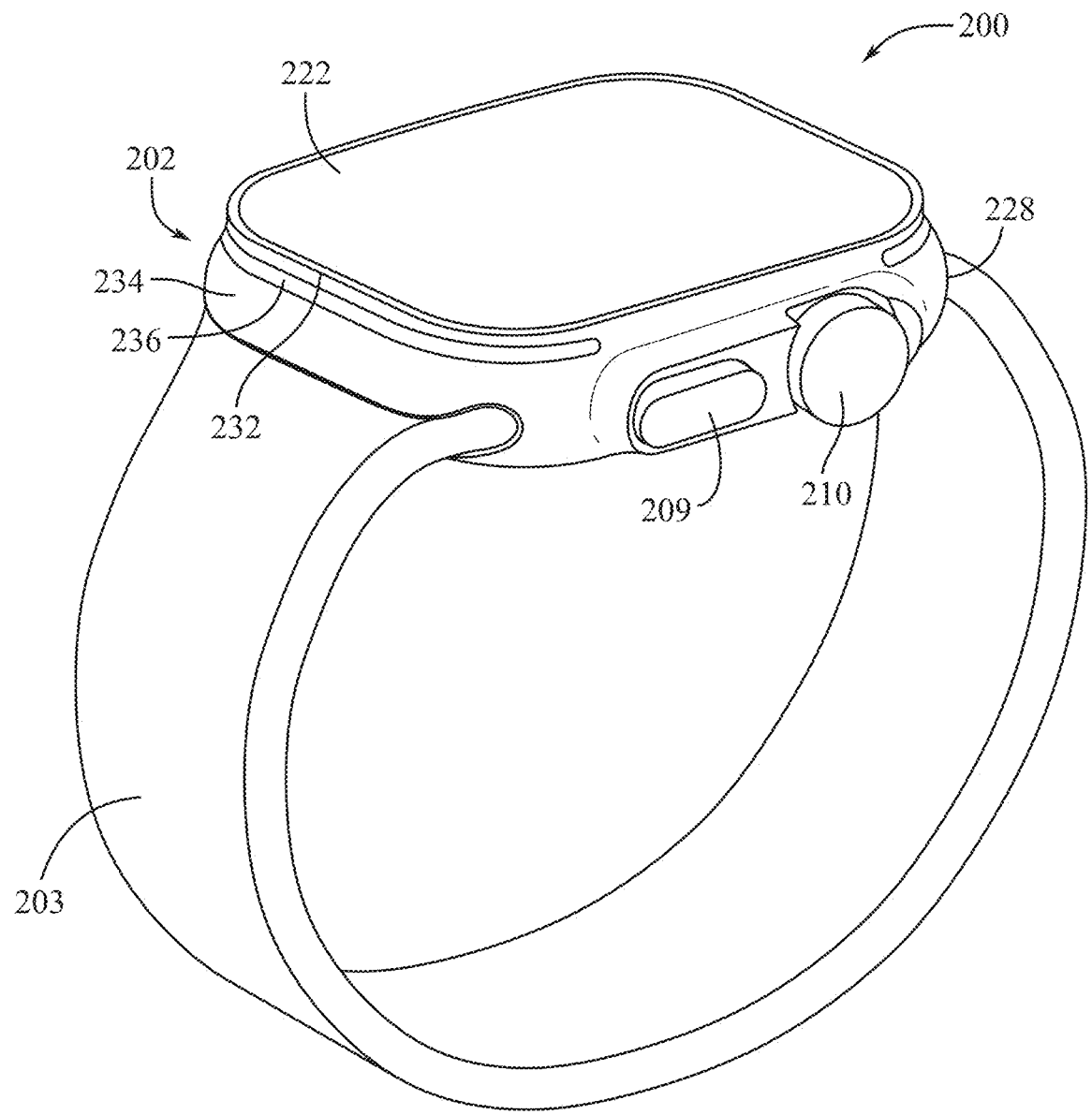
FIG. 2A shows a perspective view of an example of a wearable electronic device.
Figure 2B:
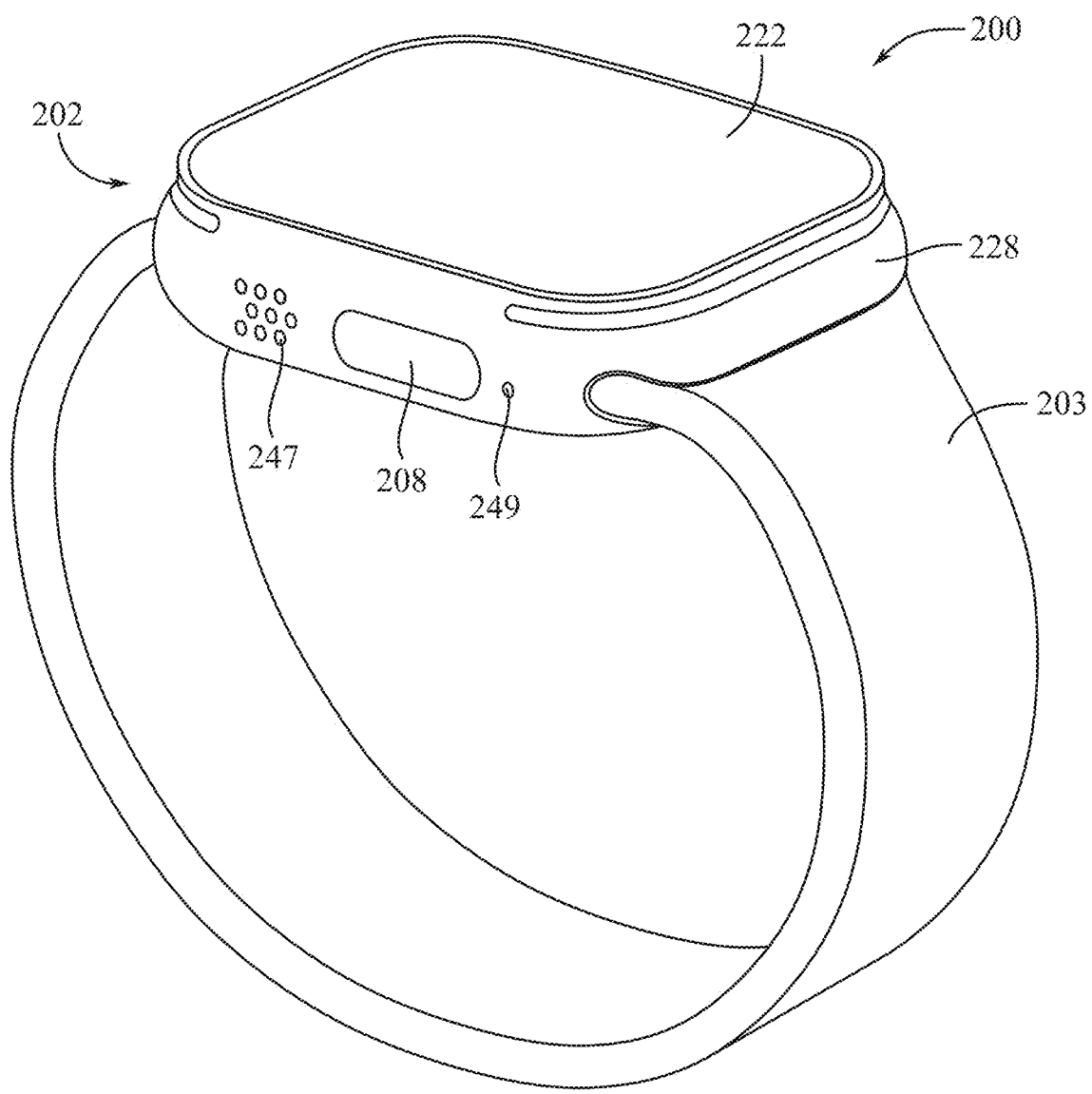
FIG. 2B shows a perspective view of an example of a wearable electronic device.

Along these lines, FIGS. 2A and 2B show right and left perspective views, respectively, of an example of a wearable electronic device 200 including a housing 202 including sidewalls 228 defining an opening in which the display cover 222 is disposed. The sidewalls can include an upper portion 232 defining an upper peripheral edge surrounding the display cover 222, a lower portion 234, and a middle portion 236 disposed between the upper portion 232 and the lower portion 234. The wearable electronic device 200 can also include a securement strap 203 configured to secure the wearable electronic device 200 to an appendage of the user. In at least one example, the sidewalls 228 of the housing 202 can define an upper peripheral edge of the device 200 surrounding the display cover 222.

In at least one example, the display cover 222 defines a top surface disposed in a plane. The plane can be flush with or set below the upper peripheral edge of the sidewalls 228. In this way, when the wearable electronic device 200 comes into contact with a surface or object at or near the upper surface of the display cover 222 and/or the upper peripheral edge of the sidewalls 228, contact and potential damage to the display cover 222 can be reduced. In one example, the display cover 222 is set flush with or below the upper peripheral edges of the sidewalls 228 to protect the display cover 222 from damage.

In at least one example, as shown in FIG. 2A, the sidewalls 228 can define a first side of the wearable electronic device 200 having a recessed feature in which a crown 210 is positioned. The crown 210 can be a part of a turn dial button or other functional knob configured to be manipulated by the user. The crown 210 can be disposed in the recessed portion, as noted above, such that first side of the sidewalls 228 extend outward and at least partially around the crown 210. In this way, contacts and bumps against of other objects against the first side of the sidewall 228 during use can contact the sidewall 228 without pressing or turning the crown 210. In this way, the recessed portion of the first side of the sidewalls 228 prevents inadvertent manipulation of the crown 210. The button 209 shown in FIG. 2A can also be at least partially surrounded by an outwardly extending portion of the sidewall 228, such that the button 209 is disposed within a recess thereof, to protect the button 209 form inadvertent contacts.

In at least one example, as shown in FIG. 2B, the sidewalls 228 can define a second side opposite the first side shown in FIG. 2A. In such an example, the wearable electronic device 200 can include a first speaker vent 249, a second speaker vent 247, and a button 208 disposed between the first speaker vent 249 and the second speaker vent 247. The first and second speaker vents 249, 247 can provide fluid communication from a common speaker volume behind the sidewall 228 (e.g., within an internal volume defined by the sidewalls 228) and the external environment. The button 208 can be disposed between the first and second speaker vents 249, 247 to save space and provide a compact design without interrupting the functionality of the one or more speakers communicating with the external environment through the first and second speaker vents 247, 249.

Figure 2C:
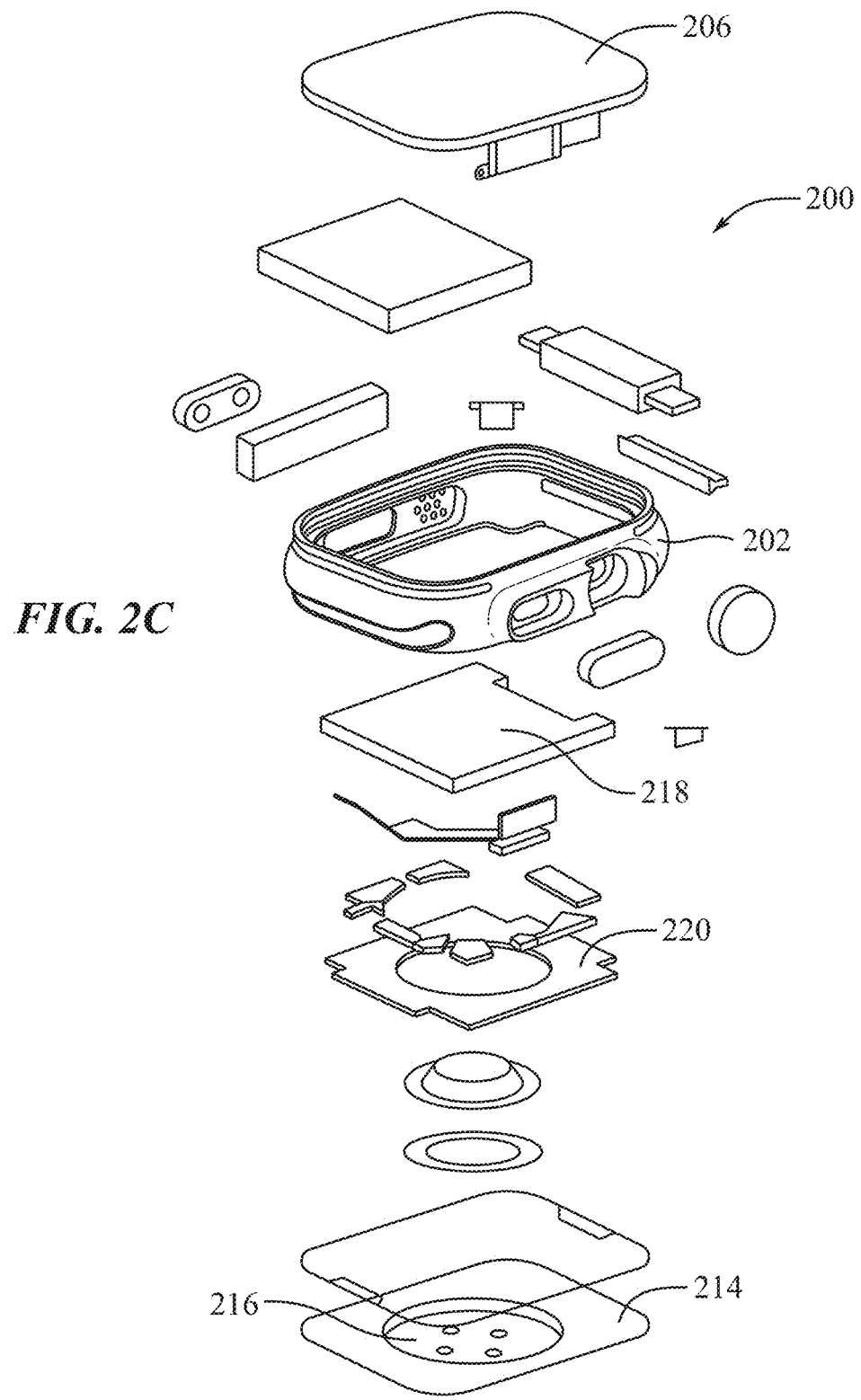
FIG. 2C shows an exploded view of an example of a wearable electronic device.

FIG. 2C illustrates an exploded view of another example of an electronic device 200, which can also be a portion of a wearable electronic watch or other wearable electronic device. Device 200 includes a display assembly 206, housing 202, back cover 214, and electromagnetically transparent component 216. In addition, the exploded view of FIG. 2A illustrates various internal components that may be disposed within an internal volume defined by the housing 202, back cover 214, electromagnetically transparent component 216, and display assembly 206. For example, the device 200 can include one or more printed circuit boards (PCBs) 218 and one or more antenna components 220, electrical connectors and flexes, buttons, seals, gaskets, memory components, processors, sensors, dials, batteries, and so forth.

Any of the features, components, and/or parts, including the arrangements and configurations thereof shown in FIGS. 2A-2C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 2A-2C.

Figure 3:
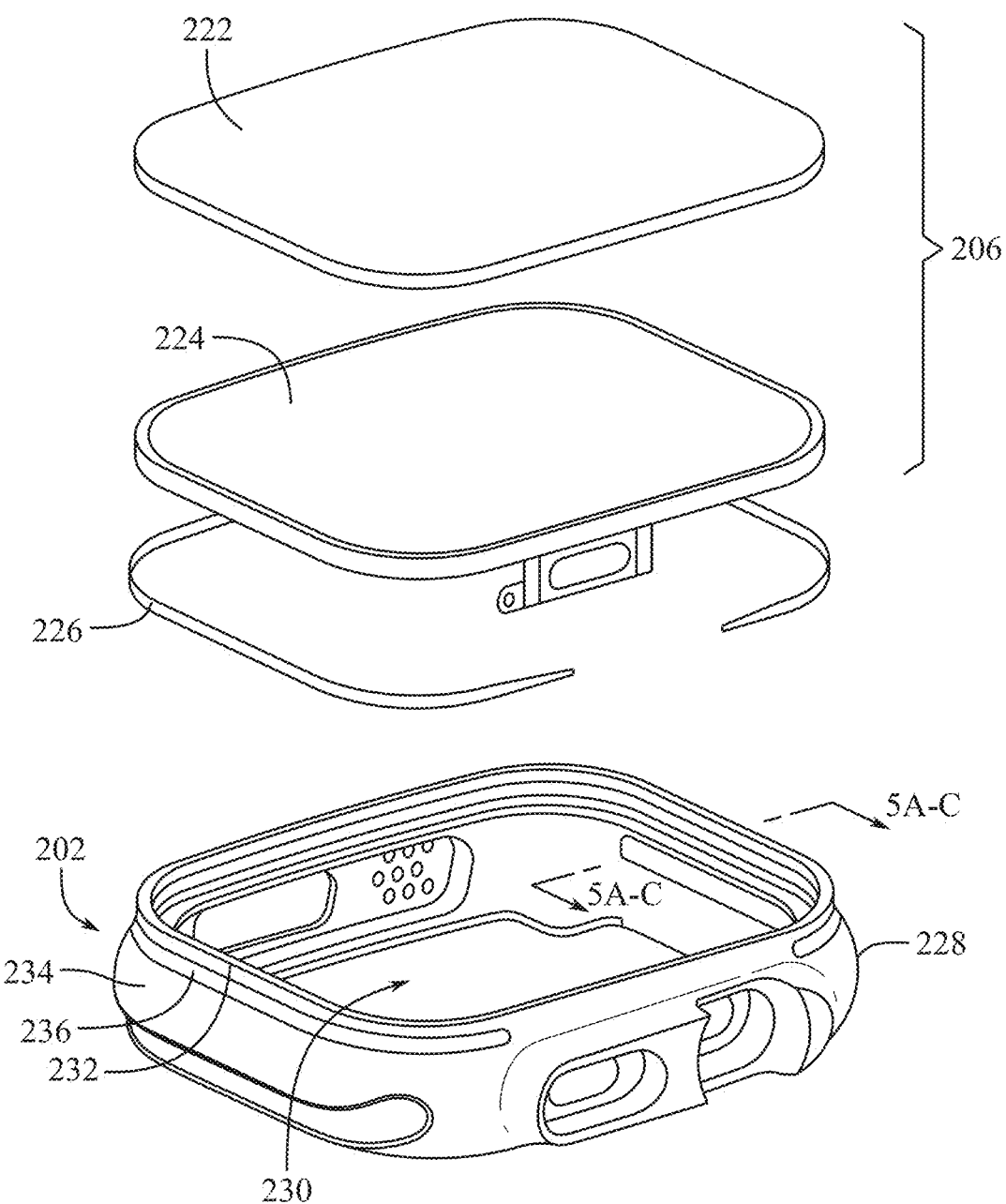
FIG. 3 shows an exploded view of an example of a wearable electronic device.

FIG. 3 illustrates a close-up view of a portion of the exploded view of the device 200 shown in FIG. 2, including the housing 202 and the display assembly 206, with the display assembly further exploded to illustrate the display cover 222 and display layers 224. In addition, the exploded view of FIG. 3 shows a wave ring 226 (also referred to herein as an "elongate conductive member"), which will be described and discussed in more detail hereafter with reference to other figures. In at least one example, the housing 202 includes sidewall or sidewalls 228 that define an internal volume and an opening 230. When assembled, the display assembly 206 or one or more components of the display assembly 206 can be disposed in the opening to form an outer surface of the device 200 and define the internal volume.

In at least one example, the sidewall 228 can include an upper portion 232 and a lower portion 234. The upper portion 232 and the lower portion 234 can be separated by a middle portion 236 disposed between the upper portion 232 and the lower portion 234. In at least one example, the upper portion 232 and the lower portion 234 of the sidewall 228 can include one or more electrically conductive materials and the middle portion 236 can include one or more electrically non-conductive materials and/or an insulating material. The middle portion 236 can be molded to or otherwise adhered to the upper portion 232 and/or the lower portion 234 such that the upper portion 232, the lower portion 234, and the middle portion 236 form a single, unitary sidewall 228 of the housing 202, as shown.

Any of the features, components, and/or parts, including the arrangements and configurations thereof shown in FIG. 3 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 3.

Figure 4:
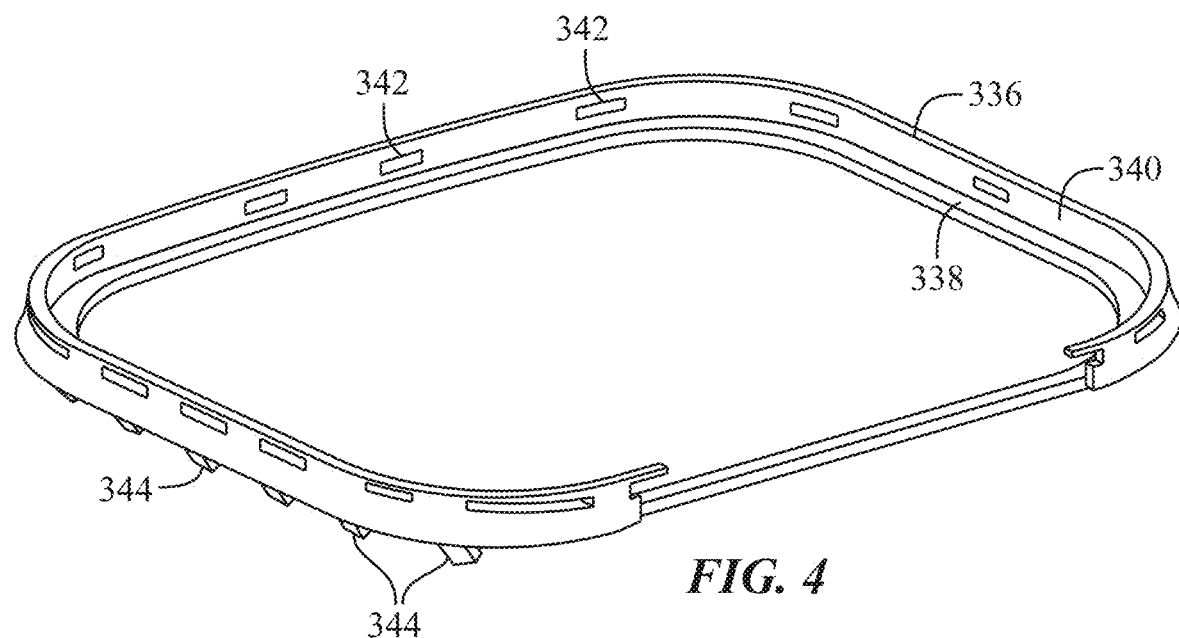
FIG. 4 shows a portion of a sidewall of an example of a wearable electronic device.
Figure 5A:
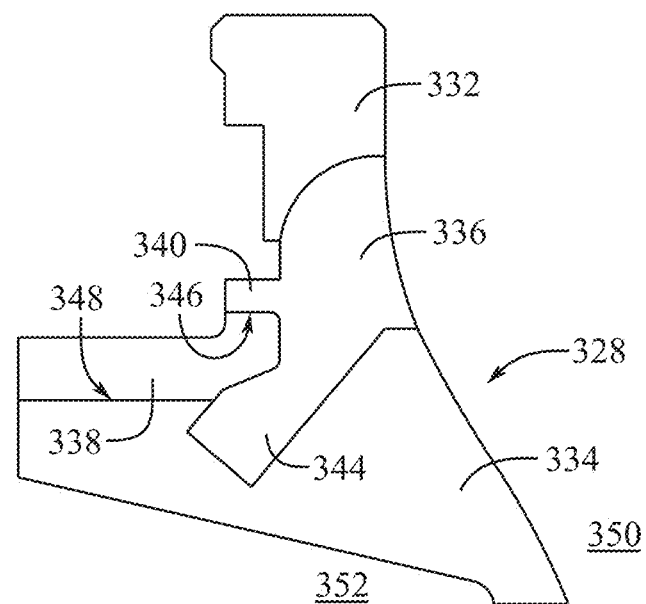
FIG. 5A shows a cross-sectional view of a sidewall of an example of a wearable electronic device.
Figure 5B:
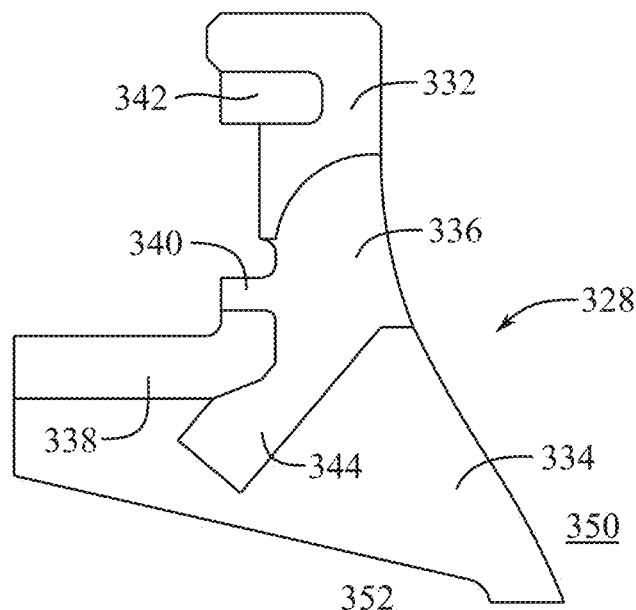
FIG. 5B shows another cross-sectional view of a sidewall of an example of a wearable electronic device.
Figure 5C:
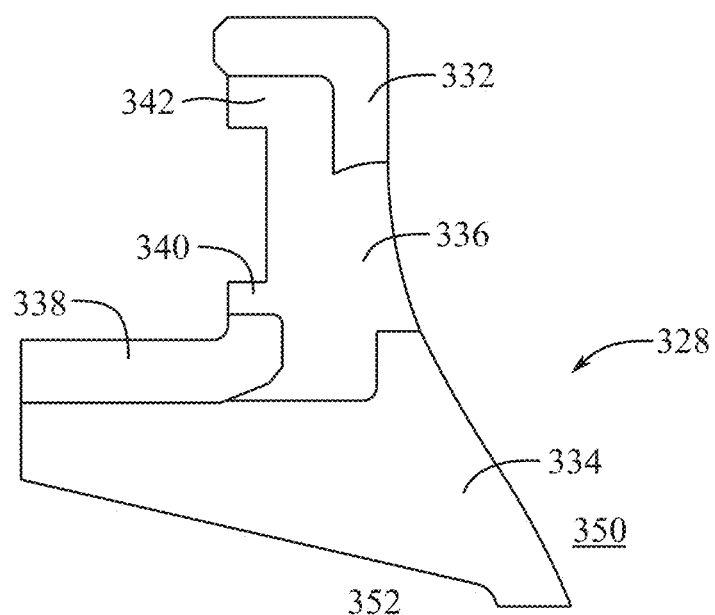
FIG. 5C shows another cross-sectional view of a sidewall of an example of a wearable electronic device.

FIG. 4 illustrates an example of a middle portion 336 separated from the rest of a sidewall of a housing, similar to the middle portion 236 shown as part of the sidewall 228 of FIG. 3. In the example shown in FIG. 4, a non-conductive material component or ring 338 is bonded to the middle portion 336. In at least one example, the non-conductive material ring 338 can include an epoxy component 338. The term "epoxy," as used herein, can include non-conductive adhesives as generally used and understood in the art, including hot-melt adhesives. The middle portion 336 can also include a ridge feature 340 extending at least partially around an internal surface of the middle portion 336. The ridge feature 340 can form a lower surface of the middle portion 336. In addition, at least one example, the middle portion 336 can include one or more upper protrusions 342 spaced about and extending inward relative to an external surface of the sidewall 328. In addition, at least one example of the middle portion 336 can include one or more lower protrusions 344 spaced about and extending from the middle portion 336, as shown in FIG. 4. FIGS. 5A, 5B, and 5C illustrate partial cross-sectional views, as indicated in FIG. 3, but around various points along the sidewall 228 in order to illustrate the positions and configurations of the middle portion 336, epoxy component 338, upper portion 332, and lower portion 334.

Any of the features, components, and/or parts, including the arrangements and configurations thereof shown in FIG. 4 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 4.

In the first cross-sectional view of FIG. 5A, the ridge feature 340 and lower protrusion 344 of the middle portion 336 can be seen. In at least one example, the epoxy component 338 is bonded to an upper surface 348 defined by the lower portion 334 of the sidewall 328. The epoxy component 338 can also be bonded directly to the middle portion 336, for example including the lower protrusion 344 and a lower surface 346 of the middle portion 336 defined by the ridge feature 340. FIG. 5B illustrates another cross-sectional view at a point along the sidewall 328 where an upper protrusion 342 and a lower protrusion 344 of the middle portion 336 can be seen and FIG. 5C illustrates another cross-sectional view at a point along the sidewall 328 where an upper protrusion 342 of the middle portion 336 can be seen.

Figure 6:
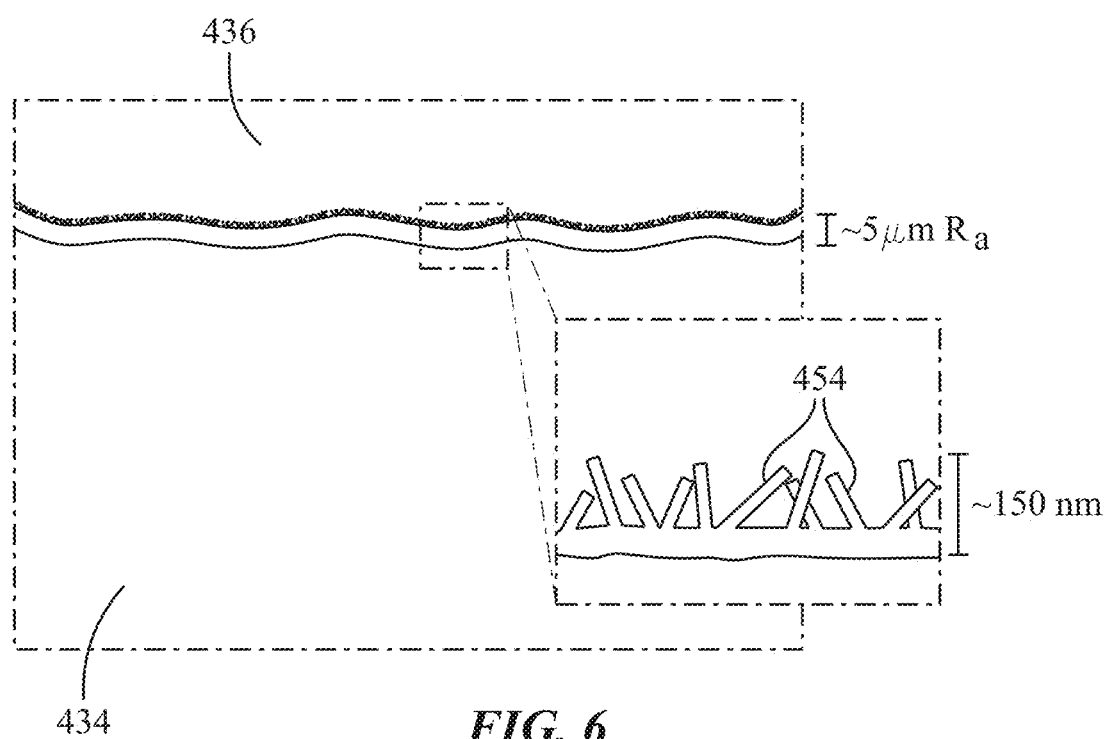
FIG. 6 shows a cross sectional view of an interface between a plastic and metal portion of a sidewall of an example of an electronic device.

As shown in FIGS. 5A, 5B, and 5C, any possible path for moisture to travel from an external environment 350 to the internal volume 352 through the sidewall 328 of the device is blocked by the epoxy component 338 bonded directly to either the lower portion 334 of the sidewall 328 or the middle portion 336. Thus, the tight bond of the epoxy component 338 against one or more portions 334, 336 prevents water and moisture from entering into the internal volume 352 from the external environment 350 through the sidewall 328. In addition to the moisture-tight bond between the epoxy component 338 and the sidewall 328, in at least one example, the middle portion 336 of the sidewall 328 can be bonded to the upper and lower portions 332, 334, respectively, such that the bond therebetween substantially or completely prevents moisture from passing through or into the sidewall 328 at the interface between the middle portion 336 and the upper and lower portions 332, 334, respectively. FIGS. 6-8 illustrate the interface and methods of bonding the middle portion 336 to the lower portion 334 and/or the upper portion 332 of the sidewall 328.

Any of the features, components, and/or parts, including the arrangements and configurations thereof shown in FIGS. 5A-5C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 5A-5C.

On example of a plastic-metal interface, such as an interface between a conductive bottom portion 434 and a non-conductive middle portion 436, is shown in FIG. 6. In at least one example, the bottom portion 434 can include titanium and the middle portion 436 can include a polymer material. In one example, polymer material can include polybutylene terephthalate (PBT) including glass filled PBT. As shown, the titanium material of bottom portion 434 can be treated to form enhanced polymer-Ti bonding at the interface.

In at least one example, surface features including nano-pores and protrusions 454 can be present and the polymer can flow into and around the pores and protrusions during formation to increase the bonding therebetween. In at least one example, an etching treatment can be carried out to form the features 454 shown in FIG. 6. In at least one example, the etching treatment can include etching with sulfuric acid to form roughened macro-pockets or features in the titanium substrate of the bottom portion 434. Also, an oxide layer can be formed using a sodium hydroxide oxidation step resulting in the nano-pores and protrusions 454 shown in FIG. 6.

Figure 7A:
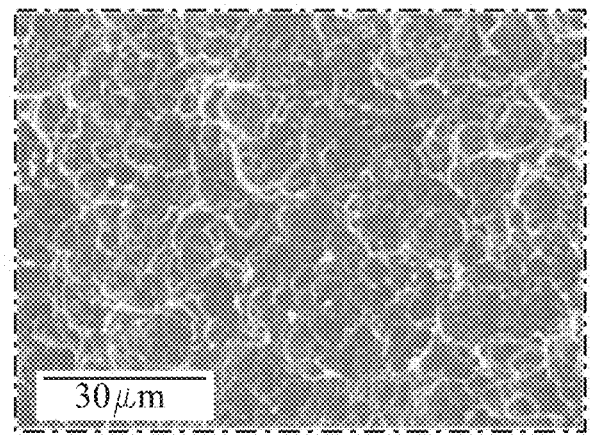
FIG. 7A shows another view of the interface of FIG. 6.
Figure 7B:
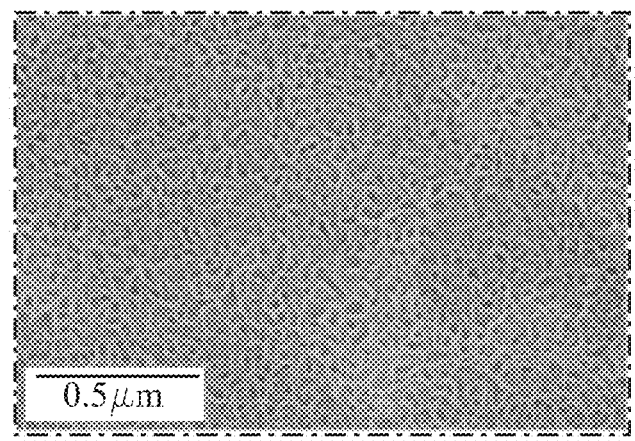
FIG. 7B shows another view of the interface of FIG. 6.
Figure 7C:
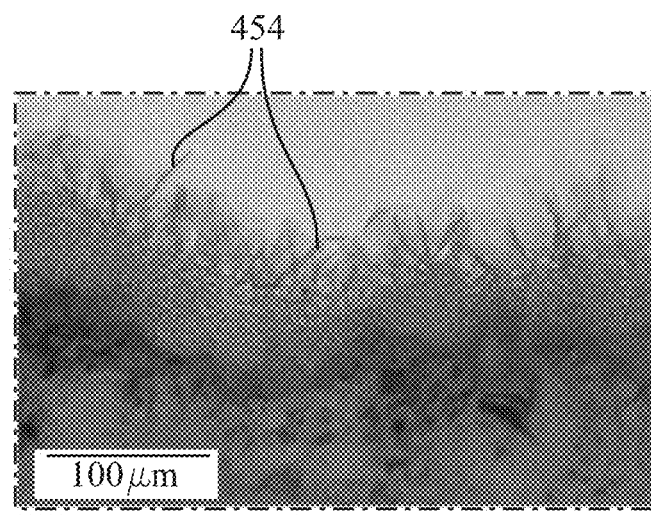
FIG. 7C shows another view of the interface of FIG. 6.
Figure 8:
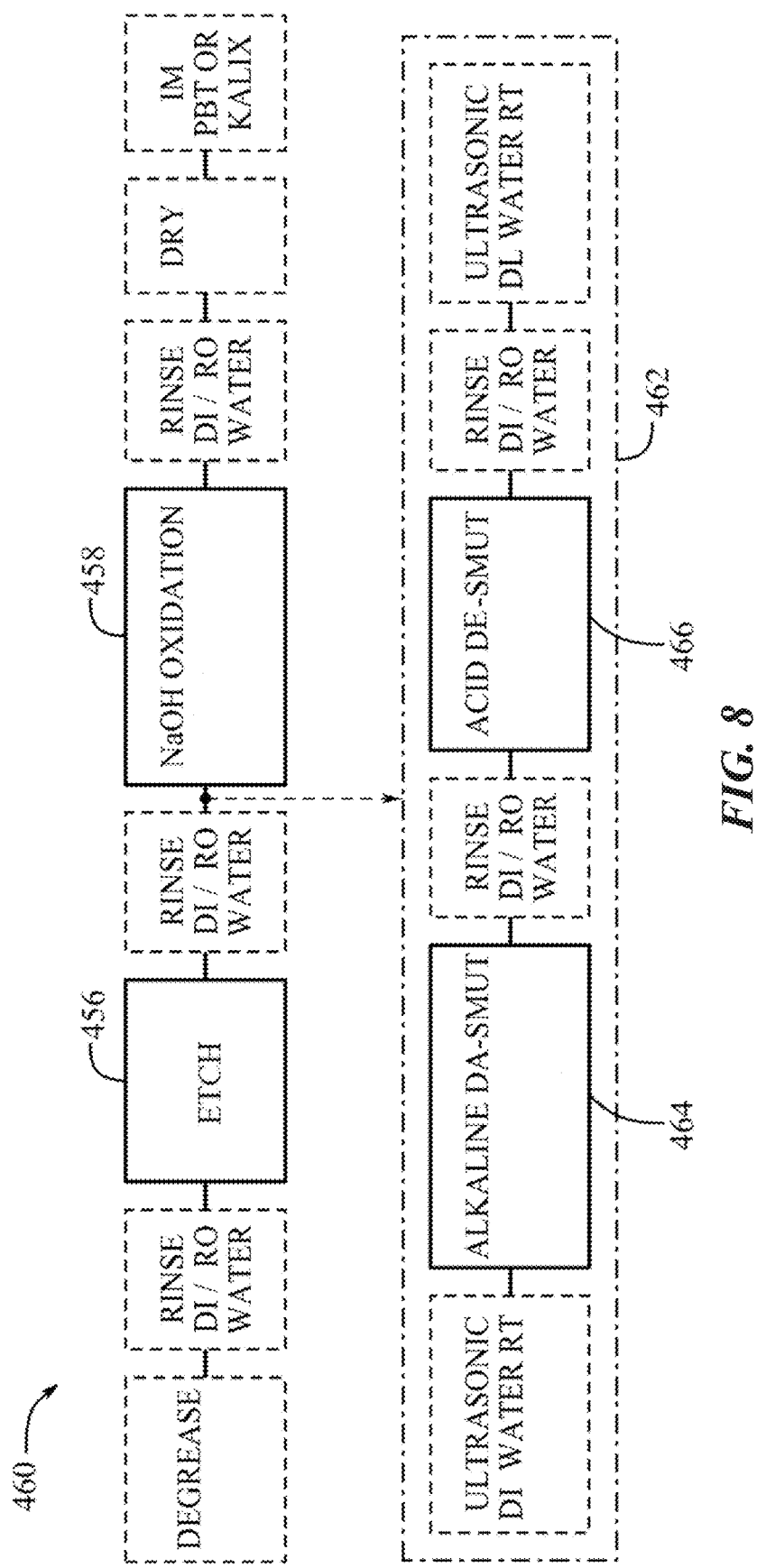
FIG. 8 shows a method of bonding a metal substrate to a non-metal substrate.

Along these lines, FIGS. 7A-7C show images of the bottom portion 434 at various stages of the process described above, including a 1,000× SEM image of an acid etched surface in FIG. 7A. FIG. 7B shows a 50,000× SEM image of an oxide surface with uniform oxide formation exhibiting plate-like morphology. FIG. 7C shows a layered double hydroxide interface including protrusions 454, similar to those illustrated in FIG. 6, into and around which the plastic polymer material of the middle portion 436 can flow and interlock with the metal material of the bottom portion 434 for enhanced bonding, as described above.

FIG. 8 shows a flowchart of an example of a method 460 of forming the interface shown in FIGS. 6-7C. In at least one example, a step 456 includes the sulfuric acid etching step noted above and another step 458 includes the sodium hydroxide oxidation step noted above. In at least one example of the method 460, between steps 456 and 458, a de-smutting method 462 can be carried out to de-smut the surface. In at least one example of the de-smutting method 462 shown in FIG. 8, a step 464 can include an alkaline de-smut, for example using sodium hydroxide (NaOH) and another step 466 can include an acid de-smutting step, for example using nitric acid (HNO3).

Any of the features, components, and/or parts, including the arrangements and configurations thereof shown in FIGS. 6-8 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 6-8.

Figure 9A:
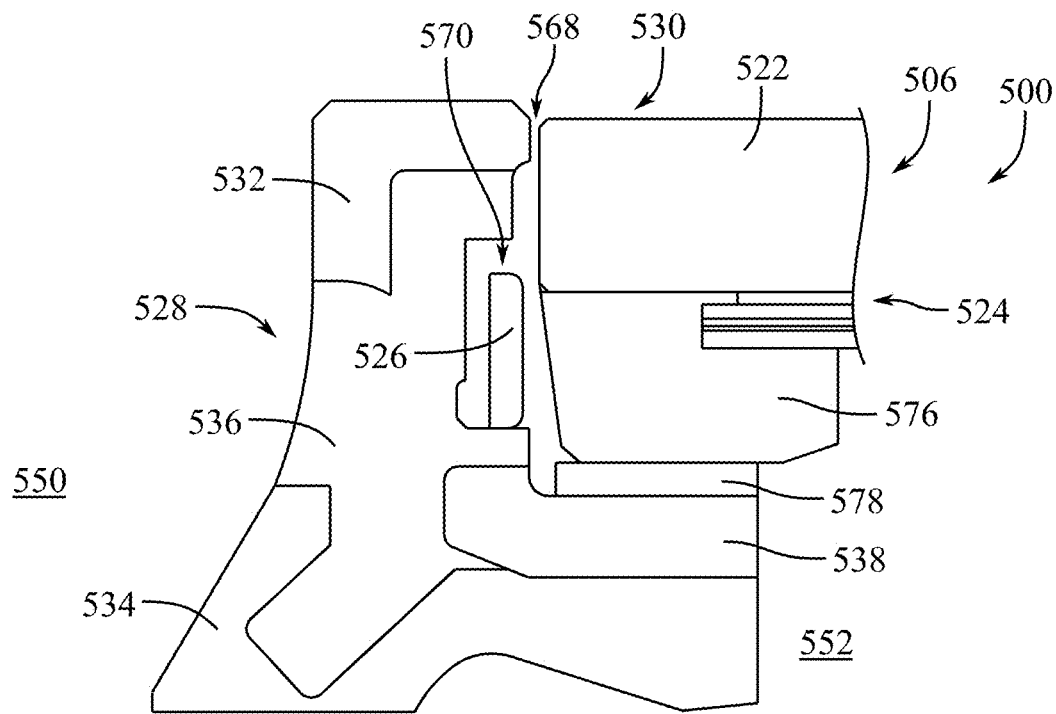
FIG. 9A shows a cross-sectional view of a sidewall and internal components of an example of a wearable electronic device.
Figure 9B:
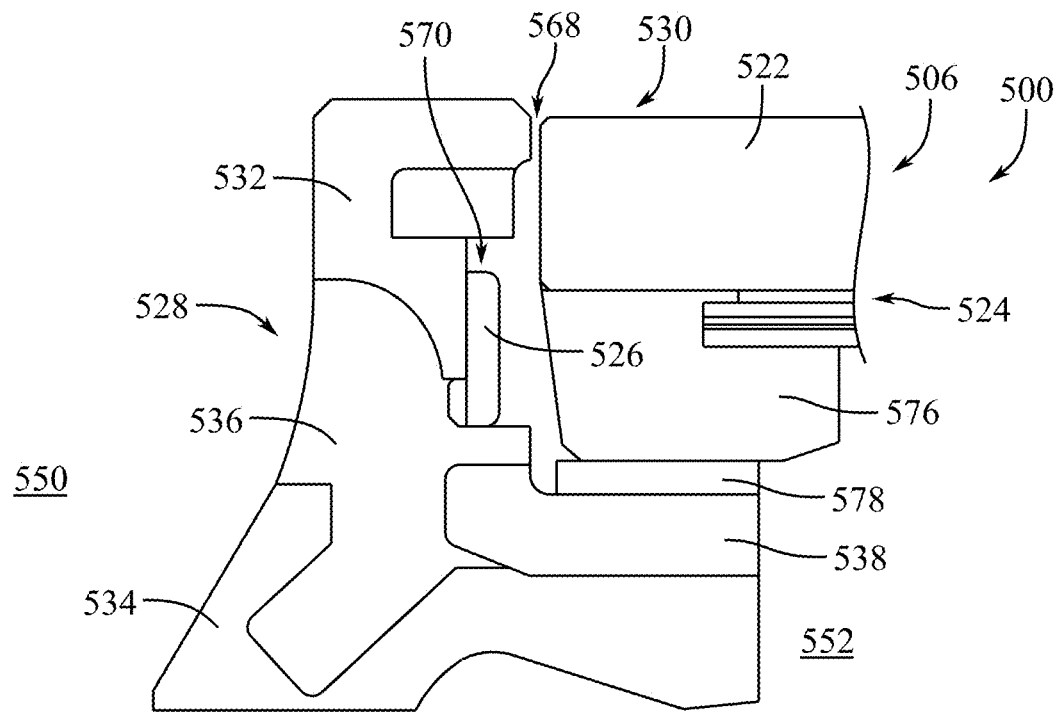
FIG. 9B shows another cross-sectional view of a sidewall and internal components of an example of a wearable electronic device.
Figure 9C:
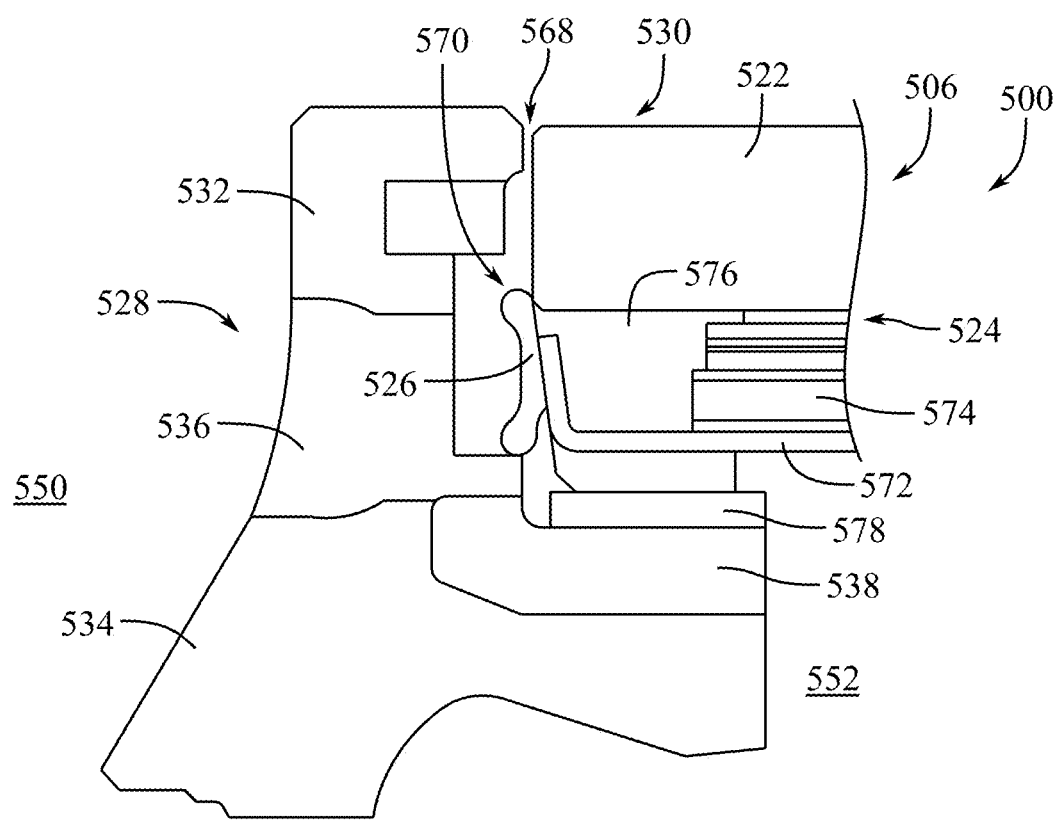
FIG. 9C shows another cross-sectional view of a sidewall and internal components of an example of a wearable electronic device.

FIGS. 9A-9C illustrate a cross-sectional view of a device 500 similar to FIGS. 5A-5C but with a display assembly 506 disposed in the opening 530 formed by the sidewall 528. In at least one example, the display assembly 506, which includes the display cover 522 and one or more other display layers 524 disposed below the display cover 522, can be disposed in the opening 530 such that a gap 568 is formed between the display assembly 506 and the sidewall 528. The gap 568 can be understood as a space between the display assembly 506, or the display cover 522 thereof, and the sidewall 528, or upper portion 532 thereof, wherein the display cover 522 does not contact the sidewall 528. In at least one example, an upper surface of the display cover 522 can be flush with, or disposed lower than, an upper surface of the upper portion 532.

In at least one example, a cavity 570 is formed in which the wave ring 526 is disposed. The cavity can be defined by the sidewall 528, including the upper portion 532 and the middle portion 536, the epoxy component 538, and the display assembly 506 or at least the display cover 522 thereof. In at least one example, the cavity can also be defined by an insulating material 576 disposed between the display assembly 506 and/or display cover 522 thereof and the epoxy component 538. One or more other components, including an antenna layer 578 or other layers. As noted above, the epoxy component 538 can bond to other layers and components, including the antenna layer 578, middle portion 536, lower portion 534, and/or the insulating material 576 to prevent moisture from entering the internal volume 552 from an external environment 550 of the device 500, such that any moisture or fluids entering the cavity 570 through the gap 568 do not continue on into the internal volume 552. In this way, the cavity can be fluid-tight.

FIGS. 9A, 9B, and 9C show cross-sectional views at various locations around the sidewall 528 to illustrate how the wave ring 526 disposed in the cavity 570 can contact the upper portion 532 of the sidewall 528 at one or more locations along a length of the wave ring 526, as shown in FIG. 9B, and contact an electrical contact 572 on the other side of the cavity 570 at one or more other locations along the length of the wave ring 526, as shown in FIG. 9C.

Accordingly, in at least one example of the present disclosure, the housing sidewall 528 can define an opening 530 and a display component, such as the display cover 522, can be disposed in the opening 530 to form the gap 568 between the housing sidewall 528 and the display component. In at least one example, the cavity 570 is defined by the sidewall 528 and the display cover 522 with the cavity 570 in fluid communication with the external environment 550 through the gap 568. In at least one example, the epoxy component 538 at least partially defines the cavity 570 and can be in direct contact with the housing sidewall 528.

In at least one example of the electronic device 500, the housing sidewall 528 has an upper sidewall portion 532 and a lower sidewall portion 534 bonded to a middle sidewall portion 536 disposed between the upper and lower sidewall portions 532, 534, respectively. The housing can define the opening 530 and the display assembly 506 can be disposed in the opening 530 to form the gap 568 between the housing and the display assembly 506. Also, in at least one example, the epoxy component 538 can serve as a seal disposed underneath the display assembly 506 and extend laterally across the gap 568 with the epoxy component seal 538 bonded directly to the middle portion 536 of the sidewall 528.

In at least one example of the present disclosure, the electronic device 500 can include the sidewall 528 defining the internal volume 552 and the opening 530. In at least one example, the sidewall 528 can include an upper portion 532, a lower portion 534, and a middle portion 536 disposed between and bonded to the upper portion 532 and the lower portion 534. The device 500 can also include the display cover 522 disposed in the opening 530 and defining the internal volume 552, the side cavity 570 defined by the display assembly 506 and the sidewall 528, with the cavity 570 in fluid communication with an external environment 550 through the gap 568 formed between the display assembly 506 and the sidewall 528, and an epoxy layer 538 contacting the lower portion 534 and the middle portion 536, and at least partially defining the cavity 570.

As noted above and as shown in FIGS. 9A-9C, the device 500 can include the epoxy component 538 at least partially disposed between the display cover 522 of the display assembly 506 and the lower portion 534, or between one or more other components of the display assembly 506, including the display layers 524, and the lower portion 534. One or more other components can also be disposed or stacked between the epoxy component 538 and the display assembly 506 or cover 522, for example the antenna layer 578. In addition, as shown in FIG. 9C, one or more examples of the device 500 can include an insulating material 576. The insulating polymer 576 can include and support a printed circuit board (PCB) 574 disposed in the internal volume 552.

Any of the features, components, and/or parts, including the arrangements and configurations thereof shown in FIGS. 9A-9C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 9A-9C.

As noted above, FIGS. 9A, 9B, and 9C show cross-sectional views at various locations around the sidewall 528 to illustrate how the wave ring 526 disposed in the cavity 570 can contact the upper portion 532 of the sidewall 528 at one or more locations along a length of the wave ring 526, as shown in FIG. 9B. Accordingly, in at least one example, the middle portion 536 can include gaps or windows through which columns or other portions of the upper portion 532 of the sidewall 528 are exposed through the middle portion 536 such that the wave ring 526 can contact the upper portion 532 directly, as shown in FIG. 9B. Also, the wave ring 526 can contact an electrical contact 572 on the other side of the cavity 570 at one or more other locations along the length of the wave ring 526, as shown in FIG. 9C. The electrical contact 572 can extend through the insulating material 576 and electrically connect to the PCB 574. In this way, the upper portion 532 of the sidewall 528 can be electrically connected to the PCB 574 through the wave ring 526. While the contact between the wave ring 526 and the electrical contact 572 is shown in FIGS. 9A-9C (as well as in FIGS. 12 and 13 below) as resulting from an undulation or circumferential variation (or wave) in the wave ring 526, the electrical contacts can be made by any number of discrete or continuous geometries such as indents or protrusions on the wave ring 526, or by discrete or continuous protrusions on the housing. According to this example, any number of mating geometries can be used between the wave ring 526 and the housing.

In at least one example, the upper portion 532 of the sidewall 528 can be electrically isolated from the lower portion 534 via the intermediary and non-conductive middle portion 536. In this way, the upper portion 532 can be a resonating element of an antenna of the device 500 with the lower portion 534 of the sidewall 528 acting as an electrical grounding plane relative to the resonating plane of the upper portion 532. As noted above, the upper portion 532 can be electrically connected to the PCB 574 of the device 500 such that signals received and sent by the resonating upper portion 532 can be directed to the PCB 574 and can be processed with one or more processors or other electronic components of the device 500, including any processors or other electronic components mounted on the PCB.

The wearable electronic devices described herein can include antennas configured to send and receive electromagnetic signals during use. Incorporating effective antennas into small, compact devices such as wearable electronic watches can be challenging because the greater the distance between a resonating plane and a grounding plane of an antenna, among other factors, the better the performance of the antenna will be. However, space is often limited to create the required Z-distances necessary in compact wearable electronic devices. In devices described herein, the housing and sidewalls of the device can be electrically separated into multiple portions to create resonating elements and grounding elements of an antenna with sufficient separation (Z-distance) therebetween for the housing itself to act as an antenna. However, this design has its own challenges, including electrically connecting the resonating element to a PCB, processor, or other electronic device without reducing the Z-distance of the antenna. Wearable electronic devices described herein are configured to overcome these challenges.

Figure 10A:
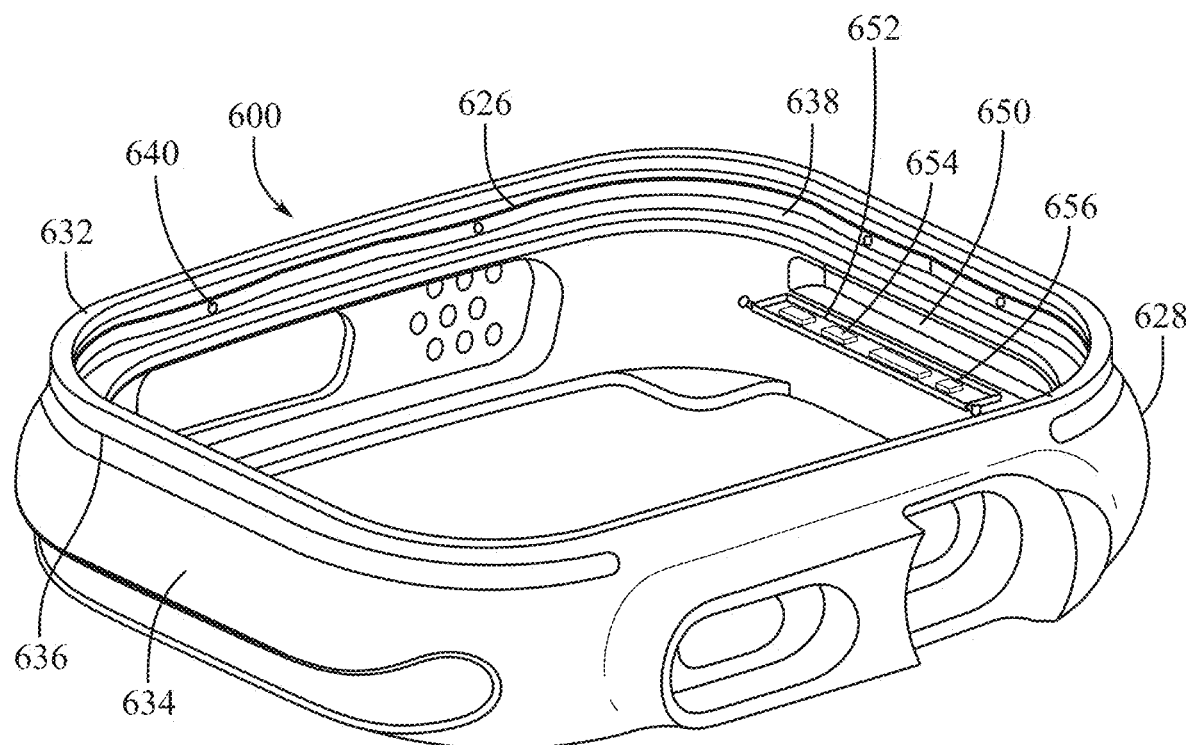
FIG. 10A shows a top perspective view of a housing sidewall of an example of an electronic device.
Figure 10B:
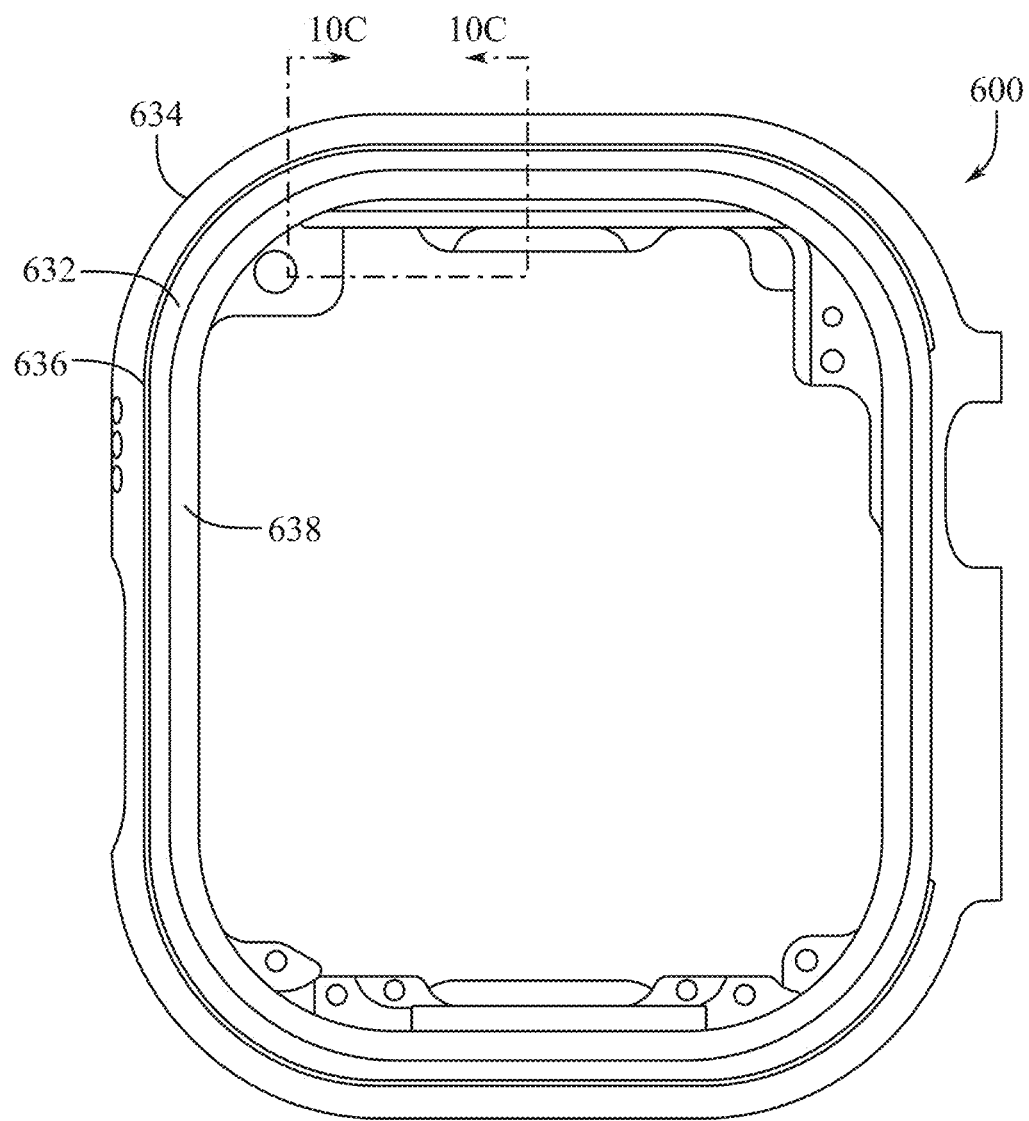
FIG. 10B shows a top view of the housing sidewall of FIG. 10A.

Along these lines, FIGS. 10A and 10B show a top perspective view and a top view, respectively, of a subassembly of a device 600, according to the present disclosure. The subassembly includes housing sidewall 628 that includes the upper portion 632, lower portion 634, and middle portion 636 separating the upper portion 632 from the lower portion 634. As noted above, the upper portion 632 and the lower portion 632 can include electrically conductive material and the middle portion 636 can include electrically insulating or non-conductive material such that the upper portion 632 of the sidewall 628 forms a resonating element of an antenna separated by a distance in the vertical or "Z" direction (or a "Z-distance") relative to the electrical grounding plane of the lower portion 634.

Figure 10C:
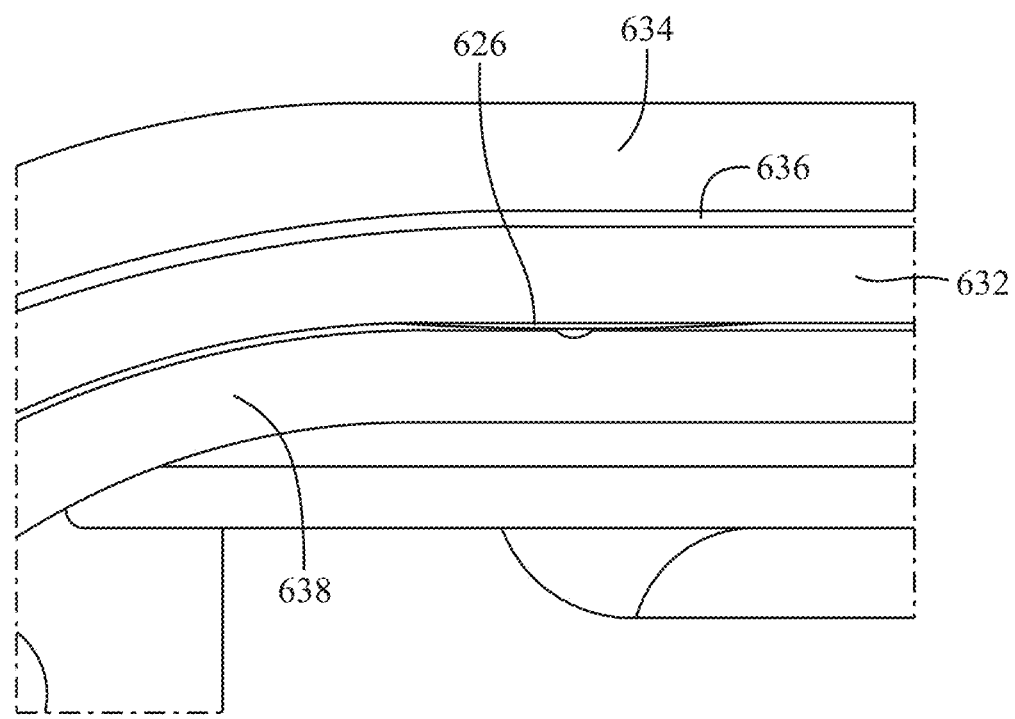
FIG. 10C shows a close up top view of a portion of the housing sidewall of FIG. 10A.

The epoxy component 638 can also be bonded to an inside of the sidewall 628 and to the middle portion 636 and the lower portion 634. In addition, the wave ring 626 is also shown in FIG. 10A. A close-up view of the subassembly from a top view is shown in FIG. 10C, with the close-up region indicated in FIG. 10B, to illustrate a portion of the wave ring 626 extending away from the sidewall 628 to make contact with an electrical contact in the internal volume of the device. As shown in FIG. 10B, the interior portion of the wave ring 626 includes a number of dimples or protrusions 640 configured to engage electrical contacts 572 that can extend through the insulating material 576 and electrically connect to the PCB 574 (as shown in FIG. 9C). As noted above, in addition or alternative to the protrusions 640 on the wave ring 626, protrusions can be formed on the housing to facilitate or ensure a secure connection between the wave ring 626 and the electrical contacts 572.

FIG. 10A also illustrates a cutout 650 formed in the inner surface of the housing sidewall 628. As shown, the cutout 650 extends into the housing sidewall 628 below the middle portion 636 and the epoxy portion 638. According to one example, the cutout 650 is formed by machining or otherwise removing a slot of the housing sidewall 628 to create a cavity on the upper portion of the interior volume, prior to assembly of the device 600. As shown, the cutout 650 provides for additional volume within the housing sidewall 628 that can be used for connections or other housings. According to one example, the cutout provides an isolated volume where component connections can be made, such as for microphones or pressure sensors that are typically located near the exterior of the device 600, without consuming valuable interior volume. In one example, board to board connections, such as hot-bar soldering, can be performed on the main PCB within the main cavity, and a flexible cable can then extend from the main PCT to the cutout 650 formed in the inner surface of the housing sidewall 628. Within the cutout 650, according to one example, a tray 652 that can be fastened to the housing can include a circuit board 654 with any number of components 656, such as connectors, components, gyroscopes, accelerometers, etc. that can then be connected to the PCB via the flexible cable. According to this example, the transition of a number of connections to previously unused portions of the housing sidewall 628 allows for added room within the housing for additional battery volume or the inclusion of additional connectors or features on the main PCB.

Any of the features, components, and/or parts, including the arrangements and configurations thereof shown in FIGS. 10A-10C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 10A-10C.

Figure 11:
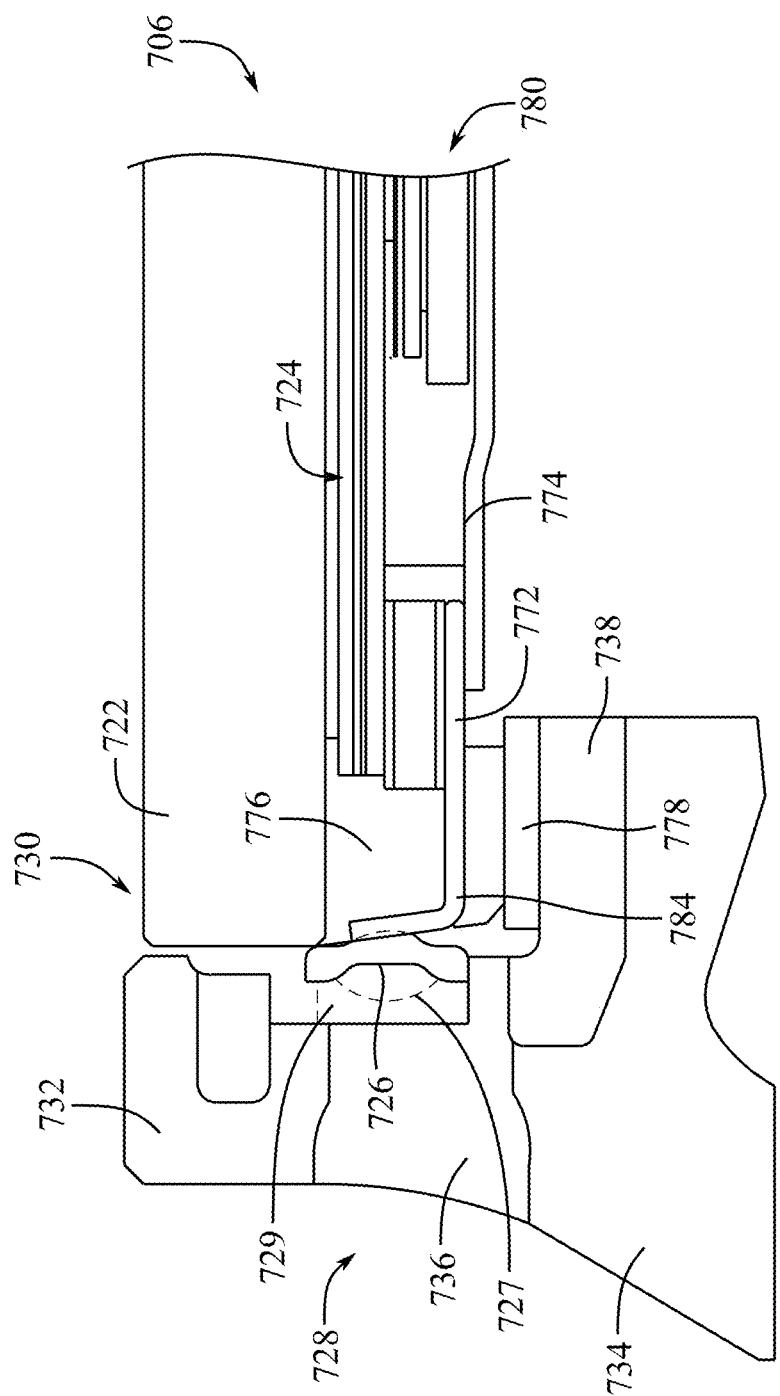
FIG. 11 shows a cross-sectional view of a sidewall and internal components of an example of a wearable electronic device.

FIG. 11 shows another cross-sectional view similar to the cross-sectional views shown in FIGS. 9A-9C, where a sidewall 728 includes an upper portion 732, a middle portion 736, and a lower portion 734. The sidewall 728 defines an opening 730 in which a display assembly 706 is disposed, the display assembly 706 including a display cover 722 and one or more other display layers or components 724. An epoxy component 738 can contact the lower portion 734 and the middle portion 736 as shown and one or more other layers or components can be stacked or disposed between the display cover 722 and the epoxy component 738, for example the Ith antenna layer 772 and the insulating material 776. In at least one example, the insulating material 776, which can also be referred to herein as a mounting component 776, can structurally support one or more other components, including the electrical contact 772 extending there through and/or the display cover 722 or other components 724 of the display assembly 706.

In at least one example, the display mounting component 776 may be formed from a molded material, such as a molded insulating material, including a polymer (e.g., a low-injection-pressure-overmolded polymer). The material that forms component 776 may be epoxy, polyurethane, and/or other polymer materials. Thermoplastic and/or thermoset polymer may be used in forming component 776. Heat and/or light (e.g., ultraviolet light) may be used in curing the polymer forming component 776. As one illustrative example, component 776 may be formed from a thermoset structural adhesive such as a one-part heat-cured epoxy. Other polymer(s) may be used, if desired. Vacuum may be applied to the interior of a mold to help draw liquid polymer into a desired shape within a mold during formation of component 776.

One or more surfaces of component 776 can serve as a reference surface (datum) that helps establish a desired physical relationship between component 776 and other portions of a device including the display assembly 706. As an example, component 776 can be attached to an opposing surface of a housing using a layer of adhesive. The shape and location of component 776 relative to display cover layer 722, display layers 724, and other structures in display 706 can help establish a desired position for display 706 relative to a device housing. The upper surface of component 776 can be molded directly to the underside of display cover 722 to help form an environmental seal. In some examples, however, the display assembly 706 can include a separate seal that can aid in forming an environmental seal between the display assembly 706 and a housing.

Figure 12:
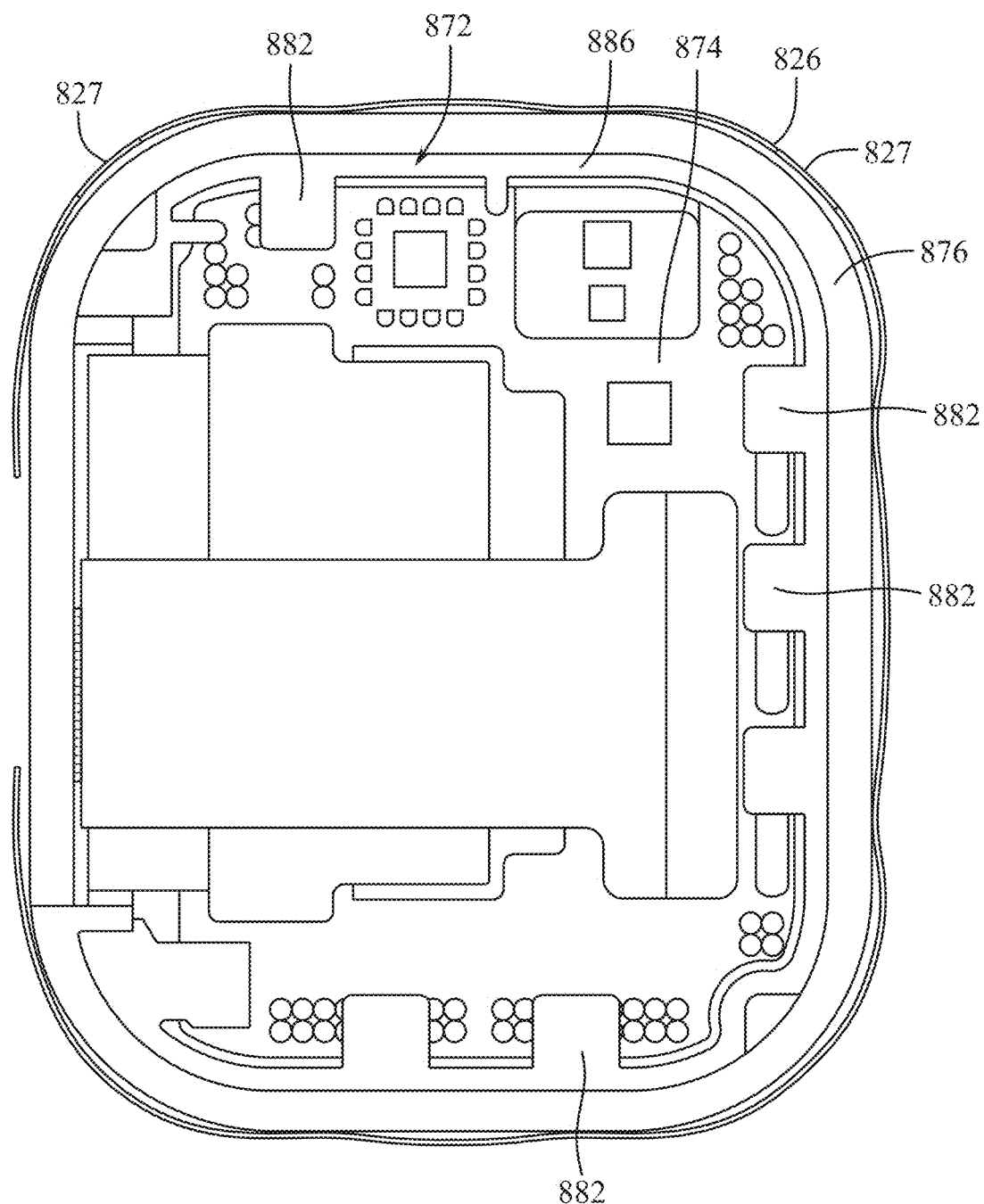
FIG. 12 shows a top view of a portion of an example of an electronic device including a printed circuit board (PCB) and surrounding electrical contacts.

The location of the display mounting component is indicated in FIGS. 11 and 12. As can be see, the display mounting component 776 extends around a periphery of the PCB 774. As the PCB 774 is smaller than the display cover 722, the molded insulating material of the display mounting component 776 may be adjacent to an edge of the PCB 774.

In some examples, however, a display assembly 706 for an electronic device can include a PCB 774 that has one or more major dimensions, such as a width and/or height, which are substantially similar to the corresponding major dimension of the display cover 722 or other components 724 of the display assembly 706. By using a PCB 774 with these dimensional relationships, a tail of the display layer 724 can be made flush with a major surface of the PCB 774 so that only a single shut-off is needed during the molding operation which can be used to form the display mounting component. Accordingly, the molded insulating material of the display mounting component 776 can be disposed on a major surface of the PCB 774 and adjacent to a periphery thereon while also at least partially surrounding the flexible tail of an associated display layers 724.

In the present example, the molded material of the display mounting component 776 can also serve to affix the display assembly 706 to the device housing sidewall 728, or at least to a component of the sidewall 728 such as the lower portion 734, and/or to provide an environmental seal between the display cover 722 and the device housing sidewall 728. In some examples, the display mounting component 776 can at least partially define an exterior surface of the device, such as at an upper surface of the upper portion 732. Thus, in some examples, a portion of the insulating molded material of the display mounting component 776 that defines the exterior surface of the device can be positioned between the display cover 722 and a sidewall 728 of the housing. Further, in some examples, the portion of the exterior surface defined by the display mounting component 776 can be substantially level, in line with, and/or flush with portion of the exterior surface defined by the housing sidewall 728 and/or display cover 722.

As noted above, in order to electrically connect the upper portion 732 of the sidewall 728, as a resonating element of an antenna, the electrical connector 772 can extend through the insulating material 776 from the wave ring 726 to the PCB 774 and the wave ring 726 can contact the upper portion 732 of the sidewall 728 at another point or location along the length of the wave ring 726, similar to that shown in FIG. 9B and described above. In this way, while the PCB 774 is disposed lower than the upper portion 732 of the sidewall 728, the upper portion 732 of the sidewall 728 can predominantly define an upper resonating plane separated from the grounding plane defined by the lower portion 734 of the sidewall 728. This increased Z-distance between the upper and lower portions 732, 734 of the sidewall 728 correspondingly increases the performance of the antenna of which the upper portion 732 forms a part, or at least forms a part of a resonating element thereof.

As illustrated in FIG. 11, the wavering 726 can vary in profile. According to one example, the wavering 726 is asymmetric in shape, placing the protrusion or dimple lower on the body so that it provides a better contact with the extension feature 784 of the electrical connector 772. In other words, due to the asymmetric profile of the wave ring 726, the dimple or protrusion sits lower in the channel formed by the sidewall 728, and can make a more secure connection to an extension feature 784 having a lower profile. Additionally, as shown in FIG. 11, the wave ring 726 can include any number of optional back dimples 727 to extend toward the wave ring 726 and towards the extension feature 784, ensuring a consistent contact therewith, as well as promoting contact with the housing. Alternatively, or additionally, the sidewall 728 can have selective protrusions or bump-outs 729 that reduce the distance between the wave ring 726 and the extension feature 784, ensuring a secure contact. Such added connection securement features can be especially beneficial in corners of the sidewall 728 where antenna feeds can be located.

Any of the features, components, and/or parts, including the arrangements and configurations thereof shown in FIG. 11 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 11.

FIG. 12 shows a top view of a subassembly of a device according to the present disclosure, including a wave ring 826, insulating material 876, electrical contact 872, and PCB 874, which can be similar or part of any of the devices, systems, or subassemblies described herein with reference to other figures. As shown in FIG. 12, portions of the wave ring 826 can be selectively overmolded 827 or otherwise insulated in areas where metal on metal contact with the housing is not desired, such as where plastic to metal housing interlocks may occur. In the illustrated example of FIG. 12, the electrical contact 872 forms a singular unitary piece extending around the PCB 874 with discrete connection points 882 extending onto and contacting the PCB 882 or electrical circuits/pathways or other components of or on the PCB 882.

Any of the features, components, and/or parts, including the arrangements and configurations thereof shown in FIG. 12 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 12.

Figure 13:
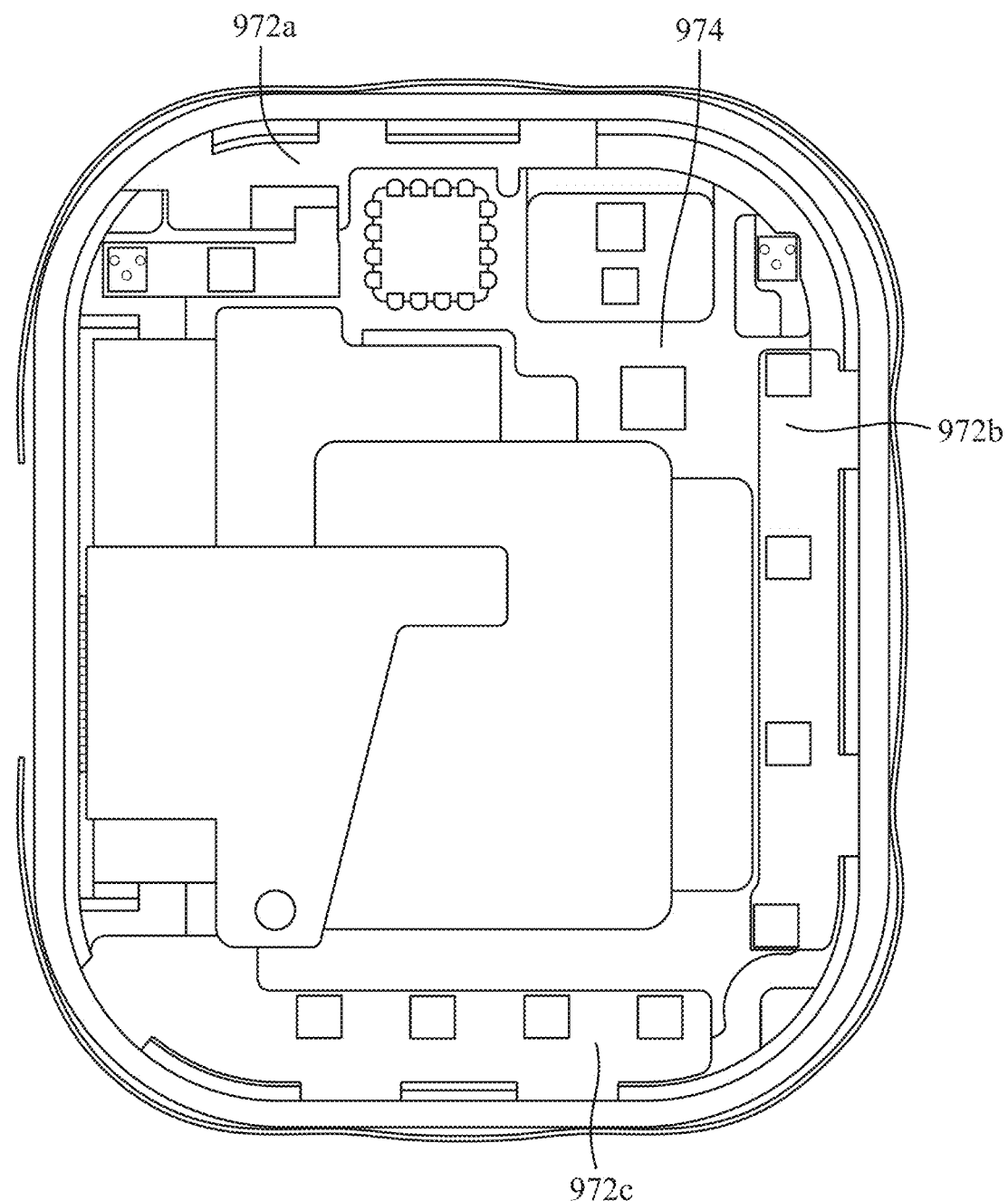
FIG. 13 shows a top view of a portion of an example of an electronic device including a printed circuit board (PCB) and surrounding electrical contacts.

FIG. 13 shows another example of top view of a subassembly similar to that shown in FIG. 12 but with multiple discrete and separate electrical connectors 972a, 972b, and 972c making contact with the PCB 974. Any of the features, components, and/or parts, including the arrangements and configurations thereof shown in FIG. 13 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 13.

In at least one example, an electronic device can include a sidewall 728 including an antenna 732, the sidewall defining an internal volume. The device can also include a PCB 774 disposed in the internal volume, an insulating material 776 disposed in the internal volume, and an electrical connector 772 contacting the PCB 774, the electrical connector 772 extending through the insulating material 776 and forming an electrical contact between the antenna 732 and the PCB 774.

In one example, the device can include a conductive housing sidewall 728 defining an internal volume, a PCB 774 disposed in the internal volume, an electrical connector 772 contacting the PCB 774 and extending through the insulating material 776, and an elongate conductive member 726 (also referred to herein as the wave ring 726) disposed between the housing sidewall 728 and the electrical connector 772, the elongate conductive member 726 contacting the electrical connector 772 and the housing sidewall 728.

In one example, an electronic device can include a housing sidewall 728 including a lower portion 734 and an electrically conductive upper portion 732 separated from the lower portion 734 by a non-conductive material 736, the housing sidewall 728 defining an internal volume and an opening 730, a display component 722 disposed in the opening 730, a PCB 774 disposed in internal volume below the display component 722, an insulating material 776 disposed in the internal volume between the housing sidewall 728 and the PCB 774, and a connector 772 forming an electrical pathway between the upper conductive portion 732 of the sidewall 728 and the PCB 774. In such an example, the upper portion 732 can form a ring surrounding a periphery of the display component 722.

In at least one example, the insulating material 776 is molded to the electrical connector 772. In one example, as shown in FIG. 12, the insulating material 776 can include a continuous member extending around a periphery of the PCB 774. Similarly, in at least one example, the insulating material 776 can form or include a closed ring disposed between the PCB 774 and the antenna 732 formed by the upper portion 732 of the sidewall 728. In one example, the elongate conductive member 726 contacts the electrical connector 772 at a first location along a length of the elongate conductive member 726 and contacts the housing sidewall 728 at a second location along the length of the elongate conductive member 726. In at least one example, the elongate conductive member 726 contacts the electrical connector 772 at a third location along the length of the elongate conductive member 726 and contacts the housing sidewall 728 at a fourth location along the length of the elongate conductive member 772.

In at least one example, the electrical connector 772 includes a continuous member 886, shown in FIG. 12, that has one or more discrete extensions features 784, as shown in FIG. 11, extending from the continuous member 886 and through the insulating material 776. The extension features 784 extend through the insulating material 776 to contact the wave ring 726 (or "elongate conductive member"), as shown in FIG. 11.

As noted above, and with reference now to FIG. 14A, an increased Z-distance between the upper portion 1032 as a resonating element of an antenna relative to the electrical ground plane of the lower portion 1034 of the sidewall 1028 can increase the performance of the antenna. In order to increase the Z-distance, the display cover 1022 of the device can include a lower beveled surface to make room for the electrical connector 1072 to extend further upward when making contact with the wave ring 1026, thus increasing the overall plane of the resonating element of the antenna above the grounding plane of the lower portion 1034 of the housing.

Figure 14A:
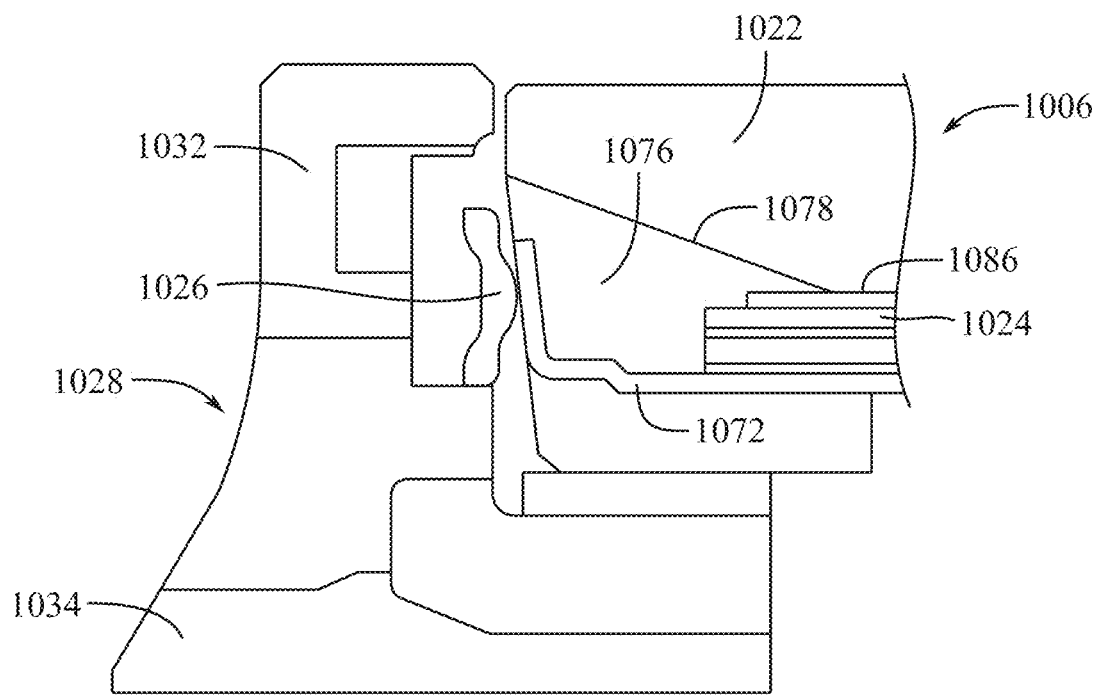
FIG. 14A shows a cross-sectional view of a sidewall and internal components of an example of a wearable electronic device.
Figure 14B:
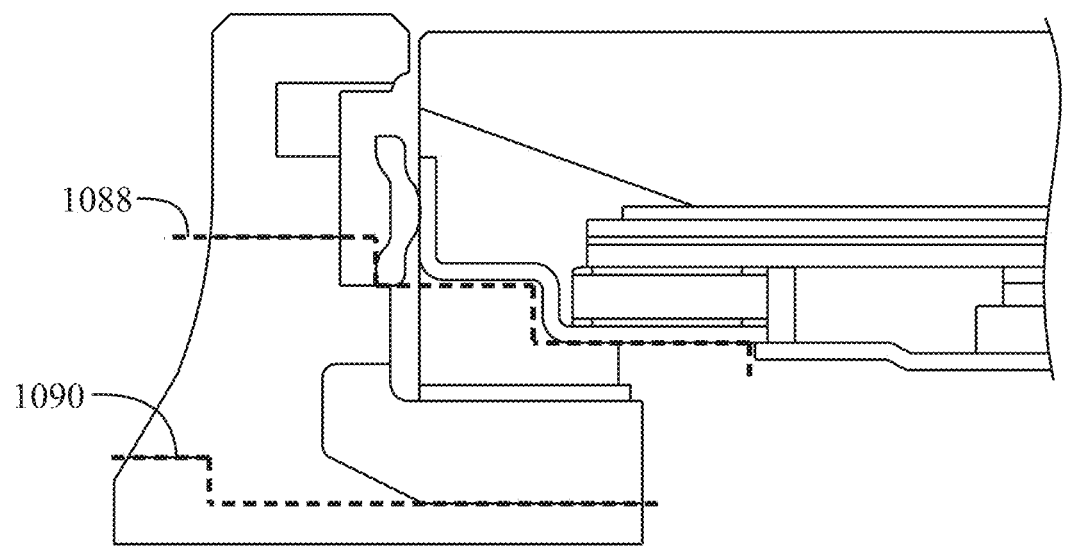
FIG. 14B shows a cross-sectional view of a sidewall and internal components of an example of a wearable electronic device.

For example, as shown in FIG. 14A, the display cover 1022 includes a lower beveled surface 1084, which provides a space for the electrical connector 1072 to make an electrical connection with the wave ring 1026, and thus the upper portion 1032 of the sidewall 1028 that contacts the wave ring 1026, further upward to increase the Z-distance. The Z-distance between the resonating plane 1088 and the grounding plane 1090 is illustrated in FIG. 14B. As shown in FIG. 14A, the electrical connector 1072 extends upward toward the display cover 1022 and into the space that would otherwise be occupied by the display cover 1022 if not for the beveled surface 1084.

The wave ring 1026 can likewise be raised to the level of contact with the electrical connector 1072 shown in FIG. 14A to raise the average height/level of the resonating plane relative to the grounding plane formed at least in part by the lower portion 1034 of the sidewall 1028. In this way, the Z-distance shown in FIG. 14B can be maximized to increase the average height/level of the resonating plane relative to the grounding plane for improved antenna performance.

In at least one example, the insulating material 1076, elsewhere referred to herein as the display mounting component, can extend into the spaced adjacent to the beveled surface of the display cover 1022 to support the display cover and other components of the display assembly 1006, including the various display layers 1024 shown. In addition, in at least one example, a mask layer that can include a PVD layer, ink layer, or other masking layer can be disposed on a lower flat surface 1086 of the display cover 1022 adjacent the beveled surface 1085. The mask can provide an aesthetic feature that reduces unwanted light scattering and reflections at the transition between the lower surface of the display cover 1022 and the beveled surface 1084. In at least one example, the mask can be between about 50 microns and 150 microns thick, for example about 100 microns thick.

Thus, in at least one example, an electronic device described herein can include a sidewall 1028 defining an opening, a display component such as the display cover 1022 disposed in the opening. The display cover 1022 can include a lower beveled edge forming a beveled surface facing the internal volume of the device. In such an example, the insulating material 1076 can contact the beveled surface of the display cover 1022 forming a beveled boundary 1078 as shown in FIG. 14A.

Any of the features, components, and/or parts, including the arrangements and configurations thereof shown in FIGS. 14A and 14B can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 14A and 14B.

Referring briefly back to the exploded view of a device shown in FIG. 2, at least one example of the device 200 can include a back cover 214 and an electromagnetically transparent component 216.

Because wearable electronic devices are in contact with the user's body during use, it can be advantageous to use the device for detecting a user's body temperature, including surface and core temperature. However, the temperature of the device and the environment in which it is used can change from moment to moment during use such that detecting the user's core temperature with a wearable device can be challenging. However, devices described herein can overcome this challenge by incorporating more than one temperature sensor in the device at different locations and applying one or more algorithms that include the temperature sensed by each sensor as an input to determine a core temperature of the user.

Figure 15A:
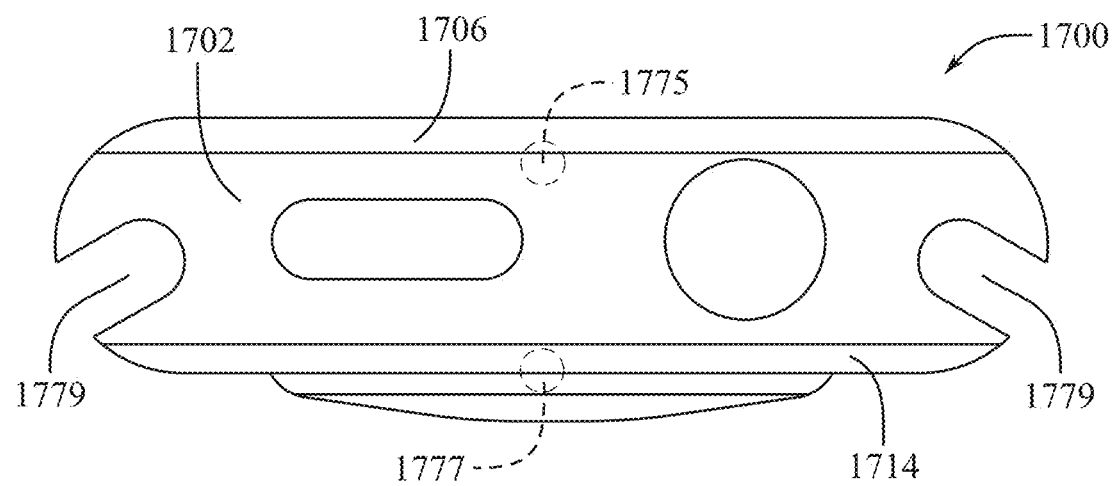
FIG. 15A shows a side view of an example of a wearable electronic device.

FIG. 15A illustrates an example of a device, for example a wearable electronic watch device 1700. In at least one example, the electronic device 1700 can include a housing 1702 defining front and rear openings, with a display component 1706 disposed at the front opening and a rear cover 1714 disposed at the rear opening. The device 1700 of FIG. 15A can also include strap retention features 1779 defined by the housing 1702 for securing a strap to the device 1700. When a strap is connected to the device 1700 via the strap retention features 1779, the device 1700 can be configured to be worn by a user, for example on the wrist of a user, with the strap securing the rear cover 1714 against the skin of the user.

In such an example, the device 1700 can be configured to detect a wrist or skin temperature of the user and extrapolate or detect/measure the user's core temperature. In order to do this, in at least one example, the device 1700 can include two or more temperature sensors on or within the device 1700. For example, a first temperature sensor 1777 can be located at, near, or adjacent the rear cover 1714, as indicated by the lower dot shown in FIG. 15A, also referred to as the bottom or lower side of the device 1700. The dot is not a representation of a sensor itself but indicates an approximate location of the first temperature sensor 1777. In addition, the device 1700 can include a second temperature sensor 1775 located at, near, or adjacent the display component 1706 on an opposite side from the first temperature sensor, also referred to as a top side of the device 1700.

In at least one example, a processor (not shown in FIG. 15A but disposed inside the device 1700) can be electrically connected to the first temperature sensor 1777 and the second temperature sensor 1775 and configured to determine a core temperature of a user based on a first temperature detected by the first temperature sensor 1777 and a second temperature detected by the second temperature sensor 1775.

FIG. 15A shows a partial cross-sectional view of the device 1700 shown in FIG. 15A to illustrate various internal components thereof. As shown, the device 1700 can include a housing 1702 defining front and rear openings and an internal volume, with a display component 1706 disposed at the front opening and a rear cover 1714 disposed at the rear opening. The internal components can include various processors, batteries, microphones, speakers, wires and electrical flexes, antennas, display components, and so forth. In addition, the internal components of the device 1700 can include a first PCB 1773 disposed near, adjacent, and above the rear cover 1714. In at least one example, the first PCB 1773 can be adhered to the rear cover 1714. The device 1700 can also include a second PCB 1774 disposed near, adjacent, and beneath the display component 1706.

Figure 15B:
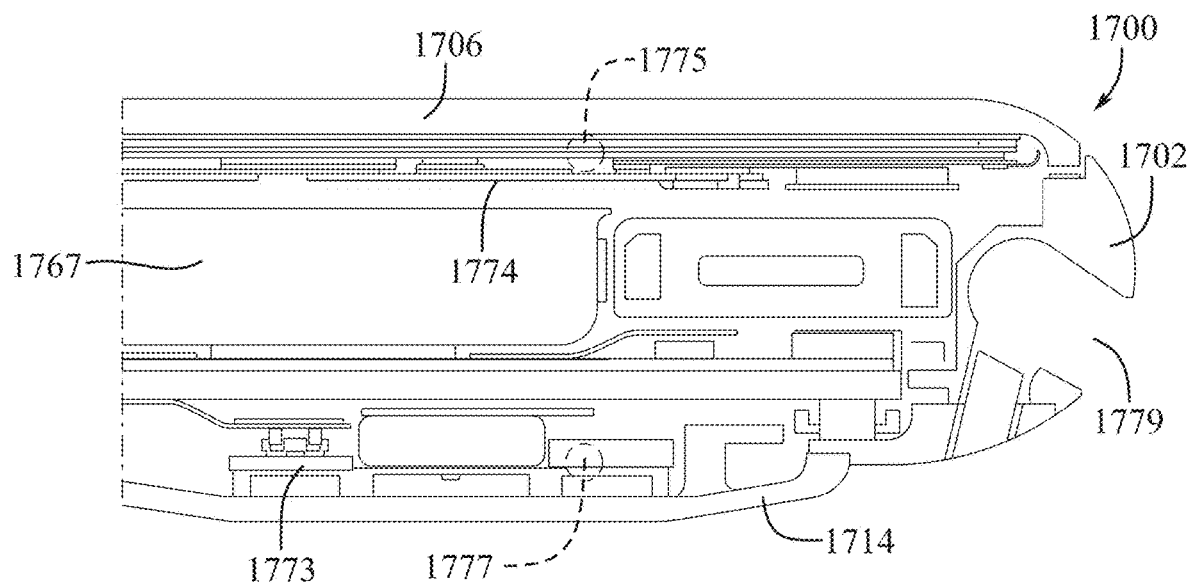
FIG. 15B shows a cross sectional view thereof.

As shown in the cross-sectional view of FIG. 15B, the first temperature sensor 1777 can be disposed on the first PCB 1773 and the second temperature sensor 1775 can be disposed on the second PCB 1774. In at least one example, one or more other electronic components, including heat generating electronic components can be disposed between the first temperature sensor 1777 and the second temperature sensor 1775 or, if not between the temperature sensors, 1777, 1775, a part of a thermal path defined from one temperature sensor to the other through one or more internal component of the device 1700. For example, a battery 1767 can be disposed within the internal volume of the device 1700 at least partially between the first temperature sensor 1777 and the second temperature sensor 1775.

While the first temperature sensor 1777 can be near the user's wrist to determine the temperature at or near the user's wrist, the device 1700 can include other internal components that may generate or absorb heat such that the system temperature of the device 1700 can affect the accuracy of the measurement of the user's wrist with the first temperature sensor 1777. Accordingly, in at least some examples, the device 1700 can include the second temperature sensor 1775 that takes into account the system temperature of the device 1700 and one or more algorithms can be used to determine the user's core temperature using measurement taken from both the first temperature sensor 1777 and the second temperature sensor 1775. In at least one example, the first temperature sensor 1777 and the second temperature sensor can be in electrical communication with one another.

In at least one example, the device 1700 can include one or more processors in electrical communication with the first temperature sensor 1777 and the second temperature sensor 1775. The one or more processors can determine the user's core temperature from measurement taken by both the first and second temperature sensors 1777, 1775 with one or more algorithms applied to the measurement to take into account the system temperature and any thermal path existing through the device 1700 and its internal components disposed therein, some of which may be disposed between the first and second temperature sensors 1777, 1775 or, if not between the temperature sensors, 1777, 1775, a part of a thermal path defined from one temperature sensor to the other through one or more internal component of the device 1700. In this way, determining the user's core temperature can be based, at least in part, on the heat generated by the heat generating components or heat absorbing component or any other components disposed in the internal volume of the device 1700.

Figure 15C:
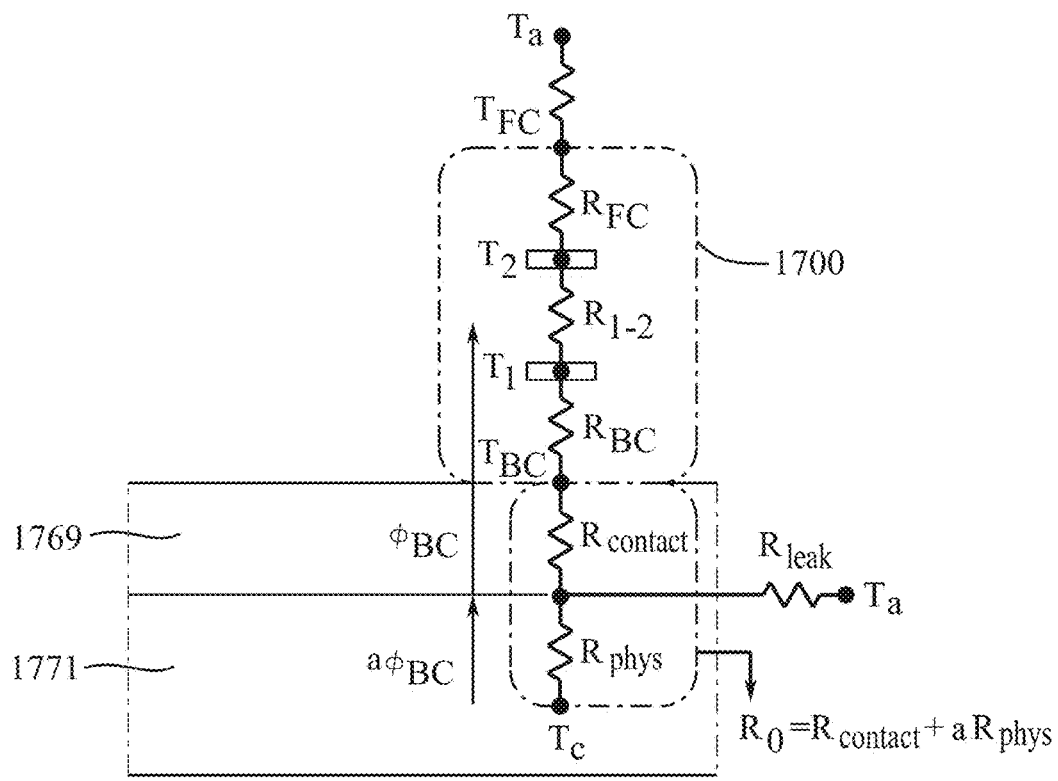
FIG. 15C shows a circuit diagram equivalent of the device shown in FIGS. 15A and 15B worn by a user.

Along these lines, FIG. 15C illustrates a circuit diagram equivalent to the device 1700 contacting a user 1771 with a contact interface shown at 1769. The illustrated diagram identifies temperature sensors $T_1$ and $T_2$, which can equate to the first and second temperature sensors 1777, 1775 shown in FIG. 15B, respectively. The heat transfer path from the user 1771, through the device 1700, and out to an external environment can be modeled as a series of resistances illustrated by resistors $R_{phys}$, $R_{contact}$, $R_{BC}$, $R_{1-2}$, and $R_{FC}$, as shown in FIG. 15C with $R_{phys}$ equating to the resistance of the user, $R_{contact}$ equating to the resistance at the contact interface, $R_{BC}$ equating to the resistance of the back cover or any other components of the device 1700 between the first temperature sensor $T_1$ (1777 in FIG. 15B) measuring temperature $T_1$ and the contact interface 1769, $R_{1-2}$ equating to any resistance in the system of the device 1700 including the thermal path between the first temperature sensor 1777 and the second temperature sensor 1775, and $R_{FC}$ equating to the resistance of the display component 1706 or any other components of the device 1700 between the second temperature sensor (1775 in FIG. 15B) measuring temperature $T_2$ and the external surface or external environment of the device 1700.

Using the modeled circuit diagram of heat flow from the wrist through the device 1700 as shown in FIG. 15C, one or more algorithms can be used to determine the core temperature of the user. For example, a first algorithm modeling the temperature $T_{BC}$ at the rear cover 1714 of the device 1700 can include:

$$T_{BC}=T_1+a_o(T_1-T_2)$$

where:

$$a_o=R_{BC}/R_{1-2}$$

An algorithm modeling a corrected temperature can include:

$$T_c=T_1+c_o(T_1-T_2)$$

where:

$$c_o=a_o+h_o$$

and where:

$$h_o=R_o/R_{1-2}$$

Furthermore, the model can also include self-heating constants (i.e., $c_1$, $a_1$, $h_1$).

In at least one example, more than two temperature sensors can be disposed in the device 1700 with measurement taken and input into one or more algorithms to determine the core temperature of the user when the device 1700 contacts the user. As noted above, in at least one example, one or more electrical and/or heat generating components can be disposed in internal volume of the device 1700 and at least partially between the various sensors or at least as part of a thermal path between the various sensors.

In at least one example, the first temperature sensor 1777 can be disposed directly against or adhered directly to the rear cover 1714 or another portion of the housing 1702 near or adjacent or in contact with the user during use. Similarly, in at least one example, the second temperature sensor 1775 can be disposed directly against, or adhered directly to, the display component 1706 or other portion of the housing 1702. In at least one example, regardless of where each temperature sensor 1777, 1775 is disposed, a thermally conductive adhesive, such as a thermally conductive pressure-sensitive adhesive, can be used to secure the temperature sensors 1777, 1775 to another component within the internal volume of the device 1700.

Any of the features, components, and/or parts, including the arrangements and configurations thereof shown in FIGS. 15A-15C can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 15A-15C.

Figure 16:
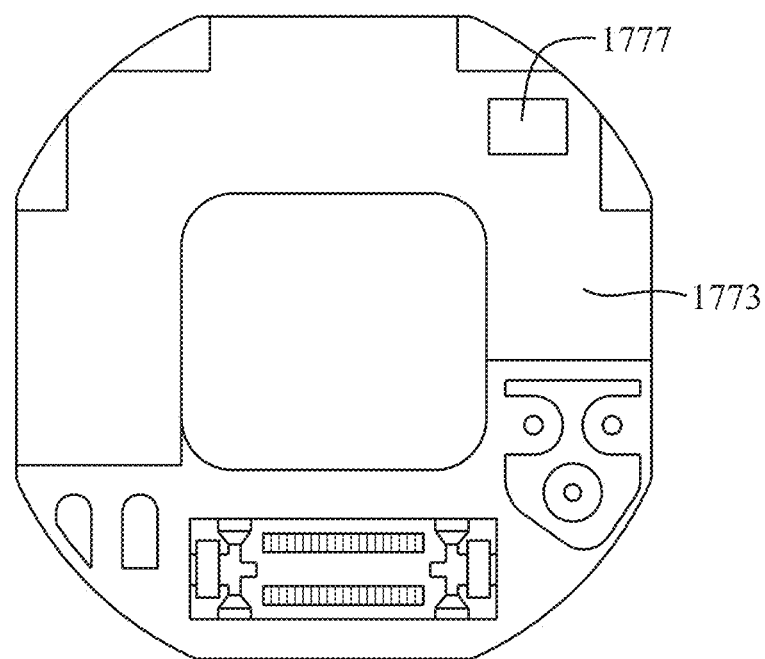
FIG. 16 shows a PCB of an example of an electronic device.
Figure 17:
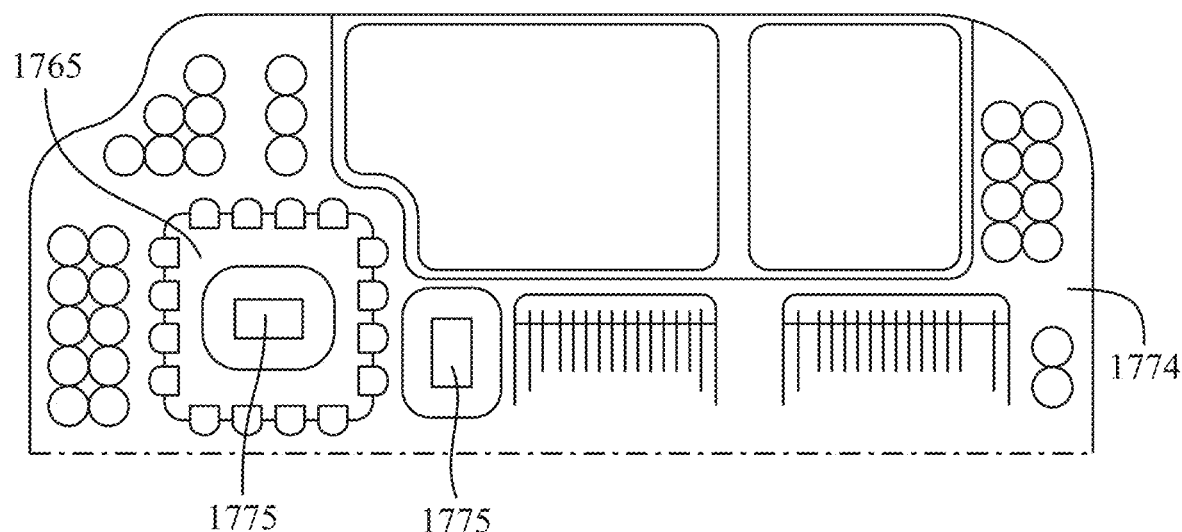
FIG. 17 shows a portion of a PCB of an example of an electronic device.
Figure 18:
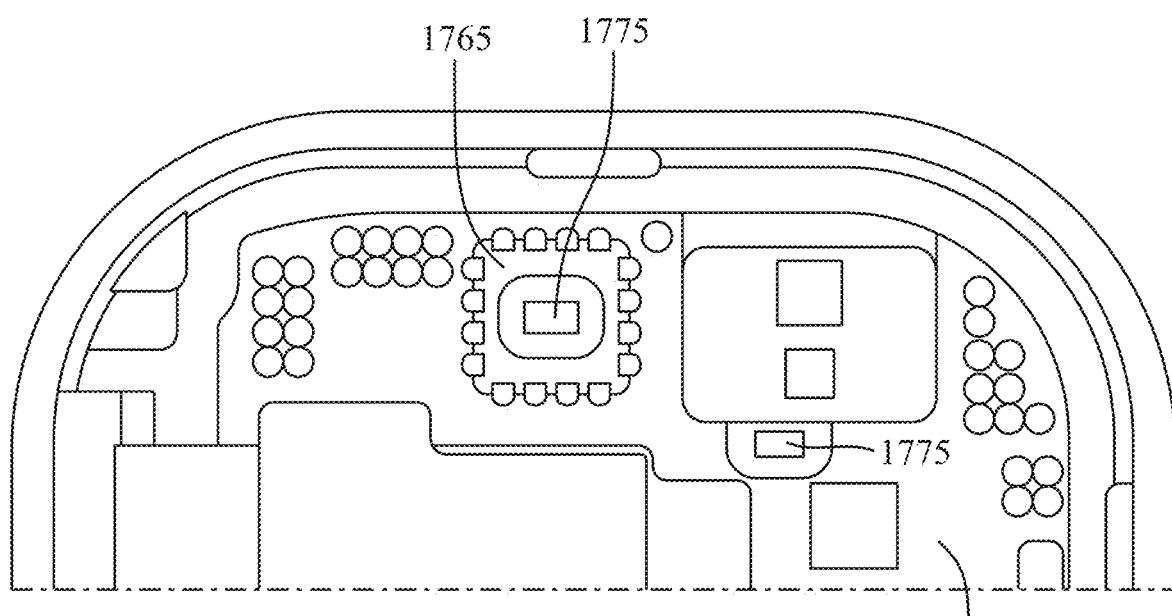
FIG. 18 shows a portion of a PCB of an example of an electronic device.
Figure 26:
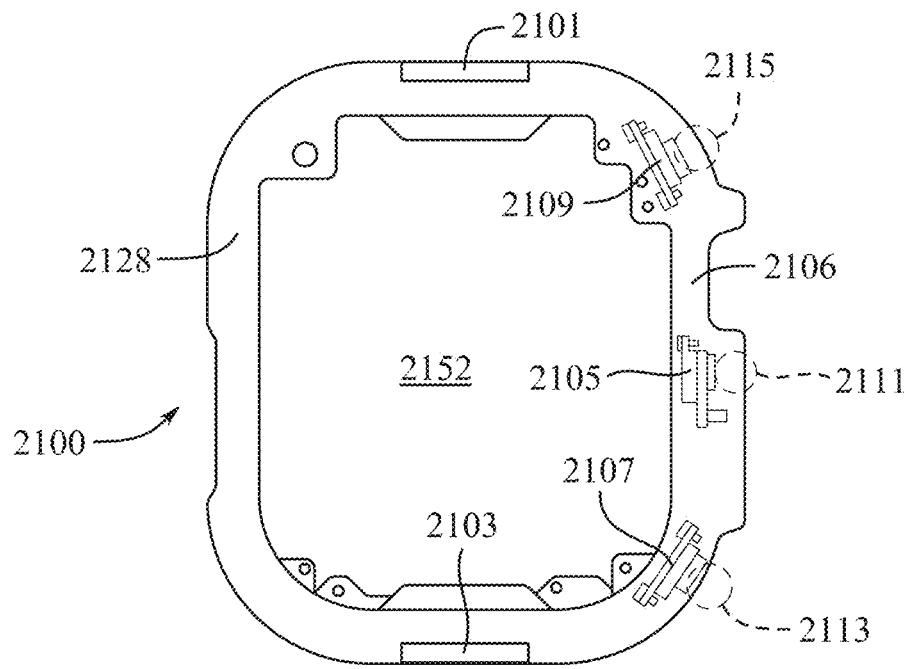
FIG. 26 shows a top view of an example of an electronic device.

FIG. 16 illustrates a PCB 1773 with an example of a location of a temperature sensor 1777. The PCB 1773 can be disposed near the rear cover 1714 similar to the first PCB 1773 shown in FIG. 15B. FIG. 26 illustrates a PCB 1774 similar to the second PCB shown in FIG. 15B that can be disposed in the internal volume of the device 1700 near the display component 1706. In the illustrated example of FIG. 17, two locations of a temperature sensor 1775 are shown where the temperature sensor 1775 can be disposed on the PCB 1774 to be at or near the display component 1706 of the device 1700. In one example shown, the temperature sensor 1775 can be disposed on the ALS module 1765. FIG. 18 shows another example of locations of the temperature sensor 1775 on an example of a PCB 1774 with one example location of the temperature sensor 1775 being on an ALS module 1765 of the PCB 1774.

In at least one example, the temperature sensors 1777, 1775 described herein can be adhered or otherwise secured to a PCB or other component, including the housing 1702 of the device 1700 without any under-fill material between the temperature sensor 1777, 1775 and the housing 1702 or PCB 1774. In at least one example, the temperature sensors 1777, 1775 can be mounted to a PCB 1774, housing 1702, or other portion of the device 1700 without any encapsulation over the temperature sensor 1777, 1775. The absence of under-fill material and/or encapsulation over the temperature sensor 1777, 1775 reduces the complexity and uncertainty of the thermal path between the sensors 1777, 1775 and/or between the sensors 1777, 1775 and the user's body or the external environment, thus simplifying the modeling and processing of the user's core temperature.

Figure 19:
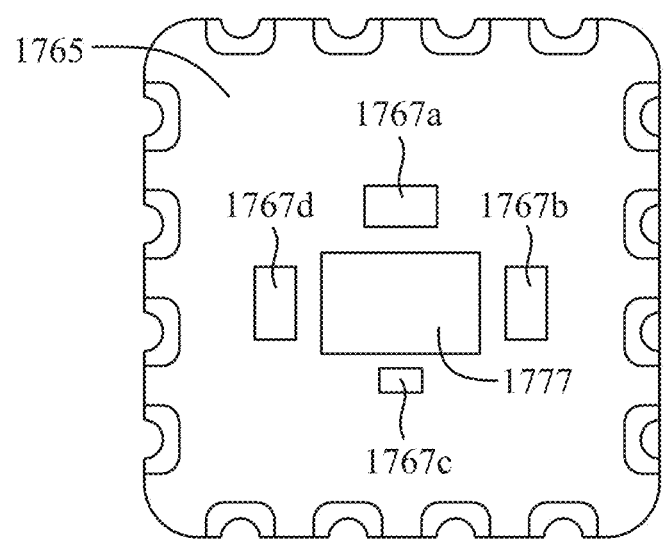
FIG. 19 shows a temperature sensor disposed on an ALS module of an example of an electronic device.

In at least one example, as shown in FIG. 19, a temperature sensor 1777 is disposed on the ALS module 1765. In at least one example, as noted above, the temperature sensor 1777 can be adhered to the ALS module 1765 using an SMT/solder or other adhesive or bonding medium without any encapsulation material disposed over and/or encapsulating the temperature sensor 1777. In such an example, in order to protect the temperature sensor 1777 from physical damage, one or more shields 1767*a*, 1767*b*, 1767*c*, and 1767*d* can be disposed around the temperature sensor 1777 such that other components are likely to come into contact with the shields 1767*a-d* before coming into contact with the temperature sensor 1777 during assembly or use. The shields 1767*a-d* can vary in number, size, position, and configuration but generally are taller than the temperature sensor 1777 such that the shields 1767*a-d* physically protect the temperature sensor 1777. In at least one example, the shields 1767*a-d* include inexpensive, non-electrically functioning or connected components. In this way, the shields 1767*a-d* can absorb contact, be dented, chipped, or otherwise physically damaged during assembly or use of the device 1700 without negatively affecting the functionality of the device 1700 and the temperature sensor 1777.

Figure 20A:
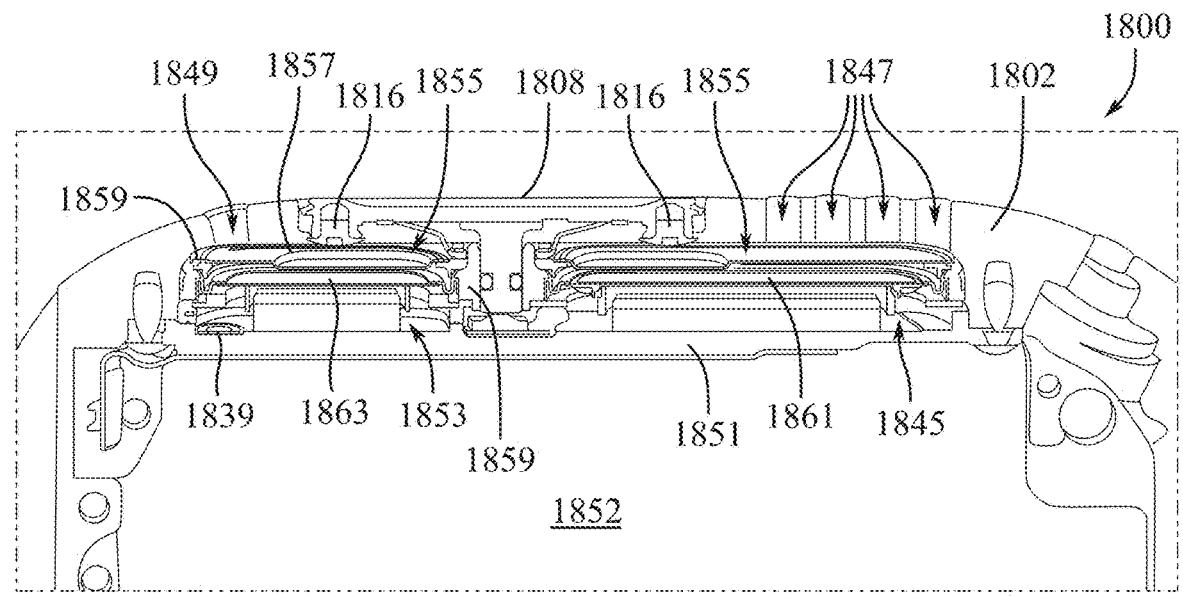
FIG. 20A shows a cross sectional view of a portion of an example of an electronic device.

In many scenarios or environments where a user may want to wear the devices disclosed herein, it may be advantageous to output high-frequency, high decibel sounds to alert others of an emergency situation such as a fall or injury to the user. These sounds or alerts can be referred to herein as siren alerts and/or sounds. In order to produce high-frequency siren sounds alongside typical lower frequency outputs for normal use, including music, voice outputs, and so forth, at least one example of a device can include a dual speaker system as shown in FIGS. 20A-21. The speaker assemblies shown herein generally include two speakers sharing a front volume but having separate back volumes associated with each speaker. Separate vents to the external environment, in addition to the separate back volumes, can enable tuning of the speaker assembly to produce clear frequencies in various high and low ranges from the various speakers in the device 1800 shown.

Any of the features, components, and/or parts, including the arrangements and configurations thereof shown in FIGS. 16-19 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 16-19.

FIG. 20A shows an example of an electronic device 1800 that includes an outer housing 1802 defining an internal volume 1852, a first speaker 1863 and a second speaker 1861 disposed in the internal volume 1852, the first speaker 1863 including a frame 1859 disposed around a periphery of a diaphragm 1857 of the first speaker 1863, a front volume 1855 defined by the outer housing, the first speaker 1863, and the second speaker 1861, a first back volume 1853 defined by the first speaker 1863 and the frame 1859, and a second back volume 1845 defined by the second speaker 1861 and the frame 1859.

In at least one example, the electronic device 1800 can include an outer housing 1802, an inner housing 1851 spaced apart from the outer housing 1802, a speaker assembly disposed between the inner and outer housings 1802, 1851. The speaker assembly can include the first speaker 1863, the second speaker 1861, and the speaker frame 1859 supporting the first speaker 1863. The device can further include the first back volume 1853 defined by the inner housing 1851 and the first speaker 1863 and the second back volume 1845 defined by the inner housing 1851 and the second speaker 1861, with the second back volume 1845 separated from the first back volume 1853 by the speaker frame 1859.

Another example of the electronic device 1800 can include the outer housing 1802, the inner housing 1851, the speaker assembly disposed between the inner and outer housings 1851, 1802 including the first speaker 1863 and the second speaker 1861. The device 1800 can also include a front volume 1855 defined by the outer housing 1802 and the speaker assembly, the back volume defined by the inner housing and the speaker assembly and separated into first and second isolated portions 1853 and 1845, respectively. In at least one example, the device 1800 can also include first vent 1849 defined by the housing 1802 through which a first end of the front volume 1855 is in fluid communication with an external environment and a second vent 1847 defined by the housing 1802 through which a second end of the front volume 1855 is in fluid communication with the external environment.

In at least one example, the front volume 1855 can be isolated from the first and second back volumes 1853 and 1845, respectively. The speakers 1863, 1861 can be disposed between the front volume 1855 and the first and second back volumes 1853, 1845 and the frame 1859 can structurally support the first speaker 1863. In at least one example, the frame 1859 forms an air-tight seal between the first back volume 1853 and the second back volume 1845. In addition, as noted above, the inner housing 1851 can at least partially define the first back volume 1853. For example, the frame 1859 can include a collar 1843 and a molded seal 1841 extending from the collar 1843 toward the internal volume 1852 and contacting the inner housing 1851 to seal the first back volume 1853 as shown behind/below the first speaker 1863. The collar 1843 can include a metal ring disposed around the speaker 1863 and configured to redirect magnetic flux around the speaker 1863. In at least one example, the speaker frame 1859 structurally supports the second speaker 1861.

In one example, the first speaker 1863 is smaller than the second speaker 1861. The first speaker 1863 can be referred to as a tweeter and be configured to output higher frequency sound waves than the larger second speaker 1861. Accordingly, to accommodate the smaller volumetric air displacement caused by the first speaker 1863, in at least one example, the first back volume 1853 can be smaller than the second back volume 1845.

Figure 20B:
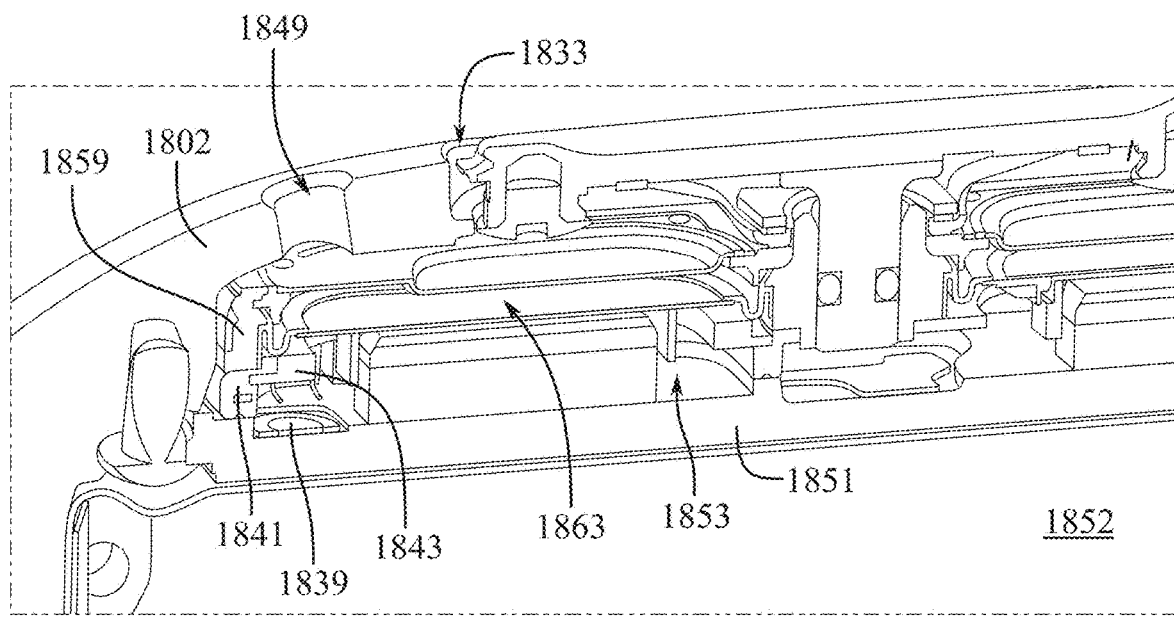
FIG. 20B shows a close up view of the portion of FIG. 20A.
Figure 21:
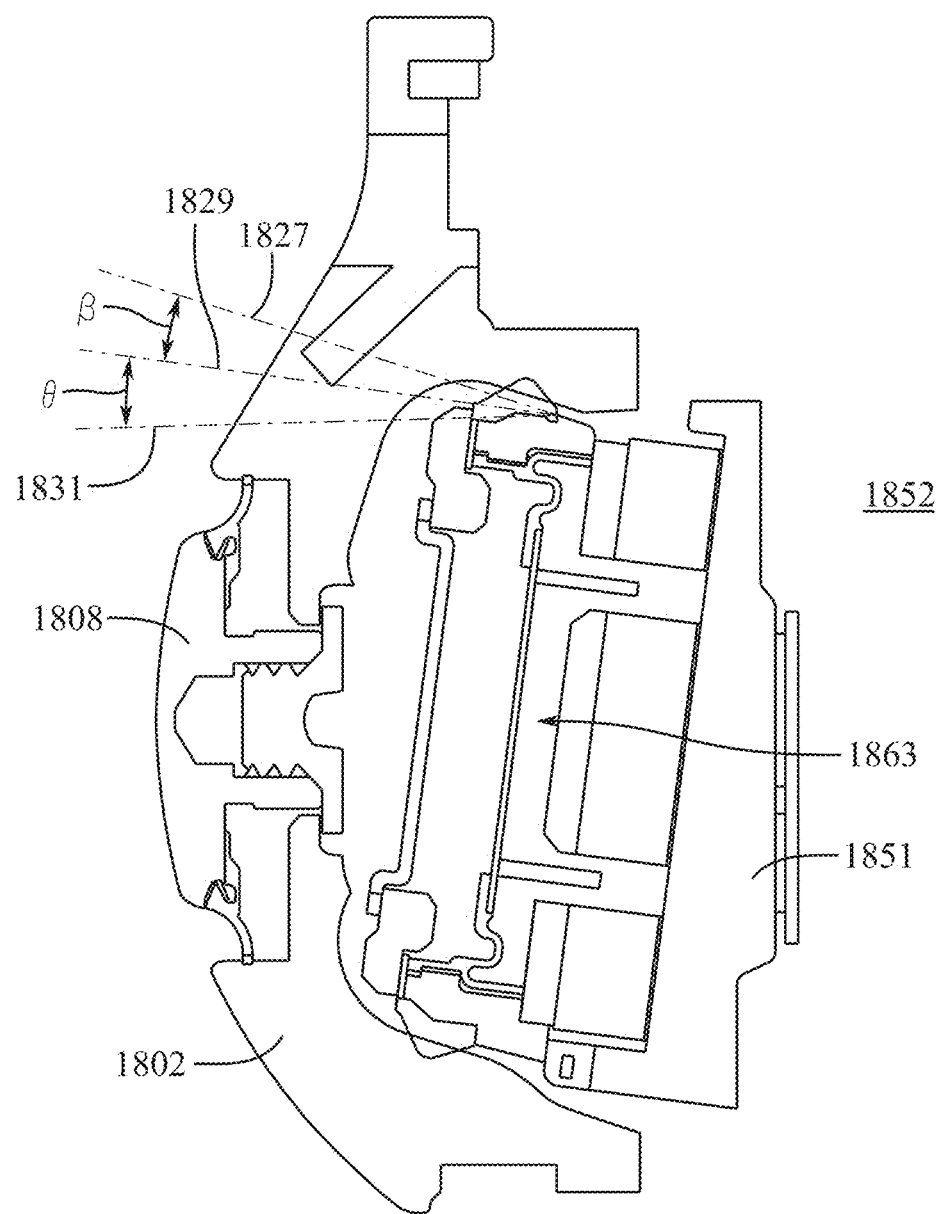
FIG. 21 shows another cross sectional view of the speaker assembly of FIG. 20E.

In at least on example, as shown in FIGS. 20A and 20B, the electronic device 1800 can also include a valve 1839 disposed in an aperture defined by the inner housing 1851 to vent air from the first isolated portion 1853 of the back volume to the internal volume 1852. In at least one example, the pressure valve 1839 can be configured to equalize pressure between the internal volume 1852 and the back volume 1853. In at least one example, the valve 1839 can include a mesh and a channel passing through and defined by the inner housing 1851.

The shared front volume 1855 can be in fluid communication with an external environment through various vents passing through the outer housing 1802. The location and configuration of each vent can be designed to accommodate high siren-type frequencies output by the smaller tweeter speaker (first speaker 1863) and lower frequencies output by the second speaker 1861. In this way, a broader range of frequencies can be output by the speaker assembly clearly and effectively.

In at least one example, the first vent 1849 is formed of a single aperture defined by the outer housing 1802. The second vent 1847 can include two or more apertures defined by the outer housing 1802. In at least one example, a distance between any two adjacent apertures of the second vent 1847 can be less than a distance between any aperture of the second vent 1847 and the single aperture of the first vent 1849.

As noted above, the arrangement and configuration of the speaker assembly of the electronic device 1800 shown in FIGS. 20A and 20B enables the speaker assembly to output frequencies in the normal range of daily use, including music, voice, and other typical audio outputs, as well as loud, high frequencies in the range of above 3 kHz, 3.5 kHz, or even above 4.5 kHz from the first smaller speaker 1863 to be used as a siren. The siren can be used in conjunction with a fall-detection system of the device 1800 to alert others if the user has fallen or been injured. During other activities, for example during mountain biking, the siren can output warning signals when coming around a blind corner on a trail or the like. A guardian mode of the device 1800 could activate the siren as an assault whistle or a mugging deterrent.

In order to fit the dual speaker assembly within a tight space between the inner housing 1851 and the outer housing 1802 of the device 1800, some of the components discussed above and shown in FIGS. 20A-20B are configured to interface with and be disposed with other component of the device 1800 to form a tight, compact, space-saving device 1800. For example, the speaker assembly shown in FIGS. 20A and 20B can be disposed within the device 1800 in generally the same location as a button of the device, such that the button and the speaker assembly share the same location or portion of the internal volume of the device 1800. In such an example, the button may include one or more components disposed between through, or with one or more components of the speaker assembly.

Figure 20C:
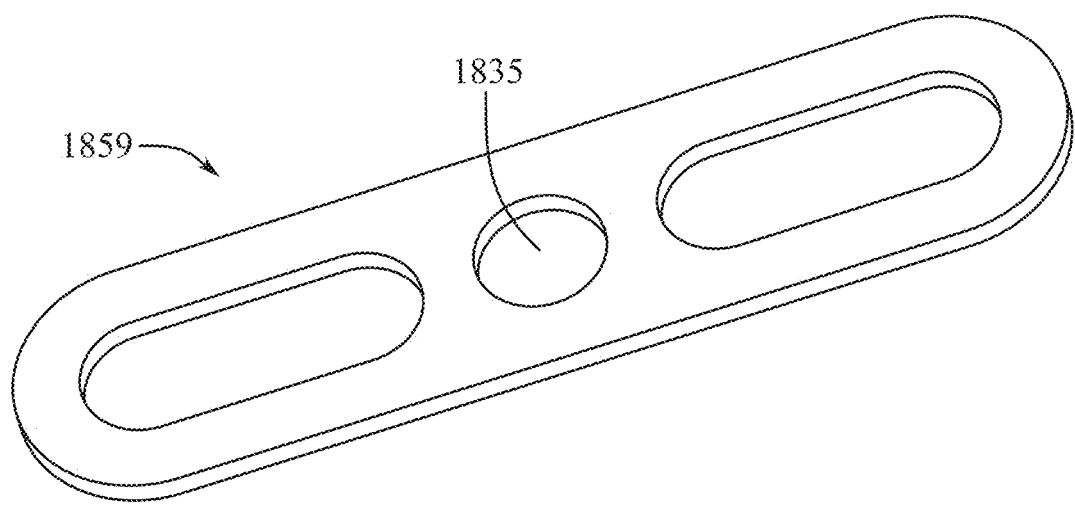
FIG. 20C shows an example of a speaker frame.
Figure 20D:
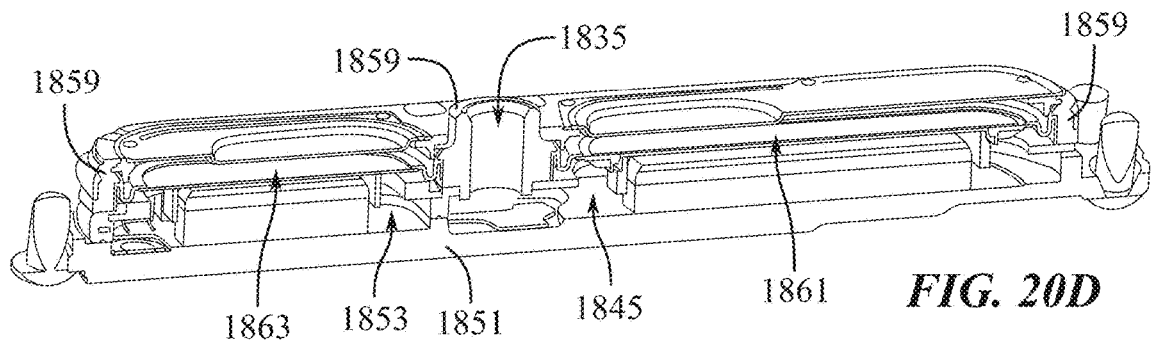
FIG. 20D shows an example of a speaker assembly of an electronic device.
Figure 20E:
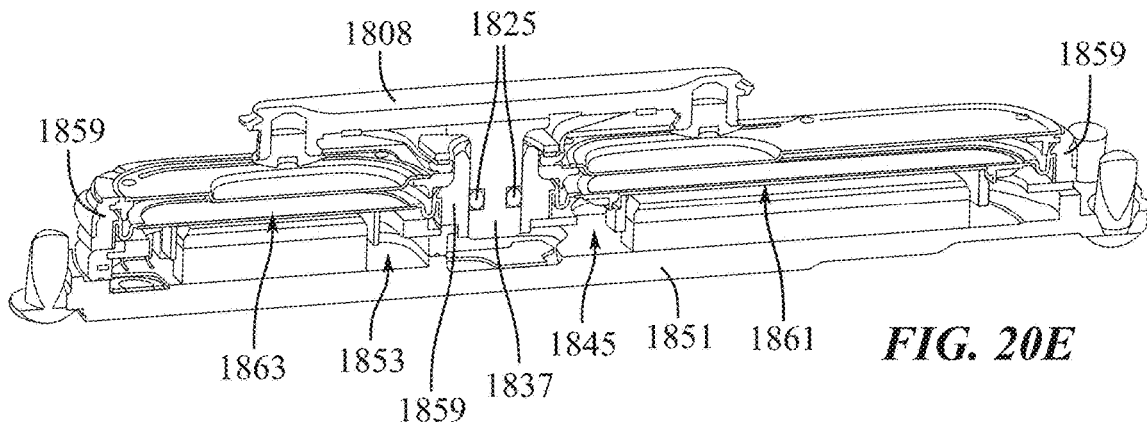
FIG. 20E shows the speaker assembly of FIG. 20D with an example of a button.

In order to accommodate the speaker assembly and the button together in the same area, the speaker frame 1859, as shown in FIG. 20C, can include an opening 1835 defined by the frame 1859. The opening can be positioned to receive one or more components of a button that pass through the frame 1859. FIG. 20D illustrates the frame 1859 supporting the first speaker 1863 and the second speaker 1861 and defining the opening 1835. The opening 1835 can be defined/disposed between the first speaker 1863 and the second speaker 1861. As shown in FIG. 20E, a button 1808 can include a plunger 1837 that is aligned with and/or extends through the opening 1835 between the first speaker 1863 and the second speaker 1861.

In at least one example of the electronic device 1800, the external housing 1802 can define an internal volume 1852 and an aperture 1833, as labeled in FIG. 20B. The button 1808 can be disposed in the aperture 1833. The button 1808 can include the plunger 1837 extending into or toward the internal volume 1852 and the speaker frame 1859 can be disposed in the internal volume 1852 and define the opening 1835. In such an example, the plunger can extend through the opening.

In one example, the frame 1859 can structurally support the first speaker 1863 and the second speaker 1861. The frame 1859 can be disposed in the internal volume 1852 with the frame 1859 defining the opening 1835 (otherwise referred to herein as a "hole") between the first and second speakers 1863, 1861, respectively. In at least one example, the plunger 1837 can be aligned with the hole/opening 1835. A portion of the internal volume 1852 between the inner housing 1851 spaced part from the outer housing 1802 can define a speaker volume including the front volume 1855 and the first and second back volumes 1853, 1845, respectively. The plunger 1837 can be aligned with the hole 1835 and extend into the speaker volume toward the inner housing 1851.

In at least one example, the speaker frame 1859 supports the first speaker 1863 and the second speaker 1861 and the opening 1835 is defined between the first speaker 1863 and the second speaker 1861. Accordingly, in at least one example, the plunger 1837 extends between the first speaker 1863 and the second speaker 1861. In at least one example, the plunger 1837 can extend through the front volume 1855 and into the back volume 1845.

In order to seal off the front volume 1855 from the second back volume 1845, the device 1800 can include a gasket 1825 surrounding the plunger 1837 and forming a fluid-tight seal between the frame 1859 and the plunger 1837. Thus a fluid-tight seal is formed by the gasket 1825 between the front volume 1855 and the second back volume 1845. In at least one example, the gasket can include an O-ring disposed around the plunger 1837. The plunger 1837 can define a recess in which the O-ring can be disposed and positioned between the plunger 1837 and the speaker frame 1859. The materials, size, and shape of the O-ring 1825 can be selected to keep fluid out of the volumes surrounding the speakers 1863, 1861 and to tune the tactile sensation experienced by the user when depressing the button 1808.

Figure 20F:
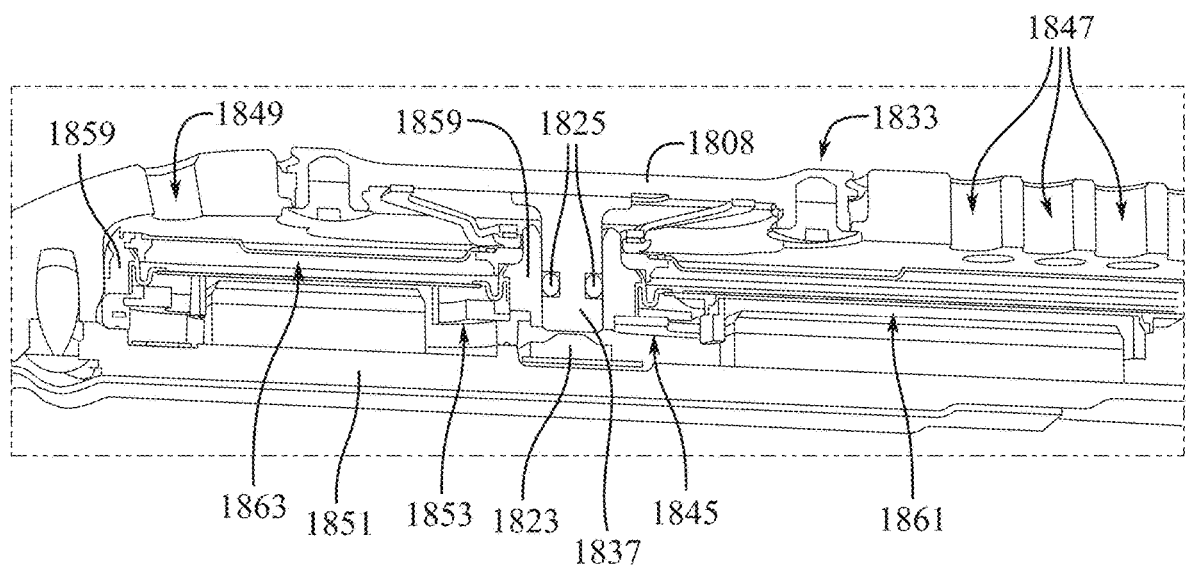
FIG. 20F shows another cross sectional view of the speaker assembly of FIG. 20E.

In addition, as the button is pressed downward, the plunger can make contact with an electrical contact 1823 disposed on the inner housing, as shown in at least FIG. 20F. The plunger is aligned with the electrical contact 1823 so that an electrical pathway or circuit can be completed between the plunger 1837 and the electrical contact 1823 when the button 1808 is pressed down during operation. Accordingly, the plunger can include or be formed from electrically conductive material.

Any of the features, components, and/or parts, including the arrangements and configurations thereof shown in FIGS. 20A-20F can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 20A-20F.

Figure 20G:
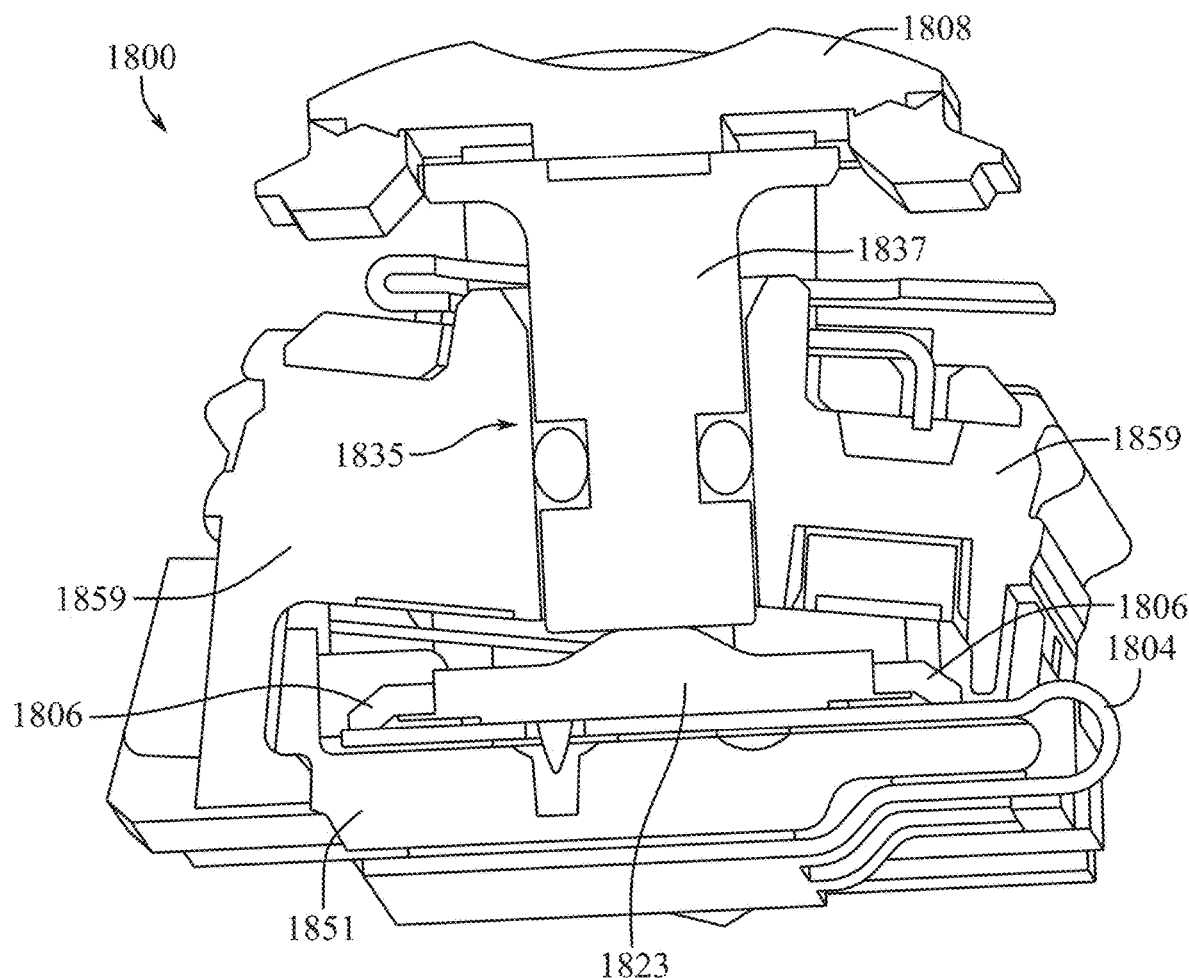
FIG. 20G shows another cross sectional view of the speaker and button assembly of FIG. 20E.

FIG. 20G illustrates a side, cross-sectional view of a portion of the device 1800 showing a viewing plane orthogonal to the cross-sectional viewing plane of FIG. 20F and extending through the plunger 1837. FIG. 20G shows the button 1808 and the plunger 1837 extending through the hole 1835 defined by the speaker frame 1859 and the electrical contact 1823 against which a lower surface of the plunger 1837 presses or contacts when the button 1808 is depressed, as shown, to complete an electrical circuit between the plunger 1837 and the electrical contact 1823. When the button 1808 is not depressed, the plunger 1837 and the electrical contact 1823 are separated so that no electrical connection is made therebetween. The electrical contact 1823 can also be referred to herein as a "tactile switch" or a "tac switch."

The tac switch 1823 can electrically couple and/or physically contact an electrical flex 1804 partially disposed on a top surface of the inner housing 1851 and at least partially extending under the tac switch 1823 between the tac switch 1823 and the inner housing 1851. The flex 1804 can extend around an edge of the inner housing 1851 and continue underneath or on a lower surface, opposite the top surface of the inner housing 1851, as shown. In one example, the bend formed in the flex 1804 as the flex rounds the edge of the inner housing 1851 from one surface to the other can, on its own, bias the portion of the flex 1804 disposed between the tac switch 1823 and the inner housing 1851 away from the inner housing 1851.

In order to counteract this biasing force away from the inner housing 1851, the device 1800 can include a foot 1806 pressing downward onto the flex 1804 to keep the flex 1804 in position between the tac switch 1823 and the inner housing 1851, as shown in FIG. 20G. The foot 1806 can be a molded plastic piece or other non-conductive material anchored to the speaker frame 1859, the inner housing 1851, or other component to produce the force of the foot 1806 pressing the flex 1804 against the inner housing as shown. In at least one example, the foot 1806 can also engage the tac switch 1823 such that the foot 1806 presses the tac switch against or toward the flex 1804 and/or the inner housing 1851. Additionally, or alternatively, one or more adhesives or adhesive layers can be disposed between the flex 1804 and the inner housing 1851, between the tac switch 1823 and the flex 1804, and/or between the tac switch 1823 and the inner housing 1851, to maintain the flex 1804 and tac switch 1823 in position as shown in FIG. 20G.

Any of the features, components, and/or parts, including the arrangements and configurations thereof shown in FIG. 20G can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 20G.

Figure 20H:
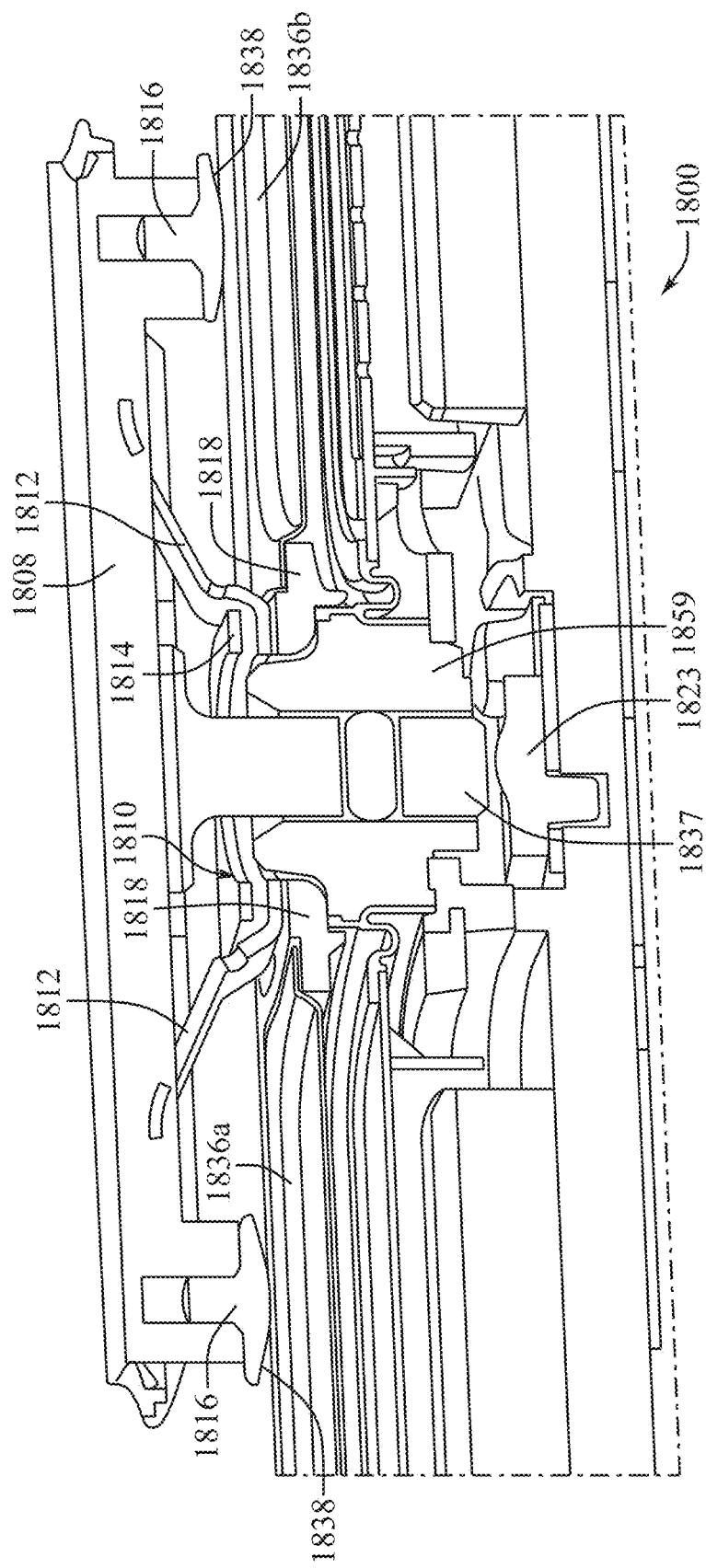
FIG. 20H shows another cross sectional view of the speaker and button assembly of FIG. 20E.

FIG. 20H shows another example of a portion of a device 1800, including a button 1808 and a button spring 1810. In at least one example, the button spring 1810 can include upwardly extending spring arms 1812 fixed to the button 1808. The button spring 1810, and specifically the spring arms 1812, can be formed of conductive material, including metal, and shaped so as to provide an upward biasing force against the button 1808. The button spring 1810 can include a lower portion 1814 anchored to the speaker housing 1859 or other component of the device 1800 relative to which the button 1808 travels when depressed. In at least one example, the button spring 1810 provides a constant force to maintain an upper/outer surface of the button 1808 flush with an outer surface of the housing 1802 of the device 1800 (not shown in FIG. 20H but shown in at least FIGS. 20A and 20B). The materials, shapes, lengths of the spring arms 1814, and other factors of the button spring 1810 can be tuned to alter the tactile response of the button 1808 when depressed by the user.

Referring briefly to FIG. 20A, when the button 1808 is not depressed, an electrical grounding path can be formed through one or more screws 1816 contacting a portion of the housing 1802. Accordingly, the screws 1816 and the housing 1802 can be formed of electrically conductive materials. The screws 1816 can act as a stop feature or datum contacting an inner surface of the housing 1802 to prevent the button 1808 from extending beyond the housing 1802 and maintaining a flush external surface with the housing 1802. Referring again to FIG. 20H, when the button 1808 is partially depressed, the screws 1816 separate from the housing 1802 but the plunger 1837, which is also in electrical communication with the button 1808, is not yet in electrical contact with the tac switch 1823.

Figure 20I:
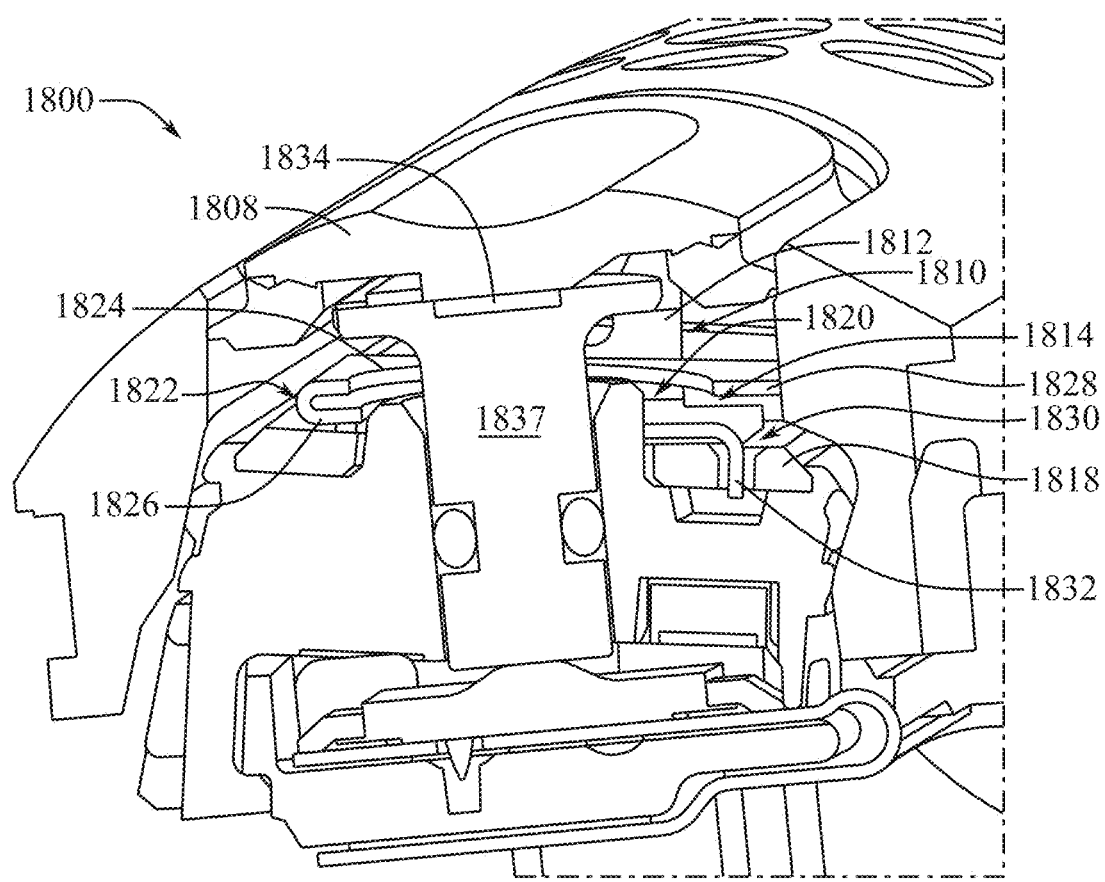
FIG. 20I shows another cross sectional view of the speaker and button assembly of FIG. 20F.

As shown in FIG. 20I, in this partially depressed position of the button 1808, the button spring 1810 can form an electrical grounding pathway between a grounding component or plane of the device 1800 and the button. The button spring 1810 can form such a grounding pathway with the button 1808 whether the button 1808 is fully depressed to contact the plunger against the tac switch 1823, partially depressed as discussed above, or when not depressed. The lower portion 1814 of the button spring 1810 can electrically contact or couple to a collar 1818, which can be coupled to ground, or one or more other components forming the grounding pathway. The spring arms 1812 can contact the button 1808 as shown in FIG. 20H to complete the pathway to the button 1808.

In at least one example, the lower portion 1814 of the button spring 1810 defines an aperture 1820 through which the plunger 1837 extends. In at least one example, the lower portion 1814 of the button spring 1810 forms a bend 1822 that biases portions of the button spring 1810 on either side of the bend 1822 away from each other, contributing to the upward force from the button spring 1810. For example, the bend 1822 can bias a first portion 1824 on one side of the bend 1822 away from a second portion 1826 on the other side of the bend 1822.

In at least one example, the first portion 1824 contacts or extends into the housing 1802 at 1828 to complete an electrical pathway from the button 1808, through the button spring 1810, to the housing 1802. In addition, in at least one example, a collar 1818 defines an aperture 1830 and an anti-rotation feature or extension 1832 of the second portion 1826 can extend through the aperture 1830 or at least partially into the aperture 1830 to prevent the button spring 1810 from rotating out of position as the button 1808 is depressed and travels up and down during use. In at least one example, the anti-rotation feature 1832 engages the collar 1818 without adhesives. In general, the button spring can be disposed and fixed in position as shown without adhesives. The area or volume in which the button spring 1810 is disposed can include an area between the inner housing 1851 and the outer housing 1802 such that any adhesives present could be exposed to chemical aggressors from the external environment, for example through the various vents defined by the housing, including first and second vents 1849 and 1847, respectively. Thus, the button spring 1810 can be fixed in position via the anti-rotation feature 1832, an interface with the housing 1802 at 1828, and/or with the button 1808.

In at least one example, the device 1800 can include a shim 1834 disposed between the button 1808 or the button cap and the plunger 1837. In at least one example, the shim 1834 can include a material more elastic or compressible than the button 1808 and/or the plunger 1837. In one example, the button 1808 and the plunger 1837 include conductive metals and the shim 1834 includes a plastic or rubber material. The shim 1834 can be disposed between and in contact with the button 1808 and the plunger 1837 as shown such that the shim 1834 absorbs forces and movements from the plunger 1837 and the button 1808 as the components of the speakers 1863, 1861 vibrate and pressure sound waves impinge on the plunger 1837 and button 1808, the shim 1834 reduces chattering or buzzing caused by the plunger 1837 and button 1808 vibrating against one another. In at least one example, the shim 1834 can include an elastic material. In at least one example, the shim 1834 can include a compressible material. In at least one example, the compressible material can include foam.

Referring back to FIG. 20H, the device 1800 can include speaker meshes 1836*a*, 1836*b* disposed over speakers 1863, 1861, respectively. Each screw 1816 of the button 1808 can include a lower surface 1838 of the screw head facing the mesh 1836*a-b*. The lower surface 1838 can be chamfered. The meshes 1836*a-b* can be recessed to match or accommodate the curvature of the lower surfaces 1838 of the screws 1816. The recessed geometry of the meshes 1836*a-b* can provide extra space or volume into which the screws 1816 can extend toward the meshes 1836 without the screws 1816 and meshes 1836*a-b* contacting or colliding when the button 1808 is depressed. Additionally, the speaker meshes 1836*a*, 1836*b* can include any number of stacked meshes of varying pore size and material. Pore size can be identified and selected to balance the resistance to ingress of foreign materials, cosmetic benefits, water ejection, and acoustic performance. In some examples, the speaker meshes can both be metal and be welded to the device 1800. In other examples, the meshes can be metal, fabric, polymer, or a combination thereof, and can be attached to the device 1800 by adhesives, fasteners, welding or other joining methods, and the like.

Any of the features, components, and/or parts, including the arrangements and configurations thereof shown in FIGS. 20H-20I can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 20H-20I.

Figure 20J:
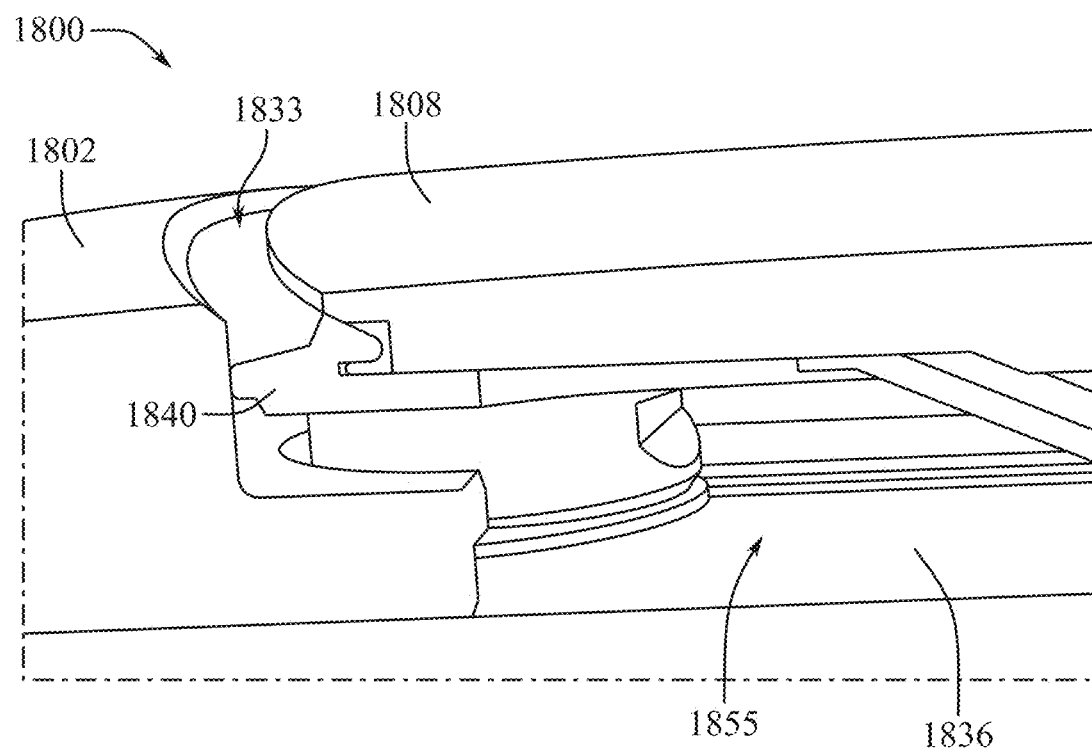
FIG. 20J shows another cross sectional view of the speaker and button assembly of FIG. 20F.

FIG. 20J shows a cross-sectional view of a portion of a device 1800, including a button 1808 disposed in an aperture 1833 defined by a housing 1802 and a speaker diaphragm 1836 disposed in an internal volume of the device 1800. The speaker diaphragm 1836, the button 1808, and the housing 1802 can define the front volume 1855, which is also shown and labeled in FIG. 20A. In at least one example, the device 1800 can include an acoustic gasket 1840 extending between the button 1808 and the housing 1802. In at least one example, the gasket 1840 is greater than or equal to about 100 microns thick where the gasket 1840 contacts the housing 1802. In at least one example, an upper surface of the gasket 1840 interfaces at an angle with the vertical surface of the housing 1802 defining the aperture 1833 at greater than 0-degrees, for example at least about 20-degrees or more relative to the horizontal plane orthogonal to the surface of the housing 1802 defining the aperture 1833. In at least one example, the gasket includes an elastic material. In at least one example, the gasket 1840 includes a material with a Shore-A hardness of between about 30A and 90A, or between about 40A and 80A, or between about 50A and 70A, for example about 60A.

Accordingly, with a gasket 1840 having the above-noted dimensions and material properties, the gasket 1840 can maintain and rebound to its resting shape after the button 1808 is depressed by the user. In addition, according to the above-noted dimensions and material properties, the gasket 1840 can seal the front volume 1855 such that pressure can build up greater than an atmospheric pressure external to the device 1800. In this way, the volume of the first speaker 1863 can be increased. In at least one example, the material properties, shape, and dimensions of the gasket 1840 can be tuned to maximize at least one of the resonant frequencies of the first speaker 1863. In at least one example, the gasket 1840 can be permeable to water but impermeable to dust and debris from the external environment.

The first speaker 1863 can include two peak resonance frequencies, a mechanical resonant frequency generated by shape of the first speaker 1863 itself operating in open air and front port resonance leveraging the length of the first vent 1849 as a tube that creates a higher pitch frequency and lets sound out from the first speaker 1863 through the housing 1802. The pressure built up in the front volume 1855, in part due to the seal formed by the gasket 1840, affects the pressure waves of sound from the first speaker 1863 exiting the first vent 1849. In this way, the gasket 1840 can tune the sound from the first speaker 1863 and increase the resonant tube frequency. In this way, multiple resonant frequencies (mechanical and tube) can be utilized and a broader range of sound frequencies can be increased.

Any of the features, components, and/or parts, including the arrangements and configurations thereof shown in FIG. 20J can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 20J.

Figure 20K:
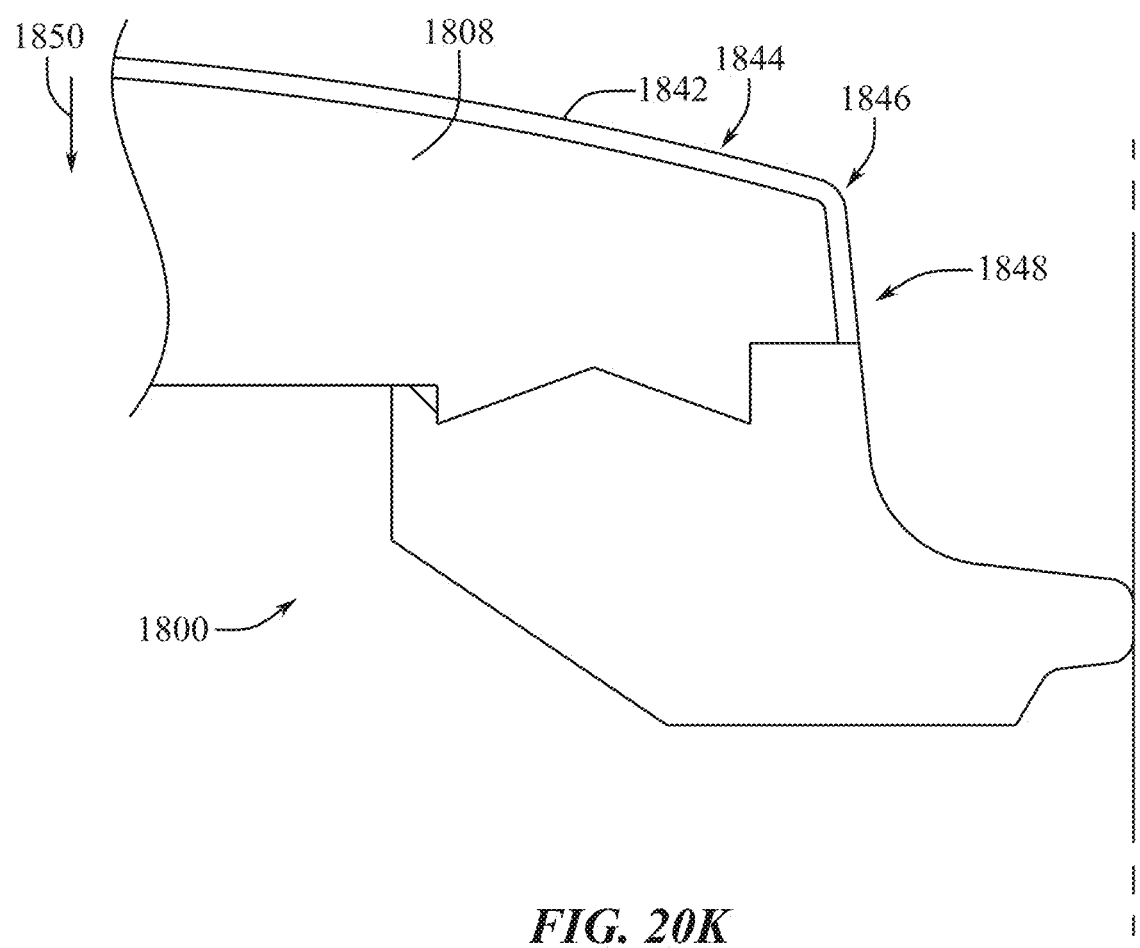
FIG. 20K shows another cross sectional view of the speaker and button assembly of FIG. 20F.

FIG. 20K illustrates a cross-sectional view of a portion of a device 1800 including a button 1808, a housing 1802, and a gasket 1840 extending between the housing 1802 and the button 1808. The button 1808 can include an exterior color layer 1842 that can be formed by physical vapor deposition. The color layer 1842 can also be referred to as a PVD layer 1842. The PVD layer can extend over a first surface 1844 angled or curved at a first angle or curvature and a second surface 1848 angled at a second angle different than the angle of the first surface 1844. During the PVD process of forming the PVD layer 1842, the PVD layer 1842 can be deposited onto the button 1808 in a constant direction regardless of the curvature, angles, or portion of the surface being deposited, in order to simplify the PVD process. In one example, the direction of deposition is indicated by the deposition direction 1850.

Because the first angle of the first surface 1844 is different than the second angle of the second surface 1848, relative to the deposition direction 1850, the PVD layer 1842 deposited on the first surface 1844 is formed thicker than the PVD layer 1842 of the second surface 1848. This can be due to the steeper angle of the second surface 1848 relative to the horizontal plane of FIG. 20K orthogonal to the deposition direction 1850. As shown, the PVD layer 1842 of the second surface 1848 is thinner than the PVD layer 1842 of the first surface 1844 due to this difference in angle relative to the deposition direction 1850. The thickness of the PVD layer 1842 affects the color of the PVD layer 1842. In one example, the thicker PVD layer 1842 at the first surface 1844 can appear red while the color of the PVD layer 1842 at a transition or corner surface 1846 between the first and second surfaces 1844, 1848 can appear blue and the color of the thinner PVD layer 1842 of the second surface 1848 can shift back toward red, for example appearing orange or red-orange. The thickness of the PVD layer 1842 at the corner 1846 can be thicker than the PVD layer 1842 at the second surface 1848 but thinner than the PVD layer 1842 at the first surface 1844.

In the example noted above, the blue color of the PVD layer 1842 at the corner 1846 stands out more visually compared to the red color of the PVD layer 1842 at the first surface 1844 than the orange color of the PVD layer 1842 at the second surface 1848. In order to minimize the contrast of the blue and red between the corner 1846 and the first surface 1844, the corner 1846 can include a small radius of curvature to minimize the area of the surface of the button 1808 defined by the corner 1846. While the PVD layer 1842 at the second surface 1848 is thinner than the PVD layer 1842 at the corner 1846, the orange color of the PVD layer 1842 at the second surface 1848 is closer to red and visually less contrasting or noticeable. Thus, the angle of the second surface 1848 can be chosen to tune the thickness of the PVD layer 1842 on the second surface 1848 relative to the thickness of the PVD layer 1842 of the first surface 1842 in order to minimize the color difference.

In at least one example, the second surface 1848 is angled between about 1-degree and 10-degrees relative to the deposition direction 1850, or between about 3-degrees and about 7-degrees relative to the deposition direction 1850, for example at about 5-degrees relative to the deposition angle 1850. In this way, the thickness of the PVD layer 1842 at the second surface 1848 can be less than about 50% of the thickness or less than the thickness of the PVD layer 1842 of the first surface 1844. In examples where the PVD layer 1842 at the second surface 1848 is less than about 50% of the thickness of the PVD layer 1842 at the first surface, the color difference between the PVD layer 1842 of the first and second surfaces 1844, 1848 can be visually minimized.

Any of the features, components, and/or parts, including the arrangements and configurations thereof shown in FIG. 20K can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 20K.

FIG. 21 illustrates a cross-sectional view of the assembly shown in FIGS. 20A-20F, with 1852 showing an internal volume of the device and 1802 being the outer housing. During manufacturing, in order to simplify machining of the housing 1802, an angled receiving cavity for the speaker assembly can be machined into an inner surface of the housing 1802 so that machining tools can reach needed points in the housing to machine the cavity. Thus, in at least one example, the speaker assembly, including the speaker 1863 shown in FIG. 21, can be disposed at an angle relative to the horizontal plane 1831 of the device 1800. In one example, the speaker angle θ can be between about 5-degrees and 10-degrees from the horizontal plane 1831 of the device 1800, for example about 7.5-degrees, and the cavity angle β can be between about 7-degrees and 13-degrees beyond the speaker angle θ, for example about 10-degrees.

Any of the features, components, and/or parts, including the arrangements and configurations thereof shown in FIG. 21 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 21.

As noted above, the wearable electronic devices described herein can be configured to be used during any daily activity of the user. Often, the wearable device will rub against other objects, including clothing, or be subjected to wind if outside during use. Typically, these types of interactions, including rubbing, scratching, and wind blowing can cause negatively affect the performance of one or more microphones of the device. For example, some wearable devices can include a microphone to receive the user's voice during a cellular call using the device. However, often when speaking in an outside environment where wind is present, the wind can cause unwanted noised as it passed over the device and specifically as it passed over one or more microphone apertures in the housing of the device, which can create unwanted background noise and unclear voice transmission from the device.

Figure 22:
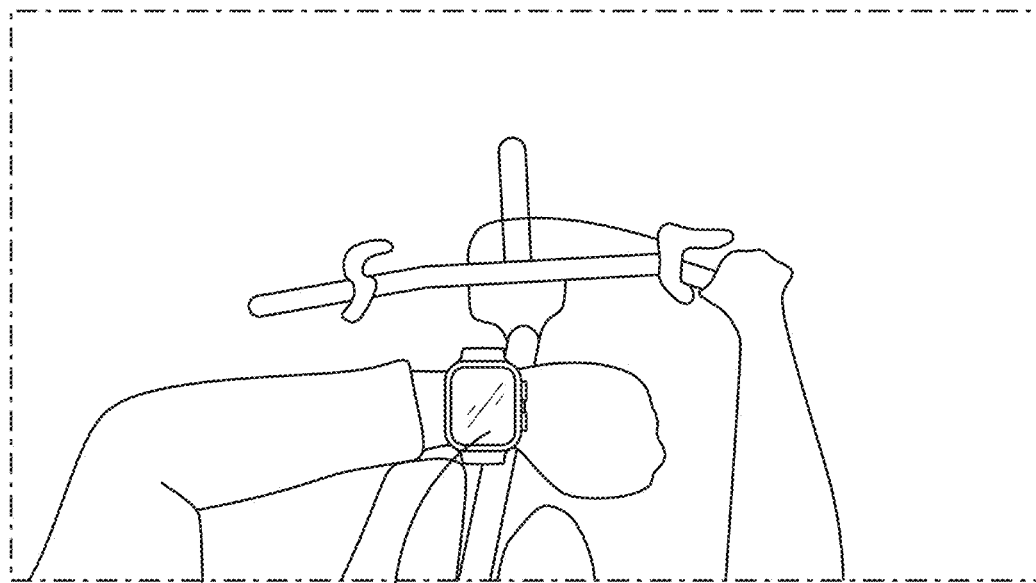
FIG. 22 shows a user riding a bike while wearing an example of a wearable electronic device.
Figure 23:
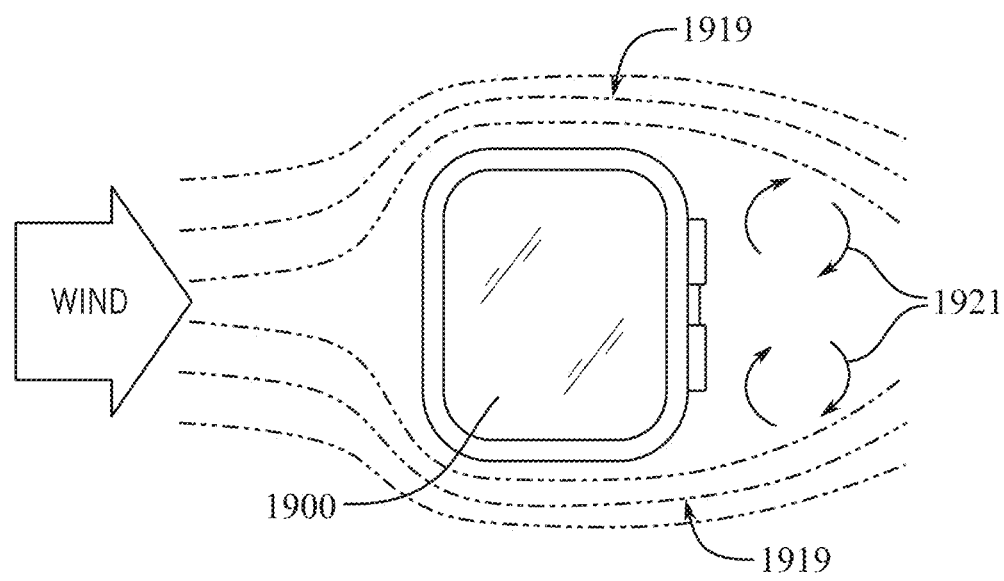
FIG. 23 shows an example of an electronic device subjected to wind.

For example, as shown in FIG. 22, a user is wearing a wearable electronic watch 1900 on his/her wrist while riding a bicycle. Such an activity causes wind to pass over and contact the device 1900. The same may be true while walking, jogging, hiking, or any other active and/or outdoor activity. FIG. 23 shows the device 1900 subject to wind flowing toward and around the device 1900. Flow lines 1919 illustrate one possible flow path of wind crossing over the device 1900. In some examples, turbulent currents 1921 can be created at one or more sides of the device 1900. Such wind and turbulent flow can travel over certain components or opening to microphones and speakers of the device 1900 and cause unwanted noise when transmitting the user's voice during a cellular call or while recording his or her voice with the device 1900.

Figure 24:
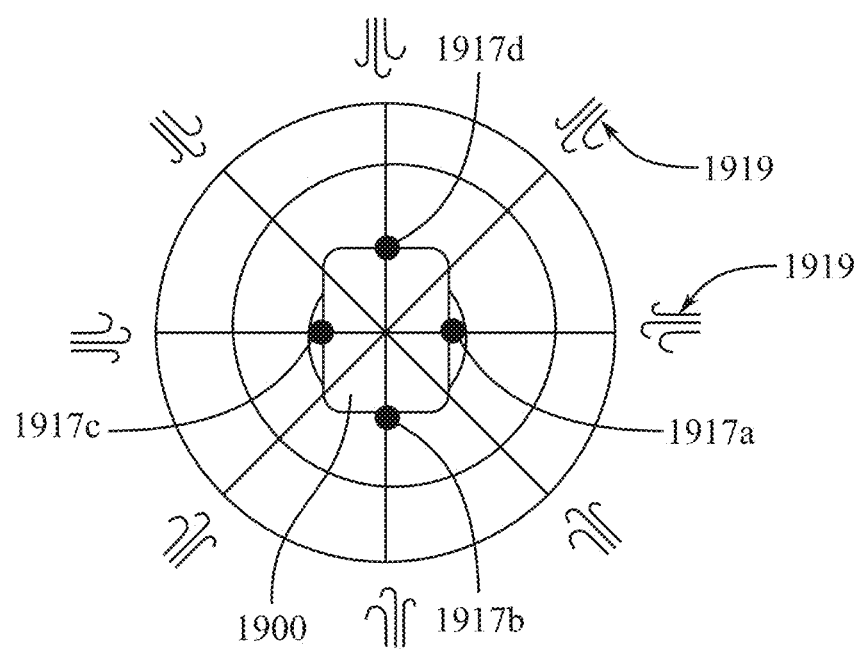
FIG. 24 shows an example of an electronic device subjected to wind from various directions.

The extent of such noise interference from wind can vary depending on the location of the microphone and the direction of the wind. As noted above, the principles discussed with respect to wind interference can also be true for other types of interference such as water and moisture interference and rubbing or scratching the device 1900 against other objects such as clothes. FIG. 24 shows wind 1919 coming from various different directions all around the device 1900. The locations 1917*a*, 1917*b*, 1917*c*, and 1917*d* on the device 1900 illustrate potential locations of a microphone of the device 1900. Again, the extent of noise interference from wind can vary depending on the location of the microphone and the direction of the wind and those directions and locations can vary from one moment to another during use.

In order to reduce the interference from wind and other objects, wearable electronic devices of the present systems and methods can include three microphones disposed in the internal volume of the device and configured to receive sound through three respective apertures, The location and orientation of the apertures and microphones can be such that while one or two of the microphones may pick up wind interference during use, at least one of the microphones and apertures will be positioned and oriented to pick up less interference noise. In such a configuration, the device can be configured to process the combined noise detected by all three microphones to reduce the noise. In one example, the device can be configured to rely more heavily on microphones picking up less interference noise such that the detected noise is clear and un-affected by the interference noise caused by the wind.

Figure 25:
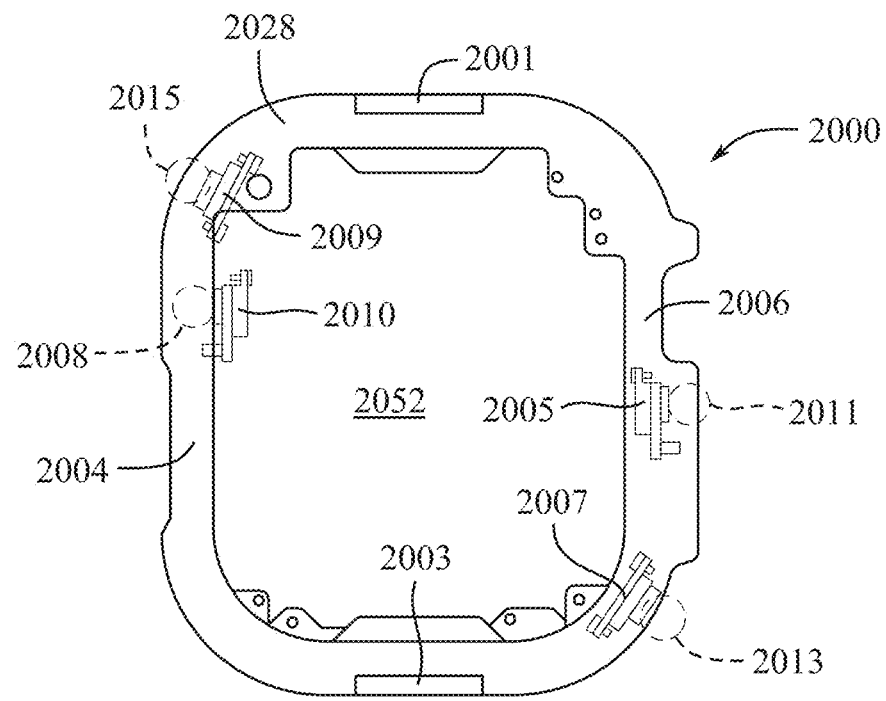
FIG. 25 shows a top view of an example of an electronic device.

In at least one example, as shown in FIG. 25, a wearable electronic watch 2000 can include a housing sidewall 2028 defining an internal volume 2052 with the sidewall 2028 extending 360-degrees circumferentially around the internal volume 2052. The sidewall 2028 can also define a first aperture 2015, a second aperture 2013 between about 155-degrees and 205-degrees relative to the first aperture 2015, and a third aperture 2011 closer to the second aperture 2013 than the first aperture 2015.

In addition, the device 2000 can include a first microphone 2009 disposed in the internal volume 2052 and configured to receive sound through the first aperture 2015, a second microphone 2007 disposed in the internal volume 2052 and configured to receive sound through the second aperture 2013, and a third microphone 2005 disposed in the internal volume 2052 and configured to receive sound through the third aperture 2011.

In one example, the device 2000 can include a first strap receiving feature 2001 and a second strap receiving feature 2003 opposite the first strap receiving feature 2001. A first sidewall portion 2004 can extend between the first strap receiving feature 2001 and the second strap receiving feature 2003 with the first sidewall portion 2004 defining the first aperture 2015 closer to the first strap receiving feature 2001 than the second strap receiving feature 2003. Further, one example can include a second sidewall portion 2006 disposed opposite the first sidewall portion 2004 and extending between the first strap receiving feature 2001 and the second strap receiving feature 2003, the second sidewall portion 2006 defining a second aperture 2013 and a third aperture 2011, the second aperture 2013 defined closer to the second strap receiving feature 2003 than the first strap receiving feature 2001. In such an example, as shown in FIG. 25, the device 2000 can include a first microphone 2009 disposed in the internal volume 2052 adjacent the first aperture 2015, a second microphone 2007 disposed in the internal volume 2052 adjacent the second aperture 2013, and a third microphone 2005 disposed in the internal volume 2052 adjacent the third aperture 2011. While the present system is described as detecting noises and wind from various side directions, the present system can also include microphones oriented to detect sounds and wind from various orientations including into and out of the page illustrated in FIG. 24.

In one example, as shown in FIG. 25, the electronic device 2000 can include a fourth aperture 2008. The first microphone 2009 can be disposed in the internal volume 2052 adjacent the first aperture 2015, the second microphone 2007 can be disposed in the internal volume 2052 adjacent the second aperture 2013, and the third microphone 2005 can be disposed in the internal volume 2052 adjacent the third aperture 2011. In addition, a speaker 2010 can be disposed in the internal volume 2052 adjacent the fourth aperture 2008 such that a distance along the sidewall 2028 between the first and second apertures 2015, 2013 is larger than a distance along the sidewall 2028 between the second and third apertures 2013, 2011 and the fourth aperture 2008 is adjacent the first aperture 2015.

In at least one example, the second aperture 2013 and the third aperture 2011 can be defined on a distal side of the wearable electronic watch. The distal side of the wearable electronic watch 2000 can include or be defined by the second sidewall portion 2006 where the term "distal" refers to anatomically distal when worn on the wrist of the user. In other words, the distal side of the wearable electronic watch 2000 includes the side facing the hand of the user when worn. Conversely, the proximal side of the wearable electronic watch 2000 can include or be defined by the first sidewall portion 2004 where the term "proximal" refers to anatomically proximal when worn on the wrist of the user. In other words, the proximal side of the wearable electronic watch 200 includes the side facing the forearm of the user when worn. In at least one example, the first aperture 2015 can be defined on the proximal side of the wearable electronic watch 2000.

In at least one example, the second aperture 2013 cam be defined between about 170 and 190 degrees relative to the first aperture 2015. In such an example, the third aperture 2011 can be defined between about 30 and 60 degrees counterclockwise along the sidewall 2028 relative to the second aperture 2013. In one example, the third aperture 2011 can be defined between about 40 and 50 degrees counterclockwise along the sidewall 2028 relative to the second aperture 2013.

In at least one example of the wearable electronic watch 2000, the sidewall 2028 defines the strap receiving feature 2001 between the first aperture 2015 and the second aperture 2013. The sidewall 2028 can further define the second strap receiving feature 2003 opposite the first strap receiving feature 2001 and between the third aperture 2011 and the first aperture 2015. In at least one example, the first aperture 2015 can be defined closer to the first strap receiving feature 2001 than the second strap receiving feature 2003 and the second aperture 2013 can be defined closer to the second strap receiving feature 2003 than the first strap receiving feature 2001. In one example, the third aperture 2011 can be defined between the second aperture 2013 and the first strap receiving feature 2001.

In at least one example, the third aperture 2011 is defined between about 30 and 60 degrees counterclockwise from the second aperture 2013 along the housing sidewall 2028. The first aperture 2015 can be defined between about 170 and 190 degrees from the second aperture 2013 along the housing sidewall 2028. In at least one example, the first aperture 2015 can be defined proximally relative to the first strap receiving feature 2001 and the second strap receiving feature 2003 and the second aperture 2013 and the third aperture 2011 can defined distally relative to the first strap receiving feature 2001 and the second strap receiving feature 2003.

In at least one example, the first microphone 2009 can be oriented to receive sound from a first direction and the second microphone 2007 can be oriented to receive sound from a second direction different than the first direction. In one example, the second direction is opposite the first direction. In such an example, the first aperture 2015 and the fourth aperture 2008 can be defined on a proximal side of the electronic device 2000. In such an example, the second and third apertures 2013, 2011 can be defined on a distal side of the electronic device 2000.

Any of the features, components, and/or parts, including the arrangements and configurations thereof shown in FIGS. 22-25 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 22-25.

FIG. 26 illustrates another example of a wearable electronic device 2100 including a sidewall 2128 defining an internal volume 2152 and first, second, and third apertures 2115, 2113, and 2111, respectively. A first microphone 2109 is disposed in the internal volume 2152 adjacent the first aperture 2115 and configured to receive sound through the first aperture 2115. A second microphone 2107 is disposed in the internal volume 2152 adjacent the second aperture 2113 and configured to receive sound through the second aperture 2113. A third microphone 2105 is disposed in the internal volume 2152 adjacent the third aperture 2111 and configured to receive sound through the third aperture 2111. In the illustrated example of FIG. 26, the apertures 2115, 2113, and 2111 are defined by a distal sidewall portion 2106 between the first and second strap receiving features 2101 and 2103, respectively.

Any of the features, components, and/or parts, including the arrangements and configurations thereof shown in FIG. 26 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 26.

Figure 27:
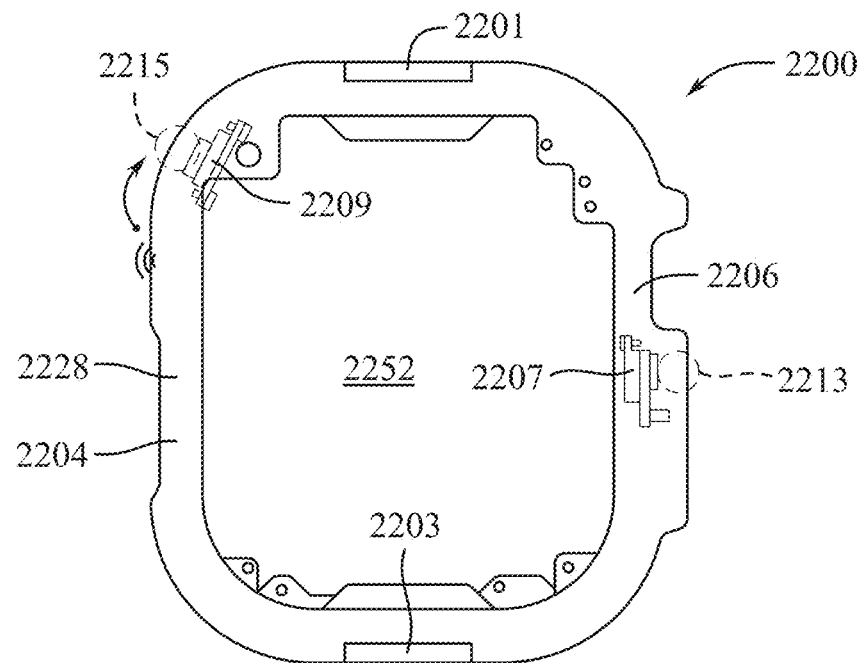
FIG. 27 shows a top view of an example of an electronic device.

FIG. 27 shows another example of a wearable electronic device 2200 including a sidewall 2228 defining an internal volume 2252 and first and second apertures 2215 and 2213, respectively. A first microphone 2209 is disposed in the internal volume 2252 adjacent the first aperture 2215 and configured to receive sound through the first aperture 2215. A second microphone 2207 is disposed in the internal volume 2252 adjacent the second aperture 2213 and configured to receive sound through the second aperture 2213.

In the illustrated example of FIG. 27, the aperture 2215 is defined by a proximal sidewall portion 2204 between the first and second strap receiving features 2201 and 2203, respectively. The second aperture 2213 is defined by a distal sidewall portion 2206 between the first and second strap receiving features 2201 and 2203, respectively.

Any of the features, components, and/or parts, including the arrangements and configurations thereof shown in FIG. 27 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 27.

Figure 28:
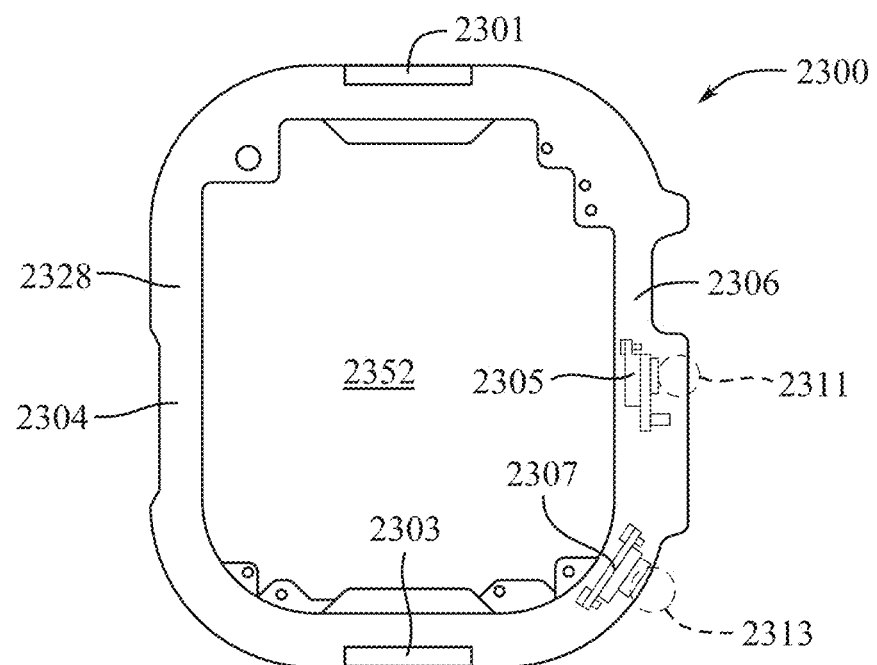
FIG. 28 shows a top view of an example of an electronic device.

FIG. 28 illustrates another example of a wearable electronic device 2300 including a sidewall 2328 defining an internal volume 2352 and first and second apertures 2313 and 2311, respectively. A first microphone 2307 is disposed in the internal volume 2352 adjacent the first aperture 2313 and configured to receive sound through the first aperture 2313. A second microphone 2305 is disposed in the internal volume 2352 adjacent the second aperture 2311 and configured to receive sound through the second aperture 2311. In the illustrated example of FIG. 28, the apertures 2312 and 2111 are defined by a distal sidewall portion 2306 between the first and second strap receiving features 2301 and 2303, respectively.

Any of the features, components, and/or parts, including the arrangements and configurations thereof shown in FIG. 28 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIG. 28.

In each example shown in FIGS. 25-28, the device can be configured to receive and process multiple audio signals from the multiple microphones through the multiple apertures and identify the microphone with the lowest perceived wind noise. This microphone can be used as the baseline and data can be extracted from the other locations to process a clear audio signal. This can improve audio transmission and detection performance in windy conditions, when the device is rubbed against another object, or when one or more microphone apertures gets clogged with debris and/or liquid.

Figure 29A:
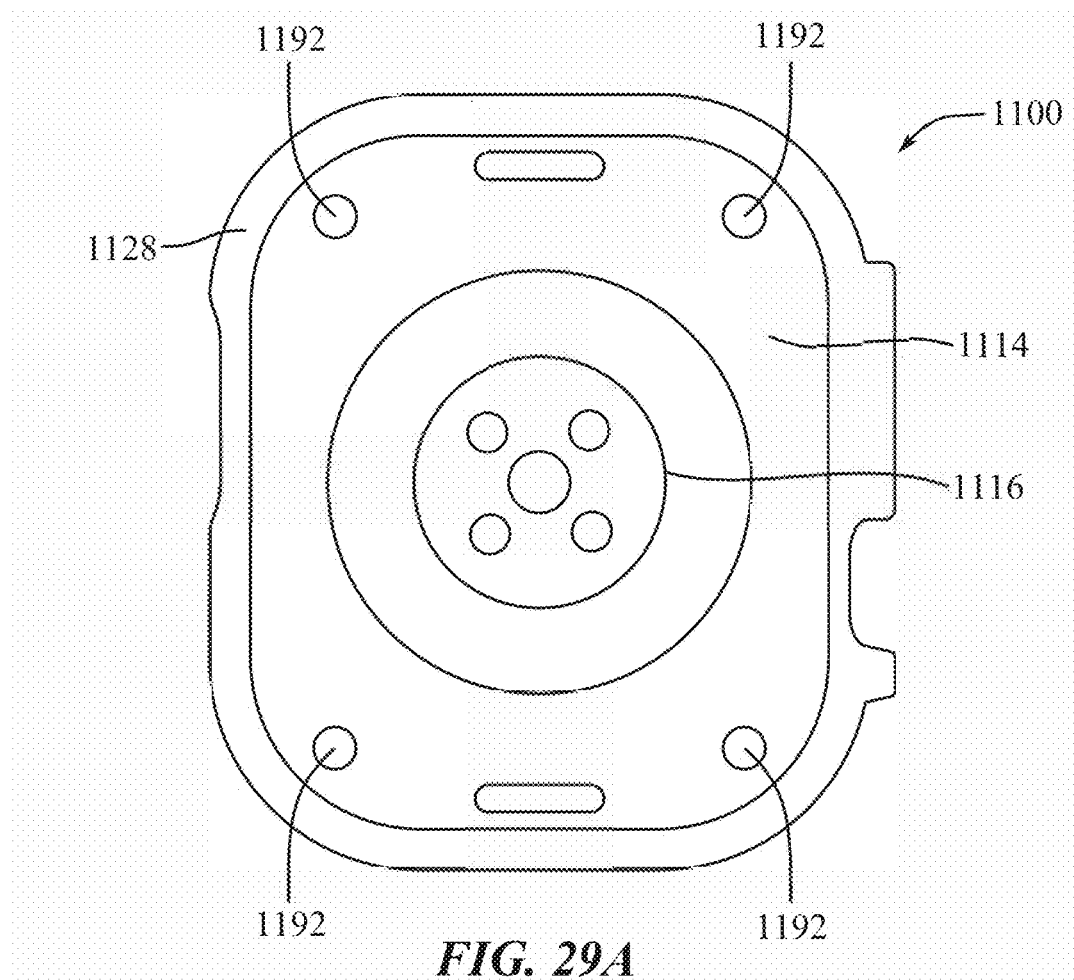
FIG. 29A shows a bottom view of an example of an electronic device.
Figure 29B:
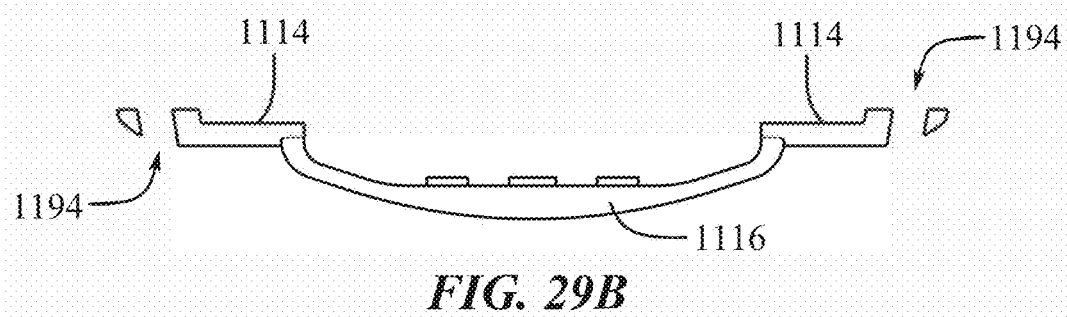
FIG. 29B shows a cross sectional view of a rear cover of an example of an electronic device.

FIG. 29A shows a bottom elevation view of an example of a back cover 1114 and an electromagnetically transparent component 1116 assembled together to form the back side or back surface of a device 1100. In at least one example, the back cover 1114 can be secured to the sidewalls 1128 of the device 1100.

In at least one example, the back cover 1114 can be secured to the sidewalls 1128 using one or more fasteners 1192. In the illustrated example of FIG. 29A, four fasteners 1192 are used to secure the back cover 1114 to the sidewalls 1128, with one fastener 1192 disposed at each corner of the device 1100. Using the fasteners shown, the back cover 1114, which in some examples can be made of ceramic, glass, or other brittle material, the back cover 1114 can be secured to the sidewalls 1128 without cracking, separating from the sidewalls 1128, or otherwise being damaged during assembly.

In at least one example, the back cover 1114 can include zirconia, or other brittle material, which is hard to CNC and machine to form intricate connection features. Using the fasteners shown in the figures to secure the back cover 1114 to the sidewalls 1128 of the device 1100 can simplify the geometry of the back cover 1114 in order to simplify the manufacturing process thereof. For example, as shown in the cross-sectional view of FIG. 15B, the back cover 1114 can be formed of a simple geometry extending around the electromagnetically transparent component 1116 and defining a through hole 1194 for each fastener 1192 to pass through.

In at least one example, each fastener 1192 can be disposed through the back cover 1114 a certain distance away from an outer peripheral edge of the back cover 1114 such that enough material is present between the fastener 1192 and the outer peripheral edge of the back cover 1114 to prevent cracking of the back cover between the fastener and the outer edge. This distance is also designed to reduce any stress concentrations in the back cover 1114 during and after assembly as the fastener 1192 presses the material of the back cover 1114 against the sidewalls 1128.

Figure 30:
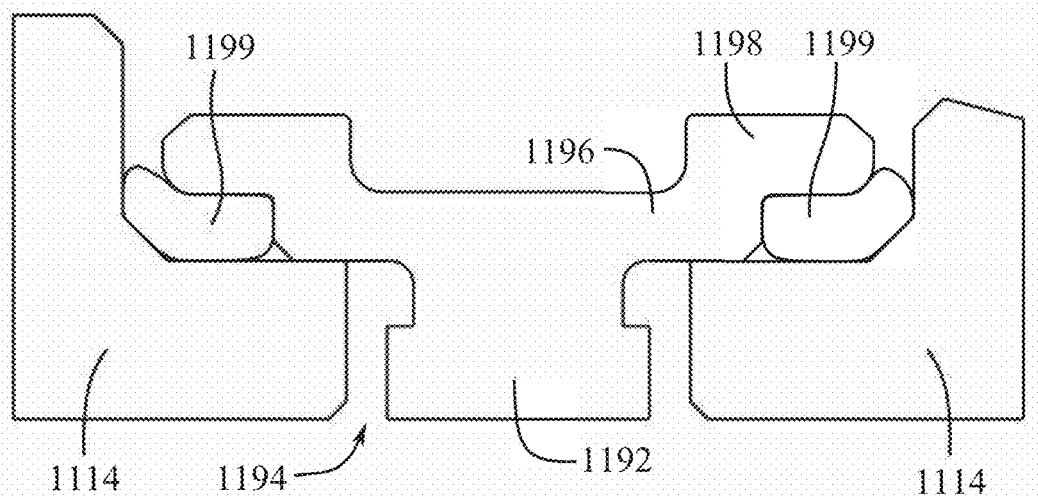
FIG. 30 shows a partial cross-sectional view of a rear cover and a fastener of an example of an electronic device.
Figure 31:
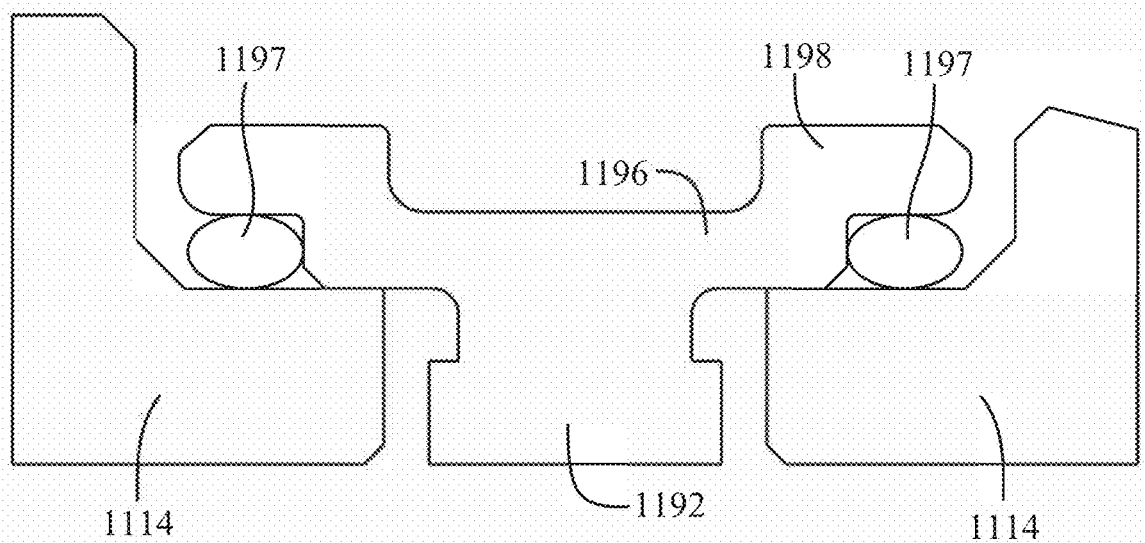
FIG. 31 shows a partial cross-sectional view of a rear cover and a fastener of an example of an electronic device.

As shown in FIGS. 30 and 31, in at least one example, the through hole 1194 defined by the back cover 1114 can include a counter bore in which the head 1196 of the fastener 1192 is disposed when assembled. In addition, in at least one example, the head 1196 of the fastener 1192 can include an outwardly extend flange 1198 with a gasket 1199 pressed between the flange 1198 and the back cover 1114. In one example, the fastener 1192 can include a threaded screw. When assembled, the threaded screw can be threaded into a threaded receiving hole defined by the sidewalls 1128 such that the head 1196 of the fastener 1192 presses the back cover 1114 against the sidewalls 1128.

Figure 32:
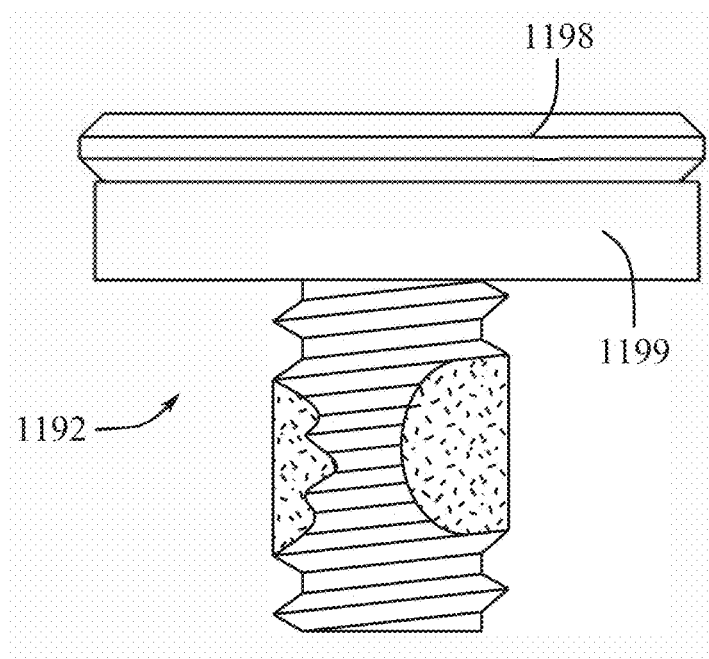
FIG. 32 shows an example of a rear cover fastener.

The flange 1198 thus presses against the gasket 1199 forming an environmental seal against external moisture and other debris from entering the through hole 1194. This environmental seal can also reduce corrosion of the fastener itself as it prevent water or other moisture/fluid from entering the through hole 1194 and coming into contact with the fastener 1192 disposed inside the through hole 1194. FIG. 31 shows an O-ring seal 1197 instead of the gasket shown in the example of FIG. 30, and FIG. 32 shows a side view of the fastener 1192 with the gasket 1199 disposed underneath the flange 1198.

Any of the features, components, and/or parts, including the arrangements and configurations thereof shown in FIGS. 29A-32 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 29A-32.

Figure 33A:
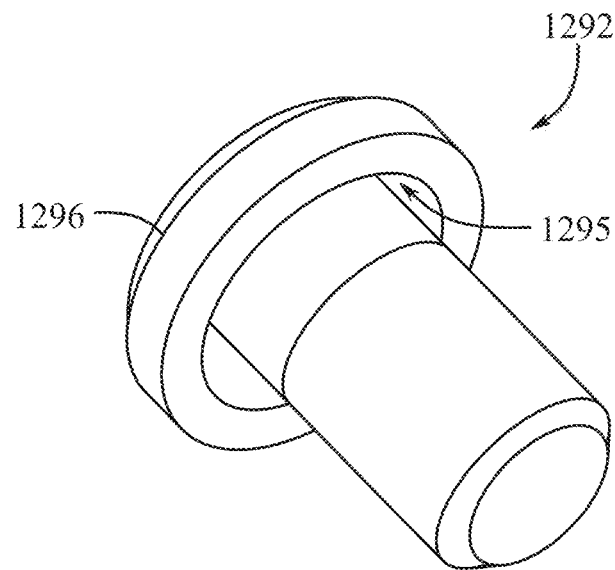
FIG. 33A shows another example of a rear cover fastener.
Figure 33B:
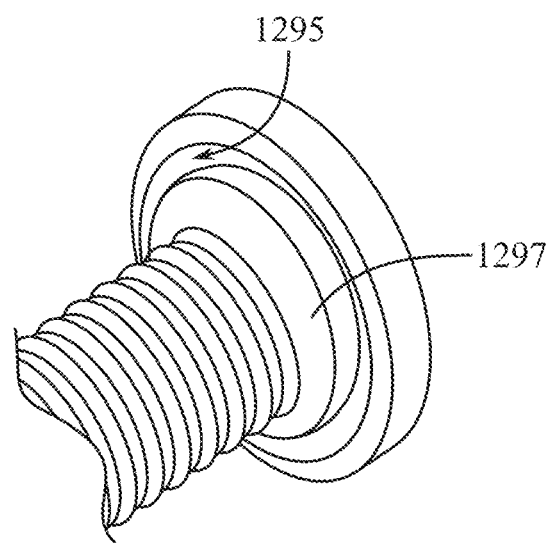
FIG. 33B shows another example of a rear cover fastener.

In at least one example, as shown in FIG. 33A, the fastener 1292 can include an cave feature 1295 defined by the flange 1298 on a lower side of the head 1296 configured to constrain an O-ring or gasket laterally as the fastener 1292 pressed downward on the O-ring or gasket. FIG. 33B shows an example of an O-ring 1297 disposed in the cave feature 1295. Any of the features, components, and/or parts, including the arrangements and configurations thereof shown in FIGS. 33A and 33B can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 33A and 33B.

Figure 34:
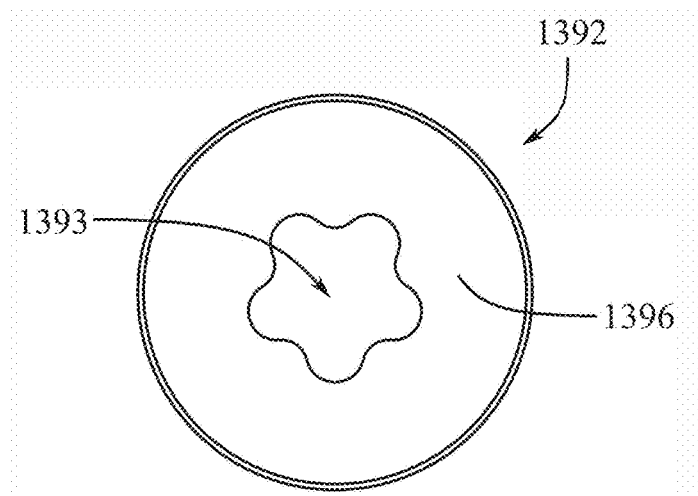
FIG. 34 shows a top view of another example of a fastener.
Figure 35:
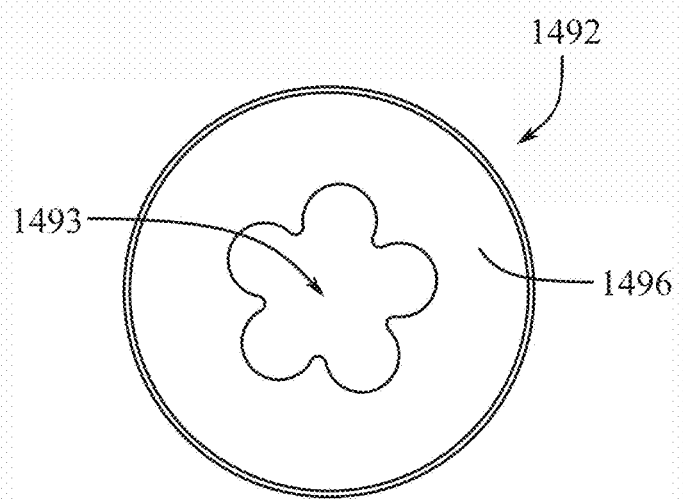
FIG. 35 shows a top view of another example of a fastener.

FIG. 34 illustrates a five-pointed punch 1393 indented into a top surface of the head 1396 of a fastener 1392 with convex transition edges between each of the five points of the punch shape. FIG. 35 illustrates a five-pointed punch 1493 indented into a top surface of the head 1496 of a fastener 1492 with five concave points to form a five-leaf clover shape of the punch 1493. These punches 1393, 1493 can provide aesthetically pleasing punch designs and tool-specific mating features for assembly and disassembly that increase surface area and engagement for secure fastening and removal thereof.

Figure 36A:
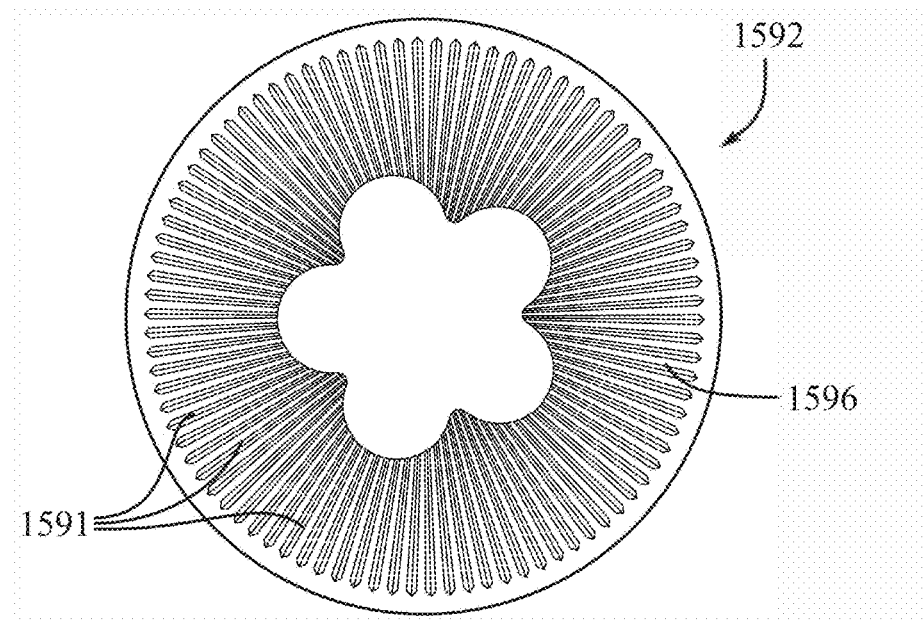
FIG. 36A shows a top view of another example of a fastener.
Figure 36B:
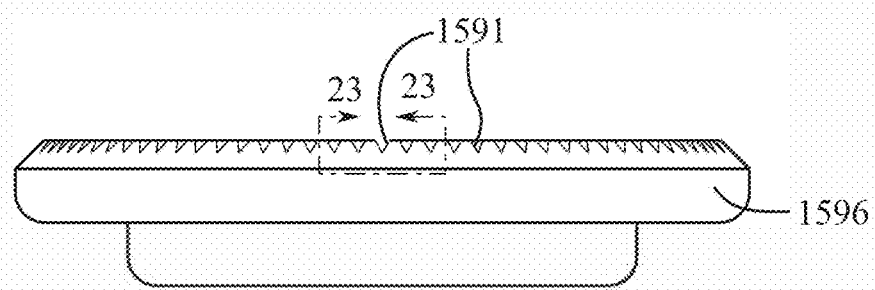
FIG. 36B shows a side view thereof.

Further, as shown in the top and side views of FIGS. 36A and 36B, respectively, the top surface of a fastener head 1596 can include patterns and lines 1591 to further improve the aesthetic appeal, while improving surface engagement and secure removal, of the fastener 1592 and other fasteners described herein and shown in other figures. In at least one example, the lines 1591 can be scored, machines, etches, or otherwise physically formed into the surface of the head 1596. As shown from the side view of FIG. 36B, the lines or scoring features 1591 can be formed to a certain depth into the head 1596 of the fastener 1592.

Figure 37:
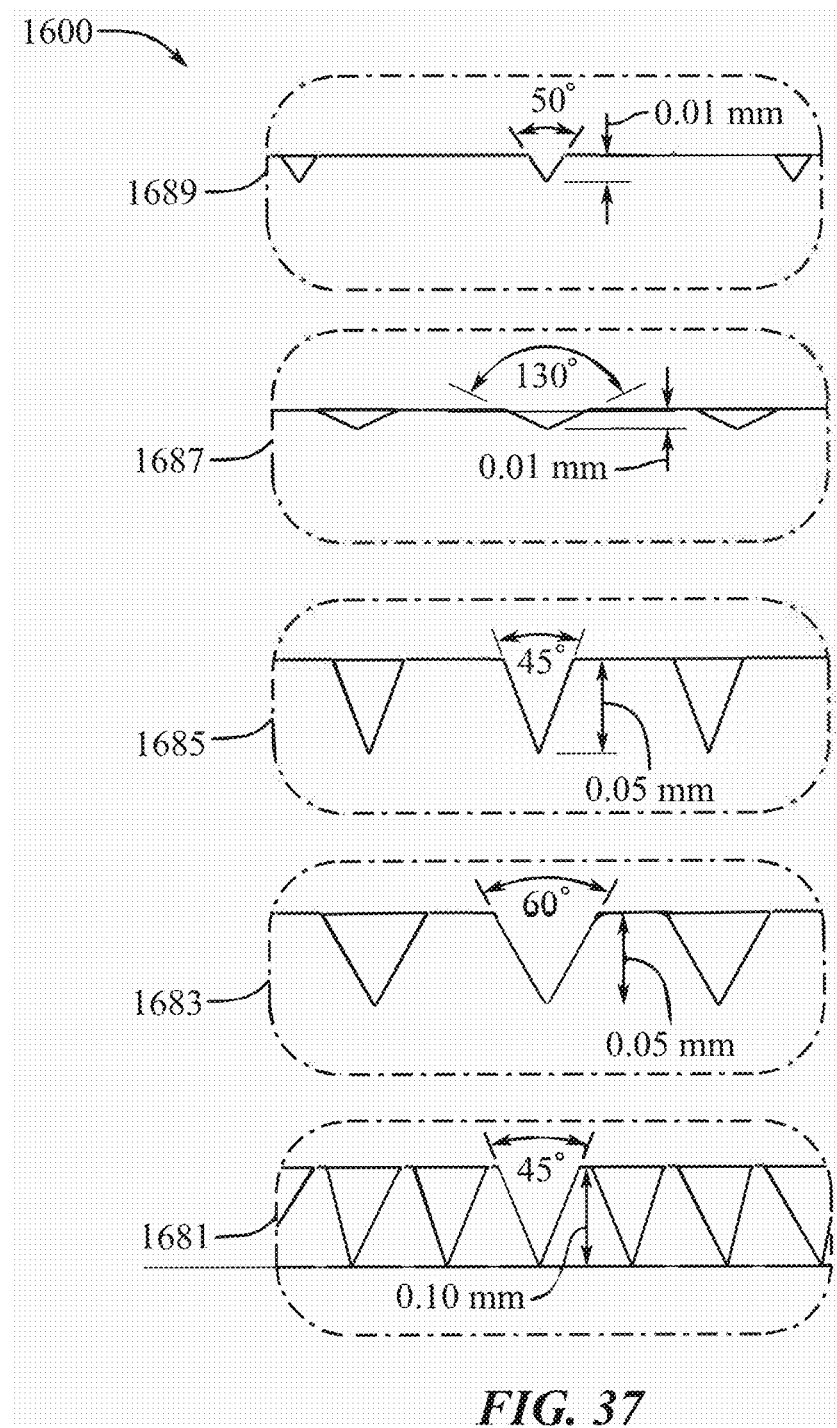
FIG. 37 shows a method of forming the fastener shown in FIG. 36A and FIG. 36B.

FIG. 37 illustrates a flow chart of a method 1600 of forming the score lines and/or machined features 1591 shown in FIGS. 36A and 36B. In a first step of the method 1600, a 50-degree feature is machined or otherwise formed into the surface at a depth of approximately 0.01 mm. Next, in step 1687 of the method 1600, the feature can be widened to approximately 130-degrees at the same depth. Next, at step 1685, the feature can be increased to a depth of approximately 0.05 mm to form an approximately 45-degree feature. Then, at step 1683, the feature can be widened to approximately 60-degrees at the same depth of approximately 0.05 mm. Next, the depth of the feature can be increased to approximately 0.10 mm to form an approximately 45-degree feature. The angles and depth dimensions shown in FIG. 37 and described herein are exemplary only and can vary to form features of different sizes, shapes, number, and depth. In general, the depth and angle of the features can be iteratively widened and deepened as described until the desired depth and angle of each feature is accomplished.

Any of the features, components, and/or parts, including the arrangements and configurations thereof shown in FIGS. 33A-37 can be included, either alone or in any combination, in any of the other examples of devices, features, components, and parts shown in the other figures. Likewise, any of the features, components, and/or parts, including the arrangements and configurations thereof shown in the other figures can be included, either alone or in any combination, in the example of the devices, features, components, and parts shown in FIGS. 33A-37.

Wearable electronic devices currently on the market, including current wearable electronic watches, cannot accurately detect environmental pressures in both submerged environments and above water. Usually, this is because the scale of pressures is so different between air pressure above water and fluid pressure below water. It can be especially difficult to configure a single pressure sensor into such a device that is sensitive enough to detect changes in air pressure above water but robust enough to detect pressure changes under water, for example up to 10-bar under water.

However, devices of the present disclosure, including the wearable electronic devices and watches described herein, can include a single pressure sensor to detect pressure above water and below water up to 10-bar. In at least one example, the pressure sensor can be electrically connected to an ASIC switch and associated circuitry and processors to switch pressure scales when high pressures are detected when the device is submerged under water.

For example, such an ASIC circuitry connected to the sensor can include a low gain mode that measures depth and a high gain mode that measures depth and elevation. This change in gain can be switched with the ASIC to tune the sensor between water and air sensitivities. The processor of the device can also receive temperature measurement from a temperature sensor of the device to take into account the temperature of the external environment, which can affect the pressure sensor reading and sensitivity. Along these lines, at least one example of such a device can also include a heater to apply heat to the pressure sensor in order to perform a health check on the sensor to calibrate the sensor to its original calibration that was performed or set at the same temperature to which it is heated by the heater.

To the extent applicable to the present technology, gathering and use of data available from various sources can be used to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, TWITTER® ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal information data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. An electronic device, comprising:
   a housing sidewall defining an opening;
   a display component disposed in the opening and defining a gap between the housing and the display component;
   a cavity defined by the sidewall and the display component, the cavity in fluid communication with an external environment through the gap;
   an epoxy at least partially defining the cavity and in direct contact with the housing sidewall; and
   an antenna component defining the cavity and in fluid communication with the external environment through the gap.

2. The electronic device of claim 1, wherein the epoxy is at least partially disposed between the display component and the housing.

3. The electronic device of claim 1, further comprising a polymer frame supporting a printed circuit board disposed in an internal volume, the polymer frame stacked between the epoxy and the display component and defining the cavity.

4. The electronic device of claim 1, wherein the display component at least partially defines the cavity.

5. The electronic device of claim 1, wherein the housing sidewall comprises:
   an upper portion;
   a lower portion; and
   a middle portion disposed between the upper portion and the lower portion, the middle portion having a lower surface.

6. The electronic device of claim 5, wherein the epoxy is bonded to the lower surface of the middle portion.

7. An electronic device, comprising:
   a housing sidewall having an upper sidewall portion and a lower sidewall portion bonded to a middle sidewall portion, the middle sidewall portion disposed between the upper and lower sidewall portions, the housing defining an opening;
   a display disposed in the opening and defining a gap between the housing and the display;
   an epoxy seal disposed between the display and the housing, the epoxy extending laterally across the gap, and the epoxy seal bonded directly to the middle sidewall portion; and
   an antenna component disposed between the epoxy seal and the display, the antenna layer defining a cavity in communication with an external environment through the gap.

8. The electronic device of claim 7, wherein the lower sidewall portion and the display define an internal volume.

9. The electronic device of claim 8, wherein the epoxy seal defines at least a part of the internal volume.

10. The electronic device of claim 9, wherein the middle sidewall portion is non-conductive.

11. The electronic device of claim 10, wherein the upper sidewall portion is conductive.

12. The electronic device of claim 7, wherein the housing sidewall, the epoxy seal, and the display define the cavity in fluid communication with the external environment through the gap.

13. An electronic device, comprising:
   a sidewall defining an internal volume and an opening, the sidewall including:
      an upper portion;
      a lower portion; and
      a middle portion disposed between and bonded to the upper portion and the lower portion;
   a display cover disposed in the opening and defining the internal volume;
   a side cavity defined by the display cover and the sidewall, the cavity in fluid communication with an external environment through a gap formed between the display cover and the sidewall;
   an epoxy layer contacting the lower portion and the middle portion and at least partially defining the cavity; and
   an antenna layer disposed between the epoxy layer and the display cover and defining the cavity such that the antenna layer is in fluid communication with the external environment.

14. The electronic device of claim 13, further including an insulating polymer layer disposed between the epoxy layer and the display cover, the polymer layer defining the cavity.

15. The electronic device of claim 13, wherein the epoxy layer is bonded directly to a lower surface of the middle portion.

16. The electronic device of claim 15, wherein the lower portion is bonded directly to the lower surface of the middle portion.

17. The electronic device of claim 13, wherein the middle portion is non-conductive.

18. The electronic device of claim 17, wherein the upper portion is conductive.

* * * * *